US012642805B2

(12) United States Patent
Ren et al.

(10) Patent No.: US 12,642,805 B2
(45) Date of Patent: Jun. 2, 2026

(54) USE OF OXYGENATED CHOLESTEROL SULFATES FOR TREATING AT LEAST ONE OF INSULIN RESISTANCE, DIABETES, AND PREDIABETES

(71) Applicants:Medicis Pharmaceutical Corporation, Bridgewater, NJ (US); Virginia Commonwealth University, Richmond, VA (US); The United States Government as Represented by the Department of Veterans Affairs, Washington, DC (US)

(72) Inventors: Shunlin Ren, Richmond, VA (US); Yaping Wang, Richmond, VA (US); WeiQi Lin, Emerald Hills, CA (US); James E. Brown, Los Gatos, CA (US); Terrence Blaschke, Stanford, CA (US)

(73) Assignees: Medicis Pharmaceutical Corporation, Bridgewater, NJ (US); Virginia Commonwealth University, Richmond, VA (US); The United States Government as Represented by the Department of Veterans Affairs, Washington, DC (US)

( * ) Notice: Subject to any disclaimer, the term of this patent is extended or adjusted under 35 U.S.C. 154(b) by 453 days.

(21) Appl. No.: 18/008,588

(22) PCT Filed: Jun. 25, 2021

(86) PCT No.: PCT/US2021/039215
§ 371 (c)(1),
(2) Date: Dec. 6, 2022

(87) PCT Pub. No.: WO2021/263185
PCT Pub. Date: Dec. 30, 2021

(65) Prior Publication Data
US 2023/0285416 A1 Sep. 14, 2023

Related U.S. Application Data

(60) Provisional application No. 63/149,993, filed on Feb. 16, 2021, provisional application No. 63/149,977, (Continued)

(51) Int. Cl.
*A61K 31/575* (2006.01)
*A61P 3/10* (2006.01)
(Continued)

(52) U.S. Cl.
CPC .............. *A61K 31/575* (2013.01); *A61P 3/10* (2018.01); *A61P 29/00* (2018.01); *A61P 35/00* (2018.01); *A61P 37/02* (2018.01)

(58) Field of Classification Search
CPC .......... A61K 31/575; A61P 3/10; A61P 29/00; A61P 35/00; A61P 37/02; A61P 25/16; (Continued)

(56) References Cited

U.S. PATENT DOCUMENTS

| | | |
|---|---|---|
| 4,427,668 A | 1/1984 | Javitt |
| 4,743,597 A | 5/1988 | Javitt et al. |

(Continued)

FOREIGN PATENT DOCUMENTS

| | | |
|---|---|---|
| EP | 3639828 | 4/2020 |
| JP | H 8239322 | 9/1996 |

(Continued)

OTHER PUBLICATIONS

RxFiles ,Lipid Lowering Agents: Evidence, Questions & Comparisons Feb. 2002, p. 1-7 (Year: 2002).*

(Continued)

*Primary Examiner* — Taylor V Oh
(74) *Attorney, Agent, or Firm* — Morgan, Lewis & Bockius LLP

(57) ABSTRACT

Aspects of the present disclosure include methods for treating at least one of insulin resistance, diabetes, and predia-
(Continued)

betes, and, optionally, also non-alcoholic steatohepatitis (NASH). In practicing the subject methods, an effective amount of at least one compound selected from 25-hydroxycholesterol-3-sulfate (25HC3S), 25-hydroxycholesterol-disulfate (25HCDS), 27-hydroxycholesterol-3-sulfate (27HC3S), 27-hydroxycholesterol-disulfate (27HCDS), 24-hydroxycholesterol-3-sulfate (24HC3S), 24-hydroxycholesterol-disulfate (24HCDS), and 24,25-epoxycholesterol-3-sulfate, or salt thereof is administered to the subject.

20 Claims, 17 Drawing Sheets

Specification includes a Sequence Listing.

Related U.S. Application Data filed on Feb. 16, 2021, provisional application No. 63/146,563, filed on Feb. 5, 2021, provisional application No. 63/146,568, filed on Feb. 5, 2021, provisional application No. 63/146,565, filed on Feb. 5, 2021, provisional application No. 63/146,566, filed on Feb. 5, 2021, provisional application No. 63/146,559, filed on Feb. 5, 2021, provisional application No. 63/141,382, filed on Jan. 25, 2021, provisional application No. 63/127,905, filed on Dec. 18, 2020, provisional application No. 63/044,631, filed on Jun. 26, 2020.

(51) Int. Cl.
| | | |
|---|---|---|
| *A61P 29/00* | (2006.01) | |
| *A61P 35/00* | (2006.01) | |
| *A61P 37/02* | (2006.01) | |

(58) Field of Classification Search
CPC    A61P 25/18; A61P 25/24; A61P 25/30; A61P 25/32; A61P 25/36; A61P 25/28
USPC ........................................................ 514/182
See application file for complete search history.

(56) References Cited

U.S. PATENT DOCUMENTS

| | | | |
|---|---|---|---|
| 8,399,441 | B2 | 3/2013 | Ren et al. |
| 9,034,859 | B2 | 5/2015 | Ren et al. |
| 9,321,802 | B2 | 4/2016 | Ren et al. |
| 9,480,692 | B2 | 11/2016 | Ren |
| 10,144,759 | B2 | 12/2018 | Ren et al. |
| 10,272,097 | B2 | 4/2019 | Ren et al. |
| 10,786,517 | B2 | 9/2020 | Ren et al. |
| 10,844,089 | B2 | 11/2020 | Ren et al. |
| 11,384,115 | B2 | 7/2022 | Ren et al. |
| 11,406,646 | B2 | 8/2022 | Ren et al. |
| 11,612,609 | B2 | 3/2023 | Ren et al. |
| 2007/0197484 | A1 | 8/2007 | Song et al. |
| 2007/0275939 | A1 | 11/2007 | Ren et al. |
| 2010/0273761 | A1 | 10/2010 | Ren et al. |
| 2012/0264816 | A1 | 10/2012 | Ren |
| 2013/0143854 | A1 | 6/2013 | Ren et al. |
| 2015/0072962 | A1 | 3/2015 | Ren |
| 2015/0320769 | A1 | 11/2015 | Ren |
| 2016/0264615 | A1 | 9/2016 | Ren et al. |
| 2016/0355544 | A1 | 12/2016 | Ren |
| 2017/0014429 | A1 | 1/2017 | Ren et al. |
| 2017/0136038 | A1 | 5/2017 | Ren |
| 2017/0252355 | A1 | 9/2017 | Ren et al. |
| 2018/0127457 | A1 | 5/2018 | Ren |
| 2018/0346509 | A9 | 12/2018 | Ren et al. |
| 2019/0083509 | A1 | 3/2019 | Ren et al. |
| 2019/0135856 | A1 | 5/2019 | Ren |
| 2019/0169225 | A1 | 6/2019 | Ren et al. |
| 2019/0269695 | A1 | 9/2019 | Ren et al. |
| 2019/0350945 | A1 | 11/2019 | Ren et al. |
| 2019/0374554 | A1 | 12/2019 | Ren et al. |
| 2020/0009158 | A1 | 1/2020 | Ren |
| 2020/0138831 | A1 | 5/2020 | Ren et al. |
| 2020/0157140 | A1 | 5/2020 | Ren |
| 2020/0222430 | A1 | 7/2020 | Miksztal et al. |
| 2021/0046091 | A1 | 2/2021 | Ren et al. |
| 2021/0147469 | A1 | 5/2021 | Ren et al. |
| 2021/0161913 | A1 | 6/2021 | Ren et al. |
| 2021/0169898 | A1 | 6/2021 | Ren et al. |
| 2021/0169902 | A1 | 6/2021 | Ren et al. |
| 2021/0238219 | A1 | 8/2021 | Ren |
| 2022/0054505 | A1 | 2/2022 | Ren |
| 2022/0175798 | A1 | 6/2022 | Miksztal et al. |
| 2022/0378802 | A1 | 12/2022 | Lin et al. |
| 2023/0047788 | A1 | 2/2023 | Ren et al. |
| 2023/0056273 | A1 | 2/2023 | Miksztal et al. |
| 2023/0141965 | A1 | 5/2023 | Ren et al. |
| 2023/0181601 | A1 | 6/2023 | Lin |
| 2023/0181602 | A1 | 6/2023 | Lin et al. |
| 2023/0218639 | A1 | 7/2023 | Ren et al. |
| 2023/0233580 | A1 | 7/2023 | Ren et al. |
| 2023/0285416 | A1 | 9/2023 | Ren et al. |
| 2023/0293551 | A1 | 9/2023 | Ren et al. |
| 2023/0310458 | A1 | 10/2023 | Ren et al. |
| 2023/0372361 | A1 | 11/2023 | Ren et al. |
| 2024/0425545 | A1 | 12/2024 | Miksztal et al. |

FOREIGN PATENT DOCUMENTS

| | | |
|---|---|---|
| JP | H 0971581 | 3/1997 |
| JP | H 1072421 | 3/1998 |
| WO | WO 2006047022 | 5/2006 |
| WO | WO 2011077245 | 6/2011 |
| WO | WO 2013036835 | 3/2013 |
| WO | WO 2013154752 | 10/2013 |
| WO | WO 2015100312 | 7/2015 |
| WO | WO 2016058000 | 4/2016 |
| WO | WO 2017218379 | 12/2017 |
| WO | WO 2019/236775 | 12/2019 |
| WO | WO 2020072656 | 4/2020 |
| WO | WO 2020150136 | 7/2020 |
| WO | WO 2021067297 | 4/2021 |
| WO | WO 2021133976 | 7/2021 |
| WO | WO 2021154796 | 8/2021 |
| WO | WO 2022272103 | 12/2022 |
| WO | WO 2024136884 | 6/2024 |
| WO | WO 2024138203 | 6/2024 |

OTHER PUBLICATIONS

Al Idrus, "AASLD: Durect's alcoholic hepatitis med repairs liver, cuts mortality in phase 2," Fierce Biotech (2019).
Annual Report, Bringing Ideas to Life (2014).
Athyros, et al (2017) "The use of statins alone, or in combination with pioglitazone and other drugs, for the treatment of non-alcoholic fatty liver disease/non-alcoholic steatohepatitis and related cardiovascular risk. An Expert Panel Statement"; Metabolism Clinical and Experimental, 71; pp. 17-32.
Australian New Zealand Clinical Trials Registry (ANZCTR), "A Multiple Daily Oral Dose Study of DUR-928 in Healthy Volunteers", Trial ID ACTRN 12615000267550, Mar. 20, 2015, web.
Australian New Zealand Clinical Trials Registry (ANZCTR), "A Single Infusion of DUR-928 in Healthy Volunteers", Trial ID ACRTN 12616000856415, Jun. 30, 2016, web.
Australian New Zealand Clinical Trials Registry (ANZCTR), "A Single Injection Dose Study of DUR-928 in Patients with Impaired Kidney Function and Healthy Volunteers" Trial ID ACTRN 12616000389404, Jun. 24, 2016, web.
Australian New Zealand Clinical Trials Registry (ANZCTR), "A Single Oral Dose Study of DUR-928 in Nonalcoholic Steatohepatitis (NASH) Patients and Healthy Volunteers", Trial ID ACTRN 12515001355561, Dec. 14, 2015, web.
Australian New Zealand Clinical Trials Registry (ANZCTR), "A Single and Multiple Daily Injection Study of DUR-928 in Healthy

(56) References Cited

OTHER PUBLICATIONS

Volunteers", Trial ID ACTRN 12615000903583, Aug. 28, 2015, web.

Australian New Zealand Clinical Trials Registry (ANZCTR), "An Intralesional Injection Study of DUR-928 in Psoriasis Patients" Trial ID ACRTN 12616001077459, Aug. 10, 2016, web.

Australian New Zealand Clinical Trials Registry (ANZCTR), "First-in-Human, Single Ascending Oral Dose Study of DV-928 in Healthy Volunteers", Trial ID ACTRN 12614001022651, Sep. 24, 2014, web.

Bai et al., "Oxysterol sulfation by cytosolic sulfotransferase suppresses liver X receptor/sterol regulatory element binding protein-1c signaling pathway and reduces serum and hepatic lipids in mouse models of nonalcoholic fatty liver disease", Metabolism, 2012, pp. 836-845, vol. 61.

Bai Q, et al., "Sulfation of 25-hydroxycholesterol by SULT2B1b decreases cellular lipids via the LXR/SREBP-1c signaling pathway in human aortic endothelial cells"; Atherosclerosis. Feb. 2011; 214(2): 350-356.

Bai, et al (2011) "In Vivo Overexpression of Hydroxysteroid Sulfotransferase SULT2B1b in Mice Reduces Hepatic Lipids and Suppresses SREBP Signaling: Further Evidence for Oxysterol Sulfates as Endogenous Regulators of Hepatic Lipid Metabolism"; *Gastroenterology* 140(5); abstract.

Bai, et al "Overexpression of Oxysterol Sulfotransferase (Sult2B1b) Decreases Intracellular Lipid Levels via SREBPs Signaling Pathway in Primary Human Aorta Endothelial Cells"; Abstract, Arteriosclerosis, Thrombosis, and Vascular Biology 2010 Scientific Sessions, American Heart Association; Apr. 8-10, 2010.

Bi, et al (2018) "Regulation of Cholesterol Sulfotransferase SULT2B1b by Hepatocyte Nuclear Factor 4α Constitutes a Negative Feedback Control of Hepatic Gluconeogenesis"; Molecular and Cellular Biology, vol. 38 Issue 7; pp. 1-15.

Blevins et al., "A Phase 2B Trial in Alcohol-Associated Hepatitis to Evaluate the Safety and Efficacy of Larsucosterol Treatment (AHFIRM);" (poster) SCSG GI Symposium (2022).

Cha and Kim "Sulfated oxysterol 25HC3S as a therapeutic target of non-alcoholic fatty liver disease", Metabolism, 2012, pp. 1055-1057, vol. 61, Elsevier.

Chen et al., "DNA 5-Methylcytosine Demethylation Activities of the Mammalian DNA Methyltransferases," The Journal of Biological Chemistry, 288(13): 9084-9091 (2013).

Clinicaltrials.gov: NCT03432260; "A Research Study to Assess the Safety, Pharmacokinetics and Pharmacodynamics of DUR-928 in Patients With Alcoholic Hepatitis (AH)"; Full Text View; Durect Corporation; Dec. 14, 2022; 9 pages.

Clinicaltrials.gov: NCT03432260; "A Research Study to Assess the Safety, Pharmacokinetics and Pharmacodynamics of DUR-928 in Patients With Alcoholic Hepatitis (AH)"; Tabular View; Durect Corporation; Dec. 14, 2022; 10 pages.

Clinicaltrials.gov: NCT03432260; "A Research Study to Assess the Safety, Pharmacokinetics and Pharmacodynamics of DUR-928 in Patients With Alcoholic Hepatitis (AH)"; Study Results; Durect Corporation; Dec. 14, 2022; 16 pages.

Clinicaltrials.gov: NCT03432260; "A Research Study to Assess the Safety, Pharmacokinetics and Pharmacodynamics of DUR-928 in Patients With Alcoholic Hepatitis (AH)"; History of Changes; Durect Corporation; Nov. 18, 2022; 4 pages.

Clinicaltrials.gov: NCT03917407; "DUR-928 in Patients With Alcoholic Hepatitis (DUR-928/AH)"; Full Text View; Craig James McClain; Nov. 9, 2022; 11 pages.

Clinicaltrials.gov: NCT03917407; "DUR-928 in Patients With Alcoholic Hepatitis (DUR-928/AH)"; Tabular View; Craig James McClain; Nov. 9, 2022; 11 pages.

Clinicaltrials.gov: NCT03917407; "DUR-928 in Patients With Alcoholic Hepatitis (DUR-928/AH)"; Study Results; Craig James McClain; Nov. 9, 2022; 2 pages.

Clinicaltrials.gov: NCT04447404; DUR-928 in Subjects With SARS-CoV-2 With Acute Lung, Liver or Kidney Injury; Tabular View; Durect Corporation; Mar. 2, 2022; 6 pages.

Clinicaltrials.gov: NCT04447404; DUR-928 in Subjects With SARS-CoV-2 With Acute Lung, Liver or Kidney Injury; Full Text View; Durect Corporation; Mar. 2, 2022; 6 pages.

Clinicaltrials.gov: NCT04447404; DUR-928 in Subjects With SARS-CoV-2 With Acute Lung, Liver or Kidney Injury; Study Results; Durect Corporation; Aug. 5, 2022; 9 pages.

ClinicalTrials.gov: NCT04563026; "A Phase 2b Study in Subjects With Alcoholic Hepatitis to Evaluate Safety and Efficacy of DUR-928 Treatment (AHFIRM)"; Tabular View; Durect Corporation; Sep. 24, 2020; 8 pages.

ClinicalTrials.gov: NCT04563026; "A Phase 2b Study in Subjects With Alcoholic Hepatitis to Evaluate Safety and Efficacy of DUR-928 Treatment (AHFIRM)"; Study Details; Durect Corporation; Sep. 24, 2020; 8 pages.

ClinicalTrials.gov: NCT04563026; "A Phase 2b Study in Subjects With Alcoholic Hepatitis to Evaluate Safety and Efficacy of DUR-928 Treatment (AHFIRM)"; Tabular View; Durect Corporation; (update) Aug. 10, 2022; 8 pages.

Clinicaltrials.gov: NCT04563026; A Phase 2b Study in Subjects With Alcoholic Hepatitis to Evaluate Safety and Efficacy of DUR-928 Treatment (AHFIRM); Full Text View; Durect Corporation; (update) Aug. 10, 2022; 7 pages.

Clinicaltrials.gov: NCT04563026; A Phase 2b Study in Subjects With Alcoholic Hepatitis to Evaluate Safety and Efficacy of DUR-928 Treatment (AHFIRM); Durect Corporation; (update) Feb. 23, 2024; 9 pages.

Cook et al. (2009) "24-Hydroxycholesterol Sulfation by Human Sytosolic Sulfotransferases: Formation of Monosulfates and Disulfates, Molecular Modeling, Sulfatase Sensitivity, and Inhibition of Liver X Receptor Activation", Drug Metabolism and Disposition, vol. 37, No. 10; pp. 2069-2078, The American Society for Pharmacology and Experimental Therapeutics.

DePass, et al.; "A 14-Day Intravenous Infusion Toxicity and Toxicokinetic Study of DUR-928, a Novel, First in Class, Investigational Therapeutic in Sprague-Dawley Rats"; American College of Toxicology's 39th Annual Meeting, West Palm Beach, Florida, Nov. 4-7, 2018.

DePass, et al.; "In Vivo Tissue Distribution and Elimination of DUR-928, a First in Class Therapeutic for Treatment of Hepatic and Renal Disease"; Abstract #3355/Poster Board #P137, Late Breaking SOT Poster, Toxicokinetics, 57thAnnual Meeting of the Society of Toxicology, San Antonio, Texas, Mar. 11-15, 2018.

Durect (2015) "Durect Announces Epigenomic Regulator Program including a New NAFLD/NASH and Acute Organ Injury Product Candidate in Development"; News Release, Mar. 2, 2015; 4 pages.

Durect (2015) "Durect Announces Positive Results from DUR-928 Multi-Dose Phase 1 Study"; News Release, May 18, 2015; 4 pages.

Durect (2016) "Durect Announces Positive Phase 1 Data for DUR-928"; News Release, Jan. 6, 2016; 3 pages.

Durect (2016) "Durect Corporation Announces Update on DUR-928 Development Program"; News Release, Oct. 31, 2016; 5 pages.

Durect (2017) "Durect Corporation Announces Update on DUR-928 Development Program"; News Release, Jan. 30, 2017; 4 pages.

Durect (2018) "A Research Study to Evaluate Safety and Efficacy of DUR-928 in Subjects With Primary Sclerosing Cholangitis (PSC)"; U.S. National Library of Medicine, ClinicalTrials.gov Identifier: NCT03394781; 13 pages.

Durect (2018) "Durect Announces Amendment to Accelerate Ongoing Phase 2a Trial of DUR-928 in Alcoholic Hepatitis (AH) by Allowing Dosing of Severe AH Patients in Parallel to Moderate AH Patients" News Release, Nov. 19, 2018; 4 pages.

Durect (2018) "Durect Announces Patient Dosing in Phase 2a Trial of DUR-928 in Alcoholic Hepatitis"; News Release, Apr. 25, 2018; 3 pages.

Durect (2019) "Durect Announces Positive Data from its Phase 2a Clinical Trial of DUR-928 in Alcoholic Hepatitis"; News Release, Sep. 17, 2019; 3 pages.

Durect (2019) "Durect Corporation Announces Preliminary Data from the Ongoing DUR-928 Alcoholic Hepatitis Phase 2a Trial"; News Release, May 7, 2019; 6 pages.

Durect (2020) "Durect Corporation Announces Positive Topline Data from Phase 1b Study of DUR-928 in NASH"; News Release, May 26, 2020; 6 pages.

(56) References Cited

OTHER PUBLICATIONS

Durect (2020) "Durect Corporation Announces Additional Safety Data and Efficacy Signals from Phase 1b Clinical Trial of DUR-928 in NASH Patients at The Liver Meeting Digital Experience™ 2020"; News Release, Nov. 13, 2020; 3 pages.

Durect (2020) "Durect Corporation Announces Top-Line Results from Phase 2a Clinical Trial in Patients with Psoriasis"; News Release, Jan. 2, 2020; 3 pages.

Durect (2021) "Durect Corporation Announces Publication of DUR-928's Mechanism of Action," News Release, Mar. 7, 2021; 2 pages.

Durect (2023), "Durect Corporation Announces Topline Results from Phase 2b AHFIRM Trial of Larsucosterol in Alcohol-Associated Hepatitis with Promising Effect on Mortality," News Release, Nov. 7, 2023; 5 pages.

Durect (2023), "Durect Corporation Reports Third Quarter 2023 Financial Results and Business Update," News Release, Nov. 13, 2023; 6 pages.

Durect (2024), "Durect Corporation Receives FDA Breakthrough Therapy Designation for Larsucosterol in Alcohol-Associated Hepatitis," News Release, May 21, 2024; 3 pages.

Durect Corporate Presentation, 43 pages, Mar. 2, 2015.

Durect Corporation (DRRX) Q3 2023 EarningsCall Transcript, 13 pages (2023).

Durect Corporation presenting at Oppenheimer 34th Annual Healthcare Life Sciences Conference, Feb. 14, 2024 (partial transcript).

Durect Corporation, Epigenomic Regulator Program, Presentation, 17 pages, Mar. 2, 2015.

Durect Corporation, Phase 2b AHFIRM Topline Results, PowerPoint, 15 pages, Nov. 2023.

Durect, (2018) "A Research Study to Assess the Safety, Pharmacokinetics and Pharmacodynamics of DUR-928 in Patients With Alcoholic Hepatitis (AH)"; U.S. National Library of Medicine, ClinicalTrials. gov Identifier: NCT03432260; 14 pages.

Flamm et al., "Drinking Behavior in the AHFIRM Trial as Measured by Phosphatidyl Ethanol," AASLD abstract, S1194-S1195 (2024).

Flamm et al., "Drinking Behavior in the AHFIRM trial as measured by Phosphatidyl Ethanol (PEth)," AASLD poster, 1 page (2024).

Gill et al., "Sterol regulators of cholesterol homeostasis and beyond: The oxysterol hypothesis revisited and revised", Progress in Lipid Research, 2008, pp. 391-404, vol. 47, Elsevier.

Goel et al., "3040: A Balancing Act: Liver Transplantation as an Endpoint in Alcohol-Associated Hepatitis (AH) Trials," AASLD poster, 1 page (2024).

Goel et al., "A Balancing Act: The Life-Saving Potential and Dilemma of Liver Transplantation as an Endpoint in Alcohol-Associated Hepatitis Trials," AASLD abstract, S1116-S1117 (2024).

Hagler, "Get to Know Norman Sussman, Chief Medical Officer at Durect," BioSpace (2021).

Handy et al., "Epigenetic Modifications Basic Mechanisms and Role in Cardiovascular Disease," Circulation, 123:2145-2156 (2011).

Hassanein et al. (2019) "Safety and Efficacy of DUR-928: A Potential New Therapy for Acute Alcoholic Hepatitis," AASLD; Poster; 1 page.

Hassanein et al., "Safety, Pharmacokinetics, & Efficacy Signals of Larsucosterol (DUR-928) in Alcohol-associated Hepatitis," Am J Gastroenterol (2023) 25 pages.

Hassanein, et al (2019) "Safety and Efficacy of DUR-928: A Potential New Therapy for Acute Alcoholic Hepatitis" AASLD; Abstract LB-09 (Durect C928-010 Trial); 1 page.

Hassanein, et al (2019) "Safety and Efficacy of DUR-928: A Potential New Therapy for Acute Alcoholic Hepatitis"; AASLD; 22 pages.

He D., et al, "Inhibition of SULT2B1B expression alters effects of 3 beta-hydroxysteroids on cell proliferation and steroid hormone receptor in human LNCaP prostate cancer cells"; Prostate 67-1318-1329, 2007.

He et al., "Identification and immunohistochemical localization of Sulfotransferase 2B1b (SULT2B1b) in human lung'", Biochimica et Biophysica Acta, Apr. 12, 2005, pp. 119-126, vol. 1724, Elsevier.

Healio, "Alcoholic hepatitis drug candidate shows 'life-saving potential'" (2019).

Healio, "Q&A: DUR-928 'well tolerated' for NASH in Phase 1b study" (2020).

Higashi et al., "Expression of Cholesterol Sulfotransferase (SULT2B1b) in Human Skin and Primary Cultures of Human Epidermal Keralinocytes", The Journal of Investigative Dermatology, 2004, pp. 1207-1212, vol. 122, The Society for Investigative Dermatology.

https://www.hopkinsmedicine.org/health/conditions-and-diseases/hepatitis/alcoholic-hepatitis.

Itoh, et al (1999) "Synthesis of 6- and 7-hydroxyestradiol 17-sulfates: The potential metabolites of estradiol 17-sulfate by female rat liver microsomes"; Steroids 64; pp. 363-370.

Javitt et al., "Cholesterol and hydroxycholesterol sulfotransferases: Identification, distinction from dehydroepiandrosterone sulfotransferase, and differential tissue expression". Endocrinology, vol. 142, pp. 2978-2984, 2001.

Ji et al., "Human Hydroxysteroid Sulfotransferase SULT2B1 Pharmacogenomics: Gene Sequence Variation and Functional Genomics", The Journal of Pharmacology and Experimental Therapeutics, 2007, pp. 529-540, vol. 322, No. 2, The American Society for Pharmacology and Experimental Therapeutics.

Kakiyama, et al (2011) "Characterization of Oxysterols and Their Sulfates in Primary Rat Hepatocytes (Prh) Following Increased Expression of the Mitochondrial Cholesterol Delivery Protein, StarD1"; Gastroenterology 140(5); Abstract; 1 page.

Kemp, "Safety and pharmacokinetics of DUR-928 in patients with nonalcoholic steatohepatitis—A phase 1b study," Journal of Hepatology, 66:S596, abstract (2017).

Kemp, W., "Safety and pharmacokinetics of DUR-928 in patients with non-alcoholic steatohepatitis—A Phase 1b study", EASL The International Liver Congress; Apr. 2017.

Kim MJ, et al; "Attenuation of Renal Ischemic Reperfusion Injury in Rats with DUR-928, a Novel, First-in-Class Therapeutic in Development for Renal Disease"; Poster #: SA-PO650, Kidney Week, San Diego, CA—Oct. 23-28, 2018.

Kim, Mee J., "DUR-928, an endogenous regulatory molecule, exhibits anti-inflammatory and antifibrotic activity in a mouse model of NASH", AASLD's Emerging Trends in NAFLD, Washington DC, vol. 18, Mar. 17-18, 2017.

Lawitz et al., "Efficacy Signals of 4-Week Oral DUR-928 in NASH Subjects;" ePoster at EASL the International Liver Congress; Jun. 23, 2021.

Lawitz et al., "Safety and Efficacy Signals of Daily Oral DUR-928 for 4-Weeks in F1-F3 NASH;" ePoster at AASLD The Liver Meeting; Nov. 13, 2020.

Li et al. (1999) "Sterol synthesis. Preparation and characterization of fluorinated and deuterated analogs of oxygenated derivatives of cholesterol"; Chemistry and Physics of Lipids 99; pp. 33-71.

Li et al., (2006) "A Novel Metabolic Pathway for the Synthesis of the Newly Discovered Nuclear 5-cholesten-3β,25-Diol 3-sulphate", Abstract; 1 page.

Li et al., "Biosynthesis of the regulatory oxysterol, 5-cholesten-3β,25-diol 3-sulfate, in hepatocytes", Journal of Lipid Research, Sep. 21, 2007, pp. 2587-2596, vol. 48.

Li, et al (2007) "Discovery of a novel regulatory pathway in cholesterol metabolism"; The FASEB Journal 21(5); Abstract; 1 page. https://doi.org/10.1096/fasebj.21.5.A239-a.

Li, et al (2008) "25-Hydroxycholesterol 3-sulfate regulates lipid metabolism via SREBP-1 in human macrophages"; The FASEB Journal 22(S1); Abstract; 1 page. https://doi.org/10.1096/fasebj.22.1_supplement.807.6.

Ma et al., "25-Hydroxycholesterol-3-sulfate regulates macrophage lipid metabolism via the LXR/SREBP-1 signaling pathway", Am J Physiol Endocrinol Metab, Oct. 14, 2008, pp. E1369- E1379, vol. 295.

Ma, et al (2009) "Inhibition of cellular lipid biosynthesis by sulfated oxysterol is mediated via the LXR pathway"; The FASEB Journal 23(S1); Abstract; 1 page. https://doi.org/10.1096/fasebj.23.1_supplement.522.1.

Mcclain, Craig J., "Which Therapeutic Targets Will Be The Most Attractive In The Future?", Oct. 2017.

(56) References Cited

OTHER PUBLICATIONS

Mcclain, et al.(2019) "DUR-928 Therapy For Acute Alcoholic Hepatitis: A Pilot Study"; AASLD; Poster (Durect Corporation); 1 page.

Mitchell et al., "Current Management and Future Treatment of Alcoholic Hepatitis," Gastroenterology & Hepatology, 16(4):178-189 (2020).

Napodano, Jason et al., "Zacks Small-Cap Research", Mar. 4, 2015, pp. (1-14).

Ning et al., "Cholesterol metabolites alleviate injured liver function and decrease mortality in an LPS-induced mouse model", Metabolism Clinical and Experimental, 71 (2017), 83-93.

Ning, et al (2009) "Overexpression of mitochondrial cholesterol delivery protein, StAR, decreases intracellular lipids and inflammatory factors secretion in macrophages"; *Atherosclerosis*. 204(1): pp. 114-120.

Ning, et al (2009) "StAR overexpression decreases serum and tissue lipids in apolipoprotein E-deficient mice"; *Lipids* 44(6); pp. 511-519.

Ogawa et al., "A facile synthesis of C-24 and C-25 oxysterols by in situ generated ethyl(trifluoromethyl)dioxirane", Steroids, 2009, pp. 81-87, vol. 74, Elsevier.

Olkkonen et al., "Oxysterols and Their Cellular Effectors," Biomolecules, 2:76-103 (2012).

Pandak, et al., "Reversal of NAFLD through selective increased intracellular hepatic cholesterol catabolism"; Poster Abstract, XXIII International Bile Acid Meeting: Bile Acids as Signal Integrators and Metabolic Modulators, Falk Symposium 194; Oct. 8-9, 2014.

Pandak, et al., "The cholesterol metabolite, 5-cholesten-3beta, 25-diol 3-sulfate, promotes hepatic proliferation in mice"; Poster Abstract, XXII International Bile Acid Meeting: Hepatic and Extrahepatic Targets of Bile Acid Signalling, Falk Symposium 184; Sep. 14-15, 2012.

Polyzos, et al. "Sulfated oxysterols as candidates for the treatment of nonalcoholic fatty liver disease"; Metabolism, 2012, pp. 755-758, vol. 61.

Ren and Ning, "Sulfation of 25-hydroxycholesterol regulates lipid metabolism, inflammatory responses, and cell proliferation", Am J Physiol Endocrinol Metab, Dec. 3, 2013, pp. E123-E130, vol. 306.

Ren et al. (2018) "Novel oxysterol sulfates alleviate injured liver function and decrease mortality in LPS-induced mouse model," *J Clin Gastroenterol Hepatol* vol. 2; 1 page.

Ren et al. "Identification of a novel sulfonated oxysterol, 5-cholesten-3β,25-diol 3-sulfonate, in hepatocyte nuclei and mitochondria"; Journal of Lipid Research, Feb. 27, 2006, pp. 1081-1090, vol. 47, American Society for Biochemistry and Molecular Biology, Inc.

Ren et al., "Identification of A Novel Regulatory Nuclear Oxysterol", Abstract, 56rd Annual Meeting of the American Association for the Study of Liver Diseased, Nov. 11-15, 2005.

Ren et al., "25HC and 25HC3S are Paired Endogenous Ligands of DNA Methyltransferases: Implication for Its Role in Development and Recovery of Non-Alcoholic Fatty Liver Diseases (NAFLD)," Abstract, AASLD Liver meeting, Nov. 4-8, 2022 Washington, DC, USA.

Ren et al., "25HC3S Alleviates Injured Liver Function and Decreases Mortality by Promoter 5mCpG Demethylation Signaling Pathways," AASLD, The Liver Meeting, Boston, Massachusetts (2023); Abstract, 3 pages.

Ren et al., "25HC3S Alleviates Injured Liver Function and Decreases Mortality by Promoter [5m]CpG Demethylation Signaling Pathways," AASLD, The Liver Meeting, Boston, Massachusetts (2023); Poster; 1 page.

Ren et al., "25-hydroxycholesterol and 25-hydroxycholesterol 3-sulfate reciprocally regulate lipid metabolism and inflammation in hepatocytes and macrophages", Abstract, The Liver Meeting, the 60th Annual Meeting of the American Association for the Study of Liver Diseases, Oct. 30-Nov. 3, 2009.

Ren et al., "25-Hydroxycholesterol sulfation regulates lipid metabolism in vivo in mice", Jun. 13-14, 2008; Abstract.

Ren et al., "25-Hydroxycholesterol-3-sulfate (25HC3S) regulates lipid metabolism by activation/inactivation of nuclear orphan receptors in hepatocytes and macrophages", Abstract, XX International Bile Acid Meeting, Falk Symposium 165; Jun. 13-14, 2008.

Ren et al., "Discovery of a Novel Oxysterol, 5-Cholesten-3β,25-Diol3-Sulfonate, in Nuclei and Mitochondria Following Overexpression of the Gene Encoding StarD1", Bile Acids: Biological Actions and Clinical Relevance, 2007 pp. 20-35, Kluwer Academic Publishers.

Ren et al., "Discovery of a Novel Oxysterol, 5-Cholesten-3β,25-Diol3-Sulfonate, in Nuclei and Mitochondria Following Overexpression of the Gene Encoding StarD1", Abstract, International Bile Acid Meeting, XIII Falk Liver Week, Falk Symposia 155, Oct. 6-11, 2006.

Ren et al., "Discovery of a Novel Regulatory Pathway for Maintenance of Intracellular Cholesterol Homeostasis", Abstract, DDW Annual Meeting 2007, May 19-25, 2007.

Ren et al., "Identification of Novel Regulatory Cholesterol Metabolite, 5-Cholesten, 3β,25-Diol, Disulfate" PLOS ONE, 2014, vol. 9. No. 7, p. 1-11.

Ren et al., "Overexpression of Cholesterol Transporter StAR Increases In Vivo Rates of Bile Acid Synthesis in the Rat and Mouse"; Liver Biology and Pathobiology, Aug. 20, 2004, pp. 910-917, vol. 40, No. 4.

Ren et al., "Regulation of Hepatocyte Lipid Metabolism by 25-Hydroxycholesterol-3-Sulfate (25HC3S) Is Mediated Via the LXR/SREBP-1 Signaling Pathway"; Abstract, DDW Annual Meeting 2008, May 17-23, 2008.

Ren S., et al., "Sulfated oxysterol, 25HC3S, is a potent regulator of lipid metabolism in human hepatocytes", ScienceDirect, BBRC, 360 (2007) pp. 802-808.

Ren S., et al.; "The acidic pathway of bile acid biosynthesis: Role in oxysterol sulfation, lipid metabolism and inflammatory responses"; Poster Abstract, XXII International Bile Acid Meeting, Falk Symposia 184; Sep. 14-15, 2012.

Ren, "5-Cholesten-3, 25-diol 3-sulfate has potential to serve as new medication for therapy of inflammatory diseases," BIT Life Sciences' 7th Annual Congress of International Drug Discovery Science and Technology (IDDST), Shanghai, China, Oct. 22-25, 2009.

Ren, "5-cholesten-3beta, 25-diol 3-sulfate serves as a new medicine for therapy of hyperlipidemia," 2nd World Congress on Bioavailability & Bioequivalence: Pharmaceutical R & D Summit, Las Vegas, Jun. 6-8, 2011.

Ren, "5-Cholesten-3β, 25-diol 3-sulfate decreases lipid accumulation in diet-induced nonalcoholic fatty liver disease mouse model," 3nd World Congress on Bioavailability & Bioequivalence: Pharmaceutical R & D Summit, Beijing, China, May 20-22, 2013.

Ren, "Novel cholesterol metabolites for therapy of nonalcoholic fatty liver diseases," BIT's 5th Annual World Congress of Molecular & Cell Biology 2015, Nanjing, China, Apr. 25-28, 2015.

Ren, "Novel Regulatory Pathway in Prevention of Atherosclerosis," Project No. 1101BX001874-01, 7 pages (2013).

Ren, "Novel Regulatory Pathway in Prevention of Atherosclerosis," Project No. 5I01BX001874-02, 7 pages (2014).

Ren, "Novel Regulatory Pathway in Prevention of Atherosclerosis," Project No. 5I01BX001874-03, 7 pages (2014).

Ren, "Novel Regulatory Pathway in Prevention of Atherosclerosis," Project No. 5101BX001874-04, 7 pages (2016).

Ren, "Oxysterol Sulfation as Regulatory Signaling Pathway"; McGuire VA Medical Center, Virginia Commonwealth University; (Apr. 2014) 1 page.

Ren, "Regulation of Cholesterol Metabolism," Project No. 1R01HL078898-01A2, 7 pages (2006).

Ren, "Regulation of Cholesterol Metabolism," Project No. 5R01HL078898-02, 7 pages (2007).

Ren, "Regulation of Cholesterol Metabolism," Project No. 5R01HL078898-03, 7 pages (2008).

Ren, "Regulation of Cholesterol Metabolism," Project No. 5R01HL078898-04, 7 pages (2009).

Ren, "Regulation of Cholesterol Metabolism," Project No. 5R01HL078898-05, 7 pages (2010).

Ren, "Role of oxysterol sulfation in lipid metabolism," Experimental Biology Annual Meeting. Washington D.C., Apr. 9-12, 2011.

(56) References Cited

OTHER PUBLICATIONS

Ren, "Study the role of oxysterol sulfates in NAFLD development," Project No. 5I01BX003656-01A2, 7 pages (2018).

Ren, "Study the role of oxysterol sulfates in NAFLD development," Project No. 5I01BX003656-02, 7 pages (2020).

Ren, "Study the role of oxysterol sulfates in NAFLD development," Project No. 51I01BX003656-03, 7 pages (2021).

Ren, "Study the role of oxysterol sulfates in NAFLD development," Project No. 5I01BX003656-04, 7 pages (2022).

Ren, "Sulfation of 25-Hydroxycholesterol Regulates Lipid Metabolism and Inflammatory Responses in Human Aortic Endothelial Cells, Macrophages, and Hepatocytes"; Abstract; Departments of Medicine, McGuire Veterans Affairs Medical Center Virginia Commonwealth University; (Jan. 2014) 1 page.

Ren, A Novel Regulatory Pathway: Oxysterol Sulfation in Lipid Metabolism and Inflammatory Responses, presentation (Nov. 2011); pp. 1-63.

Ren, et al (2007) "The Nuclear Oxysterol, 5-Cholesten-3β, 25-Diol 3-Sulfate, Decreases Cholesterol Biosynthesis by Inhibiting Expression of HMG CoA Reductase in HepG2 Cells"; *The FASEB Journal* 21(5); Abstract; 1 page. http://doi.org/10.1096/fasebj.21.5.A454-c.

Ren, et al (2010) "Is 25-Hydroxycholesterol 3-Sulfate an Endogenous Ligand of Ppargamma?"; *Gastroenterology* 138(5); Abstract; 1 page.

Ren, et al (2011) "In vivo Oxysterol Sulfation by SULT2B1b Reduces Hepatic Lipid Accumulation and Suppresses SREBP-1c Signaling: Evidence for the Sulfation as a Regulatory Pathway in Lipid Metabolism"; Departments of Medicine, Virginia Commonwealth University/McGuire Veterans Affairs Medical Center; poster; 1 page.

Ren, et al (2021) "Oxysterol Sulfation"; Encyclopedia Publication; 13 pages.

Ren, et al "25-Hydroxycholesterol-3-Sulfate Activates PPARγ and Attenuates Inflammatory Responses in Human Macrophages"; Poster Abstract, Arteriosclerosis, Thrombosis, and Vascular Biology Annual Conference 2009, American Heart Association; Apr. 29-May 1, 2009.

Ren, et al.; "Oxysterol sulfates alleviate injured liver function and decrease mortality in mouse models"; Poster Abstract, XXV International Bile Acid Meeting:Bile Acids in Health and Disease, Symposium 211; Jul. 6-7, 2018.

Ren, Shunlin, "Novel Oxysterol Sulfates Alleviate Injured Liver Function and Decrease Mortality in Mouse Models", Hepatology, Oct. 2017; 2 pages.

Schroepfer, "Oxysterols: Modulators of Cholesterol Metabolism and Other Processes," Physiological Reviews, 80(1): 361-554 (2000).

Shah et al., "Pharmacokinetics of DUR-928 in Alcoholic Hepatitis Patients—A Phase 2a Study;" ePoster at EASL The European Association for the Study of the Liver; Aug. 27, 2020.

Shah et al., "Safety and Pharmacokinetics of DUR-928 in Hepatic Function Impaired Subjects," ePoster at EASL the International Liver Congress; Jun. 23, 2021.

Shah, et al.; "A Clinical Drug-Drug Interaction Study with Midazolam to Assess the Effect of DUR-928 on CYP3A4"; Meeting of the American College of Clinical Pharmacology, Bethesda, Maryland, Sep. 23-25, 2018; 1 page.

Shah, et al.; "Pharmacokinetic and Pharmacodynamic Response in Individual NASH Patients Receiving Two Dose Levels of DUR-928"; NASH Summit—2019, Apr. 22-25, 2019. 1 page.

Shah, et al; "Safety and Single Ascending Dose Pharmacokinetic Study of DUR-928 in Patients with Chronic Kidney Disease versus Matched Control Subjects"; Poster #: SA-PO63; Kidney Week, San Diego, CA—Oct. 23-28, 2018; 1 page.

Shen, et al (2011) "25-Hydroxycholesterol 3-Sulfate (25HC3S): A Physiological Ligand of PPARγ?"; *Gastroenterology* 140(5); Abstract; 1 page.

Shiffman et al., "Results of a phase 2b multicenter randomized trial of larsucosterol for the treatment of severe alcohol-associated hepatitis (AHFIRM trial)," EASL abstract (2024); 2 pages.

Shiffman et al., "Results of a Phase 2b multicenter randomized trial of larsucosterol for the treatment of severe alcohol-associated hepatitis (AHFIRM Trial)," EASL presentation (2024); 18 pages.

Stein et al., "Effects of Timely Treatment on Outcomes of Larsucosterol for Severe Alcohol-Associated Hepatitis (AHFIRM Trial)," AASLD abstract, S548-S549 (2024).

Stein et al., "Larsucosterol for Treatment of Severe Alcohol-associated Hepatitis—Impact of Hospitalization-to-Treat Time," AASLD presentation, 16 slides (2024).

Sussman, "Alcohol-associated Hepatitis Results of a recent trial and remaining questions," BASL/BSG meeting (24 pages) (2024).

Therapeutics, Inc. (2019) "Safety and Efficacy Study of DUR-928 Topical Solution in Subjects With Plaque Psoriasis"; U.S. National Library of Medicine, ClinicalTrials.gov Identifier: NCT03837743; 14 pages.

Tornai and Szabo (2020) "Emerging medical therapies for severe alcoholic hepatitis"; *Clinical and Molecular Hepatology*, 26; pp. 686-696.

Wang and Ren "25-Hydroxycholesterol is a Potent Epigenetic Regulator: High Glucose Induces Lipid Accumulation via 25-Hydroxycholesterol DNA-CpG Methylation in Human Hepatocytes"; Department of Internal Medicine, Virginia Commonwealth University/McGuire VA Medical Centre; AASLD Annual Meeting, Nov. 13-16, 2020. 1 page.

Wang et al. (2021) "25-Hydroxycholesterol 3-sulfate is an endogenous ligand of DNA methyltransferases in hepatocytes"; Journal of Lipid Research. 2021; 62: 100063 (14 pages).

Wang et al., "25HC3S Decreases Insulin Resistance (IR) via DNA 5mCpG in the promoter region Demethylation in Non-Alcoholic Fatty Liver Disease (NAFLD) Mouse Model," Abstract, AASLD Liver meeting, Nov. 4-8, 2022. Washington, DC, USA.

Wang et al., "25-Hydroxycholesterol 3-Sulfate Recovers Acetaminophen Induced Acute Liver Injury via Stabilizing Mitochondria in Mouse Models," Abstract, AASLD Liver meeting, Nov. 4-8, 2022, Washington, DC, USA.

Wang et al., "High Glucose Increases DNA CpG Methylation in Promoter Regions of Insulin Signaling Pathway and Induces Lipid Accumulation in Hepatocytes," South East Lipid Research Conference, Conjunction with University Cincinnati, Sep. 10-13, 2019.

Wang et al., "Larsucosterol: endogenous epigenetic regulator for treating chronic and acute liver diseases," Am J Physiol Endocrinol Metab, 326: E577-E587 (2024).

Wang, et al (2020) "High Glucose Induces Lipid Accumulation via 25-Hydroxycholesterol DNA-CpG Methylation"; iScience 23(5); pp. 1-28.

Wang, et al (2021) "25-Hydroxycholesterol 3-Sulfate Recovers Acetaminophen Induced Acute Liver Injury via Stabilizing Mitochondria in Mouse Models"; Cells 10, 3027; pp. 1-17.

Wang, et al (2021) "Cholesterol Metabolites 25-Hydroxycholesterol and 25-Hydroxycholesterol 3-Sulfate Are Potent Paired Regulators: From Discovery to Clinical Usage"; *Metabolites* 11(1); pp. 2-14.

Xu et al. "Reversal of Diet-induced Serum and Hepatic Lipid Accumulation by 5-cholesten-3beta.25-diol 3-sulfate in Mouse Models of Nonalcoholic Fatty Liver Diseases"; Hepatology, Jun. 9, 2011.

Xu et al., "25HC3S Regulates Lipid Metabolism via LXRs-independent Pathway in An MASLD In Vitro Model," Poster, DDW (2024).

Xu et al., "25-Hydroxycholesterol (25HC) and 25HC-3-Sulfate (25HC3S) Mediate Nuclear Orphan Receptors in Opposite Direction in Hepatocytes", Abstract, XX International Bile Acid Meeting, Falk Symposia 165, Jun. 13-14, 2008.

Xu et al., "25-Hydroxycholesterol-3-sulfate (25HC3S) Attenuates Hepatocyte Intracellular Lipid Levels and Inflammatory Response via LXR/SREBPs and IKBa/NF-KB Pathways", Abstract, DDW Annual Meeting 2008, May 3, 2010.

Xu et al., "25-Hydroxycholesterol-3-Sulfate (25HC3S) Suppresses NF-κB Activatioand Inflammatory Response in Human Macrophages and Hepatocytes", Abstract, Arteriosclerosis, Thrombosis, and Vascular Biology 2010 Scientific Sessions, American Heart Association; Apr. 8-10, 2010.

(56) References Cited

OTHER PUBLICATIONS

Xu et al., "25-Hydroxycholesterol-3-sulfate attenuates inflammatory response via PPARγ signaling in human THP-1 macrophages", Am J Physiol Endocrinol Metab, Jan. 24, 2012, pp. E788-E799, vol. 302.

Xu et al., "5-Cholesten-3β,25-Diol 3-Sulfate Decreases Lipid Accumulation in Diet-Induced Nonalcoholic Fatty Liver Disease Mouse Model", Molecular Pharmacology, Mar. 2013, 648-658, vol. 83.

Xu et al., "Induction of IκBα Expression as a Mechanism Contributing to the Anti-inflammatory Activities of Peroxisome Proliferator-activated Receptor-α Activators", Abstract, DDW Annual Meeting 2011, May 7-10, 2011.

Xu et al., "Induction of IKBα Expression Mediates the Anti-Inflammatory Response to 25-Hydroxycholesterol-3-Sulfate (25HC3S) in Primary Rat Hepatocytes and THP-1 Macrophages"; AASLD Abstract; 2011.

Xu et al., "Regulation of Hepatocyte Lipid Metabolism and Inflammatory Response by 25-Hydroxycholesterol and 25-Hydroxycholesterol-3-sulfate", Lipids, 2010, pp. 821-832, vol. 45, AOCS.

Xu et al.. , "25-Hydroxycholesterol-3-Sulfate Decreases Hepatic Steatosis and Inflammation In Mouse Models of Nonalcoholic Fatty Liver Disease by Down-Regulating Sterol Regulatory Element Binding Protein-1c", Abstract, DDW Annual Meeting 2011, May 7-10, 2011.

Xu, et al (2009) "Nuclear Oxysterols, 25HC and 25HC3S, Regulate Nuclear Orphan Receptor Activities and Attenuate Intracellular Lipid Levels"; *The FASEB Journal* 23(S1); Abstract; 1 page. https://doi.org/10.1096/fasebj.23.1_supplement.871.1.

Yang et al., "Bindings of PPARγ ligand-binding domain with 5-cholesten-3β, 25-diol, 3-sulfate: accurate prediction by molecular simulation"; *Journal of Biomlecular Structure and Dynamics*, pp. 1-9 (2019).

Zhang et al., (2011) "SULT2B1b overexpression promotes liver regeneration via inhibiting LXR signaling pathway in mouse with or without Partial Hepatectomy", Poster; Departments of Medicine, Virginia Commonwealth University/McGuire Veterans Affairs Medical Center, Richmond, Virginia.; 1 page.

Zhang et al., (2012) "Cytosolic sulfotransferase 2B1b promotes hepatocyte proliferation gene expression in vivo and in vitro", Am J Physiol Gastrointest Liver Physiol, vol. 303; pp. G344-G355.

Zhang et al., "Cholesterol metabolite, 5-cholesten-3β-25-diol-3-sulfate, promotes hepatic proliferation in mice"; Journal of Steroid Biochemistry and Molecular Biology, 2012, pp. 262-270, vol. 132, Elsevier.

Zhang et al., "Effects of 25-Hydroxycholesterol Sulfation on Liver Regeneration in Normal and Partial Hepatectomy (PHX) Mouse Models"; May 2011, Gastroenterology vol. 140, Issue 5, Supplement 1, p. S-967.

Narayanan, et al.; Larsucosterol Moves Forward as a Treatment Contender for Alcohol-Associated Hepatitis; NEJM Evidence; Published Jan. 28, 2025; 2 pages.

Shiffman, et al.; Larsucosterol for the Treatment of Alcohol-Associated Hepatitis; NEJM Evidence; Published Jan. 28, 2025; 11 pages.

Pang, et al.; Risk factors for mortality in patients with alcoholic hepatitis and assessment of prognostic models: A population-based study; Can J Gastroenterol Hepatol, vol. 29, No. 3, Apr. 2015, 8 pages.

Tujios, et al.; Clinical and pathological spectrum of disease severity among patients with acute liver failure (ALF) undergoing deceased donor liver transplantation; American Association for the Study of Liver Diseases; Published by Wolters Kluwer Health, Inc.; 2025; 24 pages.

Wang et al.; Cholestenoic acid as endogenous epigenetic regulator decreases hepatocyte lipid accumulation in vitro and in vivo; Am J Physiol Gastrointest Liver Physiol 326: G147-G162, 2024; First published Nov. 14, 2023; 16 pages.

Liangpunsakul, et al.; The impact of liver transplantation on endpoint selection in alcohol-associated hepatitis trials; AASLD; Hepatology Communications, 2025; 11 pages.

DURECT Corporation (DRRX) Q4 2024 EarningsCall Transcript; Mar. 26, 2025; 9 pages.

Extended European Search Report dated Jun. 12, 2024 for European Patent Application No. 21828990.8, 13 pages.

International Search Report for PCT Application No. PCT/US2021/039215 dated Dec. 2, 2021, 4 pages.

* cited by examiner

A

LINE 1 Assay

Pos 1    Pos 2   Pos 3       Pos 4

CTCGGTGGTGCGCCGTTTCTTAAGCCGGTCTGAAAAGCGCAATA (700,000 Copies)

| Media | Pos 1 | Pos 2 | Pos 3 | Pos 4 |
|---|---|---|---|---|
| LG | 37.4 | 47.8 | 41.1 | 39.2 |
| HG | 37.3 | 47.6 | 52.4 | 46.6 |
| Vehicle (Ethanol) | 42.4 | 51.0 | 52.1 | 49.1 |
| 25HC3S | 37.4 | 51.5 | 41.7 | 43.5 |

Figure 2

```
                         SEQUENCE LISTING

<160> NUMBER OF SEQ ID NOS: 28

<210> SEQ ID NO 1
<211> LENGTH: 20
<212> TYPE: DNA
<213> ORGANISM: Homo sapiens

<400> SEQUENCE: 1
tcagctccgt caacatctgc                                          20

<210> SEQ ID NO 2
<211> LENGTH: 22
<212> TYPE: DNA
<213> ORGANISM: Homo sapiens

<400> SEQUENCE: 2
atatcctcaa tgtcacaccc aa                                       22

<210> SEQ ID NO 3
```

-continued

```
<211> LENGTH: 22
<212> TYPE: DNA
<213> ORGANISM: Homo sapiens

<400> SEQUENCE: 3
atggtgtgct ctgcttatga ta                                              22

<210> SEQ ID NO 4
<211> LENGTH: 23
<212> TYPE: DNA
<213> ORGANISM: Homo sapiens

<400> SEQUENCE: 4
gcaacaagtc atcccagcat aat                                             23

<210> SEQ ID NO 5
<211> LENGTH: 22
<212> TYPE: DNA
<213> ORGANISM: Homo sapiens

<400> SEQUENCE: 5
tcaatagaca gtgttgagga cc                                              22

<210> SEQ ID NO 6
<211> LENGTH: 22
<212> TYPE: DNA
<213> ORGANISM: Homo sapiens

<400> SEQUENCE: 6
atgttccaga tcccagagtt tg                                              22

<210> SEQ ID NO 7
<211> LENGTH: 22
<212> TYPE: DNA
<213> ORGANISM: Homo sapiens

<400> SEQUENCE: 7
aacaacaaac cagaagtcaa cc                                              22

<210> SEQ ID NO 8
<211> LENGTH: 19
<212> TYPE: DNA
<213> ORGANISM: Homo sapiens

<400> SEQUENCE: 8
cgcttcggag acgagatgc                                                  19

<210> SEQ ID NO 9
<211> LENGTH: 22
<212> TYPE: DNA
<213> ORGANISM: Homo sapiens

<400> SEQUENCE: 9
catgctggta atcatgatca ac                                              22

<210> SEQ ID NO 10
<211> LENGTH: 20
<212> TYPE: DNA
<213> ORGANISM: Homo sapiens

<400> SEQUENCE: 10
caccagccaa cactcagcta                                                 20
```

-continued

```
<210> SEQ ID NO 11
<211> LENGTH: 20
<212> TYPE: DNA
<213> ORGANISM: Homo sapiens

<400> SEQUENCE: 11
gtcattccag ccaaggttgt                                          20

<210> SEQ ID NO 12
<211> LENGTH: 19
<212> TYPE: DNA
<213> ORGANISM: Homo sapiens

<400> SEQUENCE: 12
tgtggacatg gtcacggac                                           19

<210> SEQ ID NO 13
<211> LENGTH: 21
<212> TYPE: DNA
<213> ORGANISM: Homo sapiens

<400> SEQUENCE: 13
catgtacgtt gctatccagg c                                        21

<210> SEQ ID NO 14
<211> LENGTH: 20
<212> TYPE: DNA
<213> ORGANISM: Homo sapiens

<400> SEQUENCE: 14
caatgacccc ttcattgacc                                          20

<210> SEQ ID NO 15
<211> LENGTH: 19
<212> TYPE: DNA
<213> ORGANISM: Homo sapiens

<400> SEQUENCE: 15
cgcgtgctct ggtcataga                                           19

<210> SEQ ID NO 16
<211> LENGTH: 21
<212> TYPE: DNA
<213> ORGANISM: Homo sapiens

<400> SEQUENCE: 16
atcttctgca tcagataggc c                                        21

<210> SEQ ID NO 17
<211> LENGTH: 22
<212> TYPE: DNA
<213> ORGANISM: Homo sapiens

<400> SEQUENCE: 17
tctttcattt gctcgatggt tg                                       22

<210> SEQ ID NO 18
<211> LENGTH: 22
<212> TYPE: DNA
<213> ORGANISM: Homo sapiens

<400> SEQUENCE: 18
aagaatcgga ttcaggtctg tt                                       22
```

-continued

```
<210> SEQ ID NO 19
<211> LENGTH: 22
<212> TYPE: DNA
<213> ORGANISM: Homo sapiens

<400> SEQUENCE: 19
cccgattcct atcatcgatg at                                                22

<210> SEQ ID NO 20
<211> LENGTH: 19
<212> TYPE: DNA
<213> ORGANISM: Homo sapiens

<400> SEQUENCE: 20
atgatggctg ctgctggtt                                                    19

<210> SEQ ID NO 21
<211> LENGTH: 22
<212> TYPE: DNA
<213> ORGANISM: Homo sapiens

<400> SEQUENCE: 21
ctaagaatga agaaagcgct cc                                                22

<210> SEQ ID NO 22
<211> LENGTH: 19
<212> TYPE: DNA
<213> ORGANISM: Homo sapiens

<400> SEQUENCE: 22
tgcgccattg actgcttgt                                                    19

<210> SEQ ID NO 23
<211> LENGTH: 21
<212> TYPE: DNA
<213> ORGANISM: Homo sapiens

<400> SEQUENCE: 23
cgaaaatgaa ggcgtcaaag g                                                 21

<210> SEQ ID NO 24
<211> LENGTH: 20
<212> TYPE: DNA
<213> ORGANISM: Homo sapiens

<400> SEQUENCE: 24
acgtctttgt ggcttttgct                                                   20

<210> SEQ ID NO 25
<211> LENGTH: 20
<212> TYPE: DNA
<213> ORGANISM: Homo sapiens

<400> SEQUENCE: 25
gggaccactt gcttccatta                                                   20

<210> SEQ ID NO 26
<211> LENGTH: 21
<212> TYPE: DNA
<213> ORGANISM: Homo sapiens

<400> SEQUENCE: 26
ggcatcaaac ctagacaggt c                                                 21
```

-continued

```
<210> SEQ ID NO 27
<211> LENGTH: 21
<212> TYPE: DNA
<213> ORGANISM: Homo sapiens

<400> SEQUENCE: 27
ctccttaatg tcacgcacga t                                              21

<210> SEQ ID NO 28
<211> LENGTH: 20
<212> TYPE: DNA
<213> ORGANISM: Homo sapiens

<400> SEQUENCE: 28
ttgattttgg agggatctcg                                                20
```

USE OF OXYGENATED CHOLESTEROL SULFATES FOR TREATING AT LEAST ONE OF INSULIN RESISTANCE, DIABETES, AND PREDIABETES

CROSS REFERENCE TO RELATED APPLICATIONS

The present application claims priority under 35 U.S.C. § 119(e) of U.S. Provisional Application No. 63/044,631, filed Jun. 26, 2020, Provisional Application No. 63/127,905, filed Dec. 18, 2020, Provisional Application No. 63/141, 382, filed Jan. 25, 2021, Provisional Application No. 63/146, 559, filed Feb. 5, 2021, Provisional Application No. 63/146, 563, filed Feb. 5, 2021, Provisional Application No. 63/146, 565, filed Feb. 5, 2021, Provisional Application No. 63/146, 566, filed Feb. 5, 2021, Provisional Application No. 63/149, 568, filed Feb. 5, 2021, Provisional Application No. 63/149, 977, filed Feb. 16, 2021, Provisional Application No. 63/149,993, filed Feb. 16, 2021, the disclosures of which are expressly incorporated by reference herein in their entireties.

STATEMENT OF FEDERALLY SPONSORED RESEARCH AND DEVELOPMENT

The invention was made, in part, with government support under VA Merit Review Grant, Grant No. 1I01BX003656 awarded by Veterans Affairs. The government has certain rights in the invention.

INTRODUCTION

Oxysterols have long been believed to be ligands of nuclear receptors such as liver x receptor (LXR), and they play an important role in lipids homeostasis and immune system, where they are involved in both transcriptional and post-transcriptional mechanisms. Oxysterols are the oxidized form of cholesterol. In vivo, enzymatic transformation of sterols to oxysterols is for biosynthesis of important biological products such as steroid hormones, bile acids, and vitamin D in cells, blood, and tissues. Oxysterols participate in many biological processes including cholesterol homeostasis, triglyceride metabolism, inflammatory responses, cell proliferation, platelet aggregation, and apoptosis. The oxysterols have also been implicated in many diseases such as metabolic syndrome and neurodegenerative diseases. Oxysterols can be sulfated by sulfotransferase 2B1b (SULT2B1b) at the 3-position of the ring A of cholesterol to be oxysterol 3-sulfates including 5-cholesten-3β-25-diol-3-sulphate (25HC3S), 5-cholesten-3β-24-diol-3-sulphate (24HC3S), 5-cholesten-3β-27-diol-3-sulphate (27HC3S) as well as Xol3S (cholesterol 3-sulfate).

It has been shown previously that cholesterol metabolite, 5-cholesten-3β-25-diol-3-sulphate, decreases lipid biosynthesis and increases cholesterol secretion and degradation, and may be useful for the treatment and prevention of hypercholesterolemia, hypertriglyceridemia, and conditions related to fat accumulation and inflammation (e.g., non-alcoholic fatty liver disease (NAFLD), non-alcoholic steatohepatitis (NASH), alcoholic hepatitis, acute kidney injury (AKI), psoriasis, and atherosclerosis). Oxysterols have also been implicated in several diseases such as metabolic syndrome. Oxysterols can be sulfated, and the sulfated oxysterols act in different direction: they decrease lipid biosynthesis, suppress inflammatory responses, and promote cell survival.

SUMMARY

The present disclosure provides methods for treating at least one of insulin resistance, diabetes, and prediabetes, and, optionally, also treating non-alcoholic steatohepatitis (NASH). As discussed in more detail herein, the magnitude of the effect of 25HC3S on insulin resistance is surprising. In practicing the subject methods, an effective amount of at least one oxysterol active agent compound selected from 25-hydroxycholesterol-3-sulfate (25HC3S), 25-hydroxy-cholesterol-disulfate (25HCDS), 27-hydroxycholesterol-3-sulfate (27HC3S), 27-hydroxycholesterol-disulfate (27HCDS), 24-hydroxycholesterol-3-sulfate (24HC3S), 24-hydroxycholesterol-disulfate (24HCDS), and 24,25-epoxycholesterol-3-sulfate, or salt thereof is administered to the subject.

Aspects of the disclosure include:

1. A method of treating insulin resistance in a human subject in need thereof, the method comprising orally administering to the subject at least one compound selected from 25-hydroxycholesterol-3-sulfate (25HC3S), 25-hydroxycholesterol-disulfate (25HCDS), 27-hydroxycholesterol-3-sulfate (27HC3S), 27-hydroxycholesterol-disulfate (27HCDS), 24-hydroxycholesterol-3-sulfate (24HC3S), 24-hydroxycholesterol-disulfate (24HCDS), and 24,25-epoxycholesterol-3-sulfate, or salt thereof in an amount ranging from 1 mg/day to 300 mg/day.

2. A method of treating insulin resistance in a human subject in need thereof, the method comprising orally administering to the subject at least one compound selected from 25-hydroxycholesterol-3-sulfate (25HC3S), 25-hydroxycholesterol-disulfate (25HCDS), 27-hydroxycholesterol-3-sulfate (27HC3S), 27-hydroxycholesterol-disulfate (27HCDS), 24-hydroxycholesterol-3-sulfate (24HC3S), 24-hydroxycholesterol-disulfate (24HCDS), and 24,25-epoxycholesterol-3-sulfate, or salt thereof in an amount ranging from 1 mg/day to 100 mg/day.

3. The method of aspect 1 or 2, wherein the human subject has non-alcoholic steatohepatitis (NASH).

4. A method of treating insulin insufficiency in a human subject in need thereof, the method comprising orally administering to the subject at least one compound selected from 25-hydroxycholesterol-3-sulfate (25HC3S), 25-hydroxycholesterol-disulfate (25HCDS), 27-hydroxycholesterol-3-sulfate (27HC3S), 27-hydroxycholesterol-disulfate (27HCDS), 24-hydroxycholesterol-3-sulfate (24HC3S), 24-hydroxycholesterol-disulfate (24HCDS), and 24,25-epoxycholesterol-3-sulfate, or salt thereof in an amount ranging from 1 mg/day to 300 mg/day.

5. A method of treating insulin insufficiency in a human subject in need thereof, the method comprising orally administering to the subject at least one compound selected from 25-hydroxycholesterol-3-sulfate (25HC3S), 25-hydroxycholesterol-disulfate (25HCDS), 27-hydroxycholesterol-3-sulfate (27HC3S), 27-hydroxycholesterol-disulfate (27HCDS), 24-hydroxycholesterol-3-sulfate (24HC3S), 24-hydroxycholesterol-disulfate (24HCDS), and 24,25-epoxycholesterol-3-sulfate, or salt thereof in an amount ranging from 1 mg/day to 100 mg/day.

6. The method of aspect 4 or 5, wherein the human subject has non-alcoholic steatohepatitis (NASH).

7. A method of treating diabetes in a human subject in need thereof, the method comprising orally administering to the subject at least one compound selected from 25-hydroxycholesterol-3-sulfate (25HC3S), 25-hydroxycholesterol-disulfate (25HCDS), 27-hydroxycholesterol-3-sulfate (27HC3S), 27-hydroxycholesterol-disulfate (27HCDS), 24-hydroxycholesterol-3-sulfate (24HC3S), 24-hydroxycholesterol-disulfate (24HCDS), and 24,25-epoxycholesterol-3-sulfate, or salt thereof in an amount ranging from 1 mg/day to 300 mg/day.

8. A method of treating diabetes in a human subject in need thereof, the method comprising orally administering to the subject at least one compound selected from 25-hydroxycholesterol-3-sulfate (25HC3S), 25-hydroxycholesterol-disulfate (25HCDS), 27-hydroxycholesterol-3-sulfate (27HC3S), 27-hydroxycholesterol-disulfate (27HCDS), 24-hydroxycholesterol-3-sulfate (24HC3S), 24-hydroxycholesterol-disulfate (24HCDS), and 24,25-epoxycholesterol-3-sulfate, or salt thereof in an amount ranging from 1 mg/day to 100 mg/day.

9. The method of aspect 7 or 8, wherein the human subject has non-alcoholic steatohepatitis (NASH).

10. The method of aspect 7 or 8, wherein the diabetes is type I diabetes.

11. The method of aspect 7 or 8, wherein the diabetes is type II diabetes.

12. A method of treating prediabetes in a human subject in need thereof, the method comprising orally administering to the subject at least one compound selected from 25-hydroxycholesterol-3-sulfate (25HC3S), 25-hydroxycholesterol-disulfate (25HCDS), 27-hydroxycholesterol-3-sulfate (27HC3S), 27-hydroxycholesterol-disulfate (27HCDS), 24-hydroxycholesterol-3-sulfate (24HC3S), 24-hydroxycholesterol-disulfate (24HCDS), and 24,25-epoxycholesterol-3-sulfate, or salt thereof in an amount ranging from 1 mg/day to 300 mg/day.

13. A method of treating prediabetes in a human subject in need thereof, the method comprising orally administering to the subject at least one compound selected from 25-hydroxycholesterol-3-sulfate (25HC3S), 25-hydroxycholesterol-disulfate (25HCDS), 27-hydroxycholesterol-3-sulfate (27HC3S), 27-hydroxycholesterol-disulfate (27HCDS), 24-hydroxycholesterol-3-sulfate (24HC3S), 24-hydroxycholesterol-disulfate (24HCDS), and 24,25-epoxycholesterol-3-sulfate, or salt thereof in an amount ranging from 1 mg/day to 100 mg/day.

14. The method of aspect 12 or 13, wherein the human subject has non-alcoholic steatohepatitis (NASH).

15. A method of treating non-alcoholic steatohepatitis (NASH) and at least one of insulin resistance, diabetes and prediabetes, in a human subject in need thereof, the method comprising orally administering to the subject at least one compound selected from 25-hydroxycholesterol-3-sulfate (25HC3S), 25-hydroxycholesterol-disulfate (25HCDS), 27-hydroxycholesterol-3-sulfate (27HC3S), 27-hydroxycholesterol-disulfate (27HCDS), 24-hydroxycholesterol-3-sulfate (24HC3S), 24-hydroxycholesterol-disulfate (24HCDS), and 24,25-epoxycholesterol-3-sulfate, or salt thereof in an effective amount.

16. The method of any one of aspects 1, 3, 4, 6, 7, 9 to 12, 14 and 15, wherein the orally administering comprises orally administering the at least one compound in an amount ranging from 5 mg/day to 200 mg/day.

17. The method of any one of aspects 1 to 16, wherein the orally administering comprises orally administering the at least one compound in an amount ranging from 5 mg/day to 90 mg/day.

18. The method of any one of aspects 1 to 16, wherein the orally administering comprises orally administering the at least one compound in an amount ranging from 10 mg/day to 80 mg/day.

19. The method according to any one of aspects 1 to 16, wherein the orally administering comprises orally administering the at least one compound in an amount ranging from 30 mg/day to 70 mg/day.

20. The method of any one of aspects 1 to 19, wherein a total amount per kg of the at least one compound that is orally administered to the subject ranges from 0.1 mg/kg/day to 10 mg/kg/day.

21. The method of any one of aspects 1 to 19, wherein a total amount per kg of the at least one compound that is orally administered to the subject ranges from 0.1 mg/kg/day to 5 mg/kg/day.

22. The method of aspect 21, wherein the total amount per kg ranges from 0.2 mg/kg/day to 4 mg/kg/day.

23. The method of aspect 21, wherein the total amount per kg ranges from 0.3 mg/kg/day to 3 mg/kg/day.

24. The method of aspect 21, wherein the total amount per kg ranges from 0.4 mg/kg/day to 2 mg/kg/day.

25. The method of any one of aspects 1 to 24, wherein the orally administering comprises orally administering a plurality of doses of the at least one compound.

26. The method of aspect 25, wherein the doses are orally administered at a frequency ranging from once weekly to three times a day.

27. The method of aspect 25, wherein the doses are orally administered once a day.

28. The method of aspect 25, wherein the doses are orally administered twice a day.

29. The method of any one of aspects 25 to 28, wherein the orally administering comprises orally administering for a dosing period of at least 7 days, such as at least 14 days, at least 28 days, at least 3 months, at least 6 months, or at least 1 year.

30. The method of any one of aspects 1 to 29, wherein the at least one compound is orally administered in a formulation comprising the at least one compound and a pharmaceutically acceptable carrier.

31. The method of any one of aspects 1 to 30, wherein the at least one compound comprises a salt, such as a salt of 25HC3S.

32. The method of aspect 31, wherein the salt is sodium salt.

33. The method of any one of aspects 1 to 32, wherein the human subject has a magnetic resonance imaging-proton density fat fraction (MRI-PDFF) prior to treatment of at least 5%.

34. The method of any one of aspects 1 to 33, wherein the human subject has a magnetic resonance elastography (MRE) prior to treatment $\geq 2.75$ kPa.

35. The method of any one of aspects 1 to 34, wherein the subject exhibits a half-life time of the at least one compound in the plasma after administration ($T_{1/2}$) ranging from about 1 hour to about 5 hours or from about 1.5 hour to about 4 hours.

36. The method of any one of aspects 1 to 35, wherein the subject exhibits a Cmax of the at least one compound ranging from about 25 ng/mL to about 4000 ng/mL, about 25 ng/mL to about 200 ng/mL, from about 50 ng/mL to about 150 ng/mL, from about 75 ng/mL to about 125 ng/mL, from about 300 ng/mL to about 1500 ng/mL, from about 400 ng/mL to about 1250 ng/mL, or from about 500 ng/mL to about 1000 ng/mL.

37. The method of any one of aspects 1 to 36, wherein the subject exhibits a Cmax of the at least one compound ranging from about 100 ng/mL to about 300 ng/mL, from about 120 ng/mL to about 250 ng/mL, from about 150 ng/mL to about 200 ng/mL, from about 100 ng/mL to about 300 ng/mL, from about 120 ng/mL to about 250 ng/mL, or from about 150 ng/mL to about 200 ng/mL, per 100 mg of orally administered at least one compound.

38. The method of any one of aspects 1 to 37, wherein the subject exhibits an AUCinf of the at least one compound ranging from about 300 ng*h/mL to about 1000 ng*h/mL, about 400 ng*h/mL to about 900 ng*h/mL, from about 500 ng*h/mL to about 800 ng*h/mL, about 2700 ng*h/mL to about 9000 ng*h/mL, about 3000 ng*h/mL to about 8000 ng*h/mL, or from about 3500 ng*h/mL to about 7000 ng*h/mL.

39. The method of any one of aspects 1 to 38, wherein the subject exhibits an AUCinf of the at least one compound ranging from about 600 ng*h/mL to about 1000 ng*h/mL, about 700 ng*h/mL to about 900 ng*h/mL, or from about 800 ng*h/mL to about 900 ng*h/mL, per 100 mg of orally administered at least one compound.

40. The method of any one of aspects 1 to 39, wherein the subject exhibits an apparent volume of distribution (Vz/F) of the at least one compound ranging from about 300 L to about 1000 L, about 400 L to about 900 L, or from about 500 L to about 800 L.

41. The method of any one of aspects 1 to 40, wherein the subject exhibits an apparent clearance (CL/F) of the at least one compound ranging from about 100 L to about 200 L/h, about 110 L/h to about 180 L/h, or from about 120 L/h to about 160 L/h.

42. The method of any one of aspects 1 to 41, wherein the subject is taking a lipid lowering drug, such as at least one of a statin, fenofibrate, omega-3 fatty acid, icosapent ethyl, and fish oil, or further comprising administering a lipid lowering drug, such as at least one of a statin, fenofibrate, omega-3 fatty acid, icosapent ethyl, and fish oil.

43. The method of any one of aspects 1 to 42, wherein the subject is taking at least one of insulin, a glitazone, GLP-1, glucagon, DDP-4 inhibitor, atorvastatin, fluvastatin, lovastatin, pitavastatin, pravastatin, rosuvastatin, and simvastatin, or further comprising administering to the subject at least one of atorvastatin, fluvastatin, lovastatin, pitavastatin, pravastatin, rosuvastatin, and simvastatin.

44. The method of any one of aspects 1 to 43, wherein the human subject has triglycerides>200 mg/dL prior to treatment.

45. At least one compound selected from 25-hydroxycholesterol-3-sulfate (25HC3S), 25-hydroxycholesterol-disulfate (25HCDS), 27-hydroxycholesterol-3-sulfate (27HC3S), 27-hydroxycholesterol-disulfate (27H-CDS), 24-hydroxycholesterol-3-sulfate (24HC3S), 24-hydroxycholesterol-disulfate (24HCDS), and 24,25-epoxycholesterol-3-sulfate, or salt thereof for use in a method of treating at least one of insulin resistance, diabetes, prediabetes, and non-alcoholic steatohepatitis (NASH) in a human subject in need thereof, wherein the method is as defined in any one of aspects 1 to 44.

46. At least one compound selected from 25-hydroxycholesterol-3-sulfate (25HC3S), 25-hydroxycholesterol-disulfate (25HCDS), 27-hydroxycholesterol-3-sulfate (27HC3S), 27-hydroxycholesterol-disulfate (27H-CDS), 24-hydroxycholesterol-3-sulfate (24HC3S), 24-hydroxycholesterol-disulfate (24HCDS), and 24,25-epoxycholesterol-3-sulfate, or salt thereof for use in a method of treating at least one of insulin resistance, diabetes, prediabetes, and non-alcoholic steatohepatitis (NASH) in a human subject in need thereof, the human subject having triglycerides>200 mg/dL prior to treatment, wherein the method is as defined in any one of aspects 1 to 44.

47. Use of at least one compound selected from 25-hydroxycholesterol-3-sulfate (25HC3S), 25-hydroxycholesterol-disulfate (25HCDS), 27-hydroxycholesterol-3-sulfate (27HC3S), 27-hydroxycholesterol-disulfate (27HCDS), 24-hydroxycholesterol-3-sulfate (24H-C3S), 24-hydroxycholesterol-disulfate (24HCDS), and 24,25-epoxycholesterol-3-sulfate, or salt thereof in a method for the manufacture of a medicament for use in a method of treating at least one of insulin resistance, diabetes, prediabetes, and non-alcoholic steatohepatitis (NASH) in a human subject in need thereof, wherein the method is as defined in any one of aspects 1 to 44.

48. Use of at least one compound selected from 25-hydroxycholesterol-3-sulfate (25HC3S), 25-hydroxycholesterol-disulfate (25HCDS), 27-hydroxycholesterol-3-sulfate (27HC3S), 27-hydroxycholesterol-disulfate (27HCDS), 24-hydroxycholesterol-3-sulfate (24H-C3S), 24-hydroxycholesterol-disulfate (24HCDS), and 24,25-epoxycholesterol-3-sulfate, or salt thereof in a method for the manufacture of a medicament for use in a method of treating at least one of insulin resistance, diabetes, prediabetes, and non-alcoholic steatohepatitis (NASH) in a human subject in need thereof, the human subject having triglycerides>200 mg/dL prior to treatment, wherein the method is as defined in any one of aspects 1 to 44.

49. At least one compound selected from 25-hydroxycholesterol-3-sulfate (25HC3S), 25-hydroxycholesterol-disulfate (25HCDS), 27-hydroxycholesterol-3-sulfate (27HC3S), 27-hydroxycholesterol-disulfate (27H-CDS), 24-hydroxycholesterol-3-sulfate (24HC3S), 24-hydroxycholesterol-disulfate (24HCDS), and 24,25-epoxycholesterol-3-sulfate, or salt thereof for use in a method of treating at least one of insulin resistance, diabetes, prediabetes, and non-alcoholic steatohepatitis (NASH) in a human subject in need thereof, wherein the human subject is receiving statin therapy.

50. At least one compound selected from 25-hydroxycholesterol-3-sulfate (25HC35), 25-hydroxycholesterol-disulfate (25HCDS), 27-hydroxycholesterol-3-sulfate (27HC3S), 27-hydroxycholesterol-disulfate (27H-CDS), 24-hydroxycholesterol-3-sulfate (24HC3S), 24-hydroxycholesterol-disulfate (24HCDS), and 24,25-epoxycholesterol-3-sulfate, or salt thereof for use according to aspect 49, wherein the statin therapy comprises administration of at least one of atorvastatin, fluvastatin, lovastatin, pitavastatin, pravastatin, rosuvastatin, and simvastatin.

51. At least one compound selected from 25-hydroxycholesterol-3-sulfate (25HC3S), 25-hydroxycholesterol-disulfate (25HCDS), 27-hydroxycholesterol-3-sulfate (27HC3S), 27-hydroxycholesterol-disulfate (27HCDS), 24-hydroxycholesterol-3-sulfate (24HC3S), 24-hydroxycholesterol-disulfate (24HCDS), and 24,25-epoxycholesterol-3-sulfate, or salt thereof for use according to aspect 49 or 50, wherein the method is a method as defined in any one of aspects 1 to 44, and optionally wherein the human subject has triglycerides≥200 mg/dL prior to treatment.

52. At least one compound selected from 25-hydroxycholesterol-3-sulfate (25HC3S), 25-hydroxycholesterol-disulfate (25HCDS), 27-hydroxycholesterol-3-sulfate (27HC3S), 27-hydroxycholesterol-disulfate (27HCDS), 24-hydroxycholesterol-3-sulfate (24HC3S), 24-hydroxycholesterol-disulfate (24HCDS), and 24,25-epoxycholesterol-3-sulfate, or salt thereof for use in a method of treating at least one of insulin resistance, diabetes, prediabetes, and non-alcoholic steatohepatitis (NASH) in a human subject in need thereof by co-administration with at least one statin, optionally wherein the at least one statin comprises at least one of atorvastatin, fluvastatin, lovastatin, pitavastatin, pravastatin, rosuvastatin, and simvastatin.

53. At least one compound selected from 25-hydroxycholesterol-3-sulfate (25HC3S), 25-hydroxycholesterol-disulfate (25HCDS), 27-hydroxycholesterol-3-sulfate (27HC3S), 27-hydroxycholesterol-disulfate (27HCDS), 24-hydroxycholesterol-3-sulfate (24HC3S), 24-hydroxycholesterol-disulfate (24HCDS), and 24,25-epoxycholesterol-3-sulfate, or salt thereof for use according to aspect 52, wherein the human subject is one receiving statin therapy prior to commencing the method, and optionally wherein the statin therapy comprises administration of the same statin or statins that is or are co-administered with the 25HC3S or salt thereof in the method.

54. At least one compound selected from 25-hydroxycholesterol-3-sulfate (25HC3S), 25-hydroxycholesterol-disulfate (25HCDS), 27-hydroxycholesterol-3-sulfate (27HC3S), 27-hydroxycholesterol-disulfate (27HCDS), 24-hydroxycholesterol-3-sulfate (24HC3S), 24-hydroxycholesterol-disulfate (24HCDS), and 24,25-epoxycholesterol-3-sulfate, or salt thereof for use according to aspect 52 or 53, wherein the method is a method as defined in any one of aspects 1 to 44, and optionally wherein the human subject has triglycerides≥200 mg/dL prior to treatment.

55. Use of at least one compound selected from 25-hydroxycholesterol-3-sulfate (25HC3S), 25-hydroxycholesterol-disulfate (25HCDS), 27-hydroxycholesterol-3-sulfate (27HC3S), 27-hydroxycholesterol-disulfate (27HCDS), 24-hydroxycholesterol-3-sulfate (24HC3S), 24-hydroxycholesterol-disulfate (24HCDS), and 24,25-epoxycholesterol-3-sulfate, or salt thereof in a method for the manufacture of a medicament for use in a method of treating at least one of insulin resistance, diabetes, prediabetes, and non-alcoholic steatohepatitis (NASH) in a human subject in need thereof, wherein the human subject is receiving statin therapy.

56. Use according to aspect 55, wherein the statin therapy comprises administration of at least one of atorvastatin, fluvastatin, lovastatin, pitavastatin, pravastatin, rosuvastatin, and simvastatin.

57. Use according to aspect 55 or 56, wherein the method of treating is a method as defined in any one of aspects 1 to 44, and optionally wherein the human subject has triglycerides≥200 mg/dL prior to treatment.

58. Use of at least one compound selected from 25-hydroxycholesterol-3-sulfate (25HC3S), 25-hydroxycholesterol-disulfate (25HCDS), 27-hydroxycholesterol-3-sulfate (27HC3S), 27-hydroxycholesterol-disulfate (27HCDS), 24-hydroxycholesterol-3-sulfate (24HC3S), 24-hydroxycholesterol-disulfate (24HCDS), and 24,25-epoxycholesterol-3-sulfate, or salt thereof in a method for the manufacture of a medicament for use in a method of treating at least one of insulin resistance, diabetes, prediabetes, and non-alcoholic steatohepatitis (NASH) in a human subject in need thereof by co-administration with at least one statin, optionally wherein the at least one statin comprises at least one of atorvastatin, fluvastatin, lovastatin, pitavastatin, pravastatin, rosuvastatin, and simvastatin.

59. Use according to aspect 58, wherein the human subject is one receiving statin therapy prior to commencing the method, and optionally wherein the statin therapy comprises administration of the same statin or statins that is or are co-administered with the 25HC3S or salt thereof in the method.

60. Use according to aspect 58 or 59, wherein the method of treating is a method as defined in any one of aspects 1 to 44, and optionally wherein the human subject has triglycerides≥200 mg/dL prior to treatment.

61. At least one compound selected from 25-hydroxycholesterol-3-sulfate (25HC3S), 25-hydroxycholesterol-disulfate (25HCDS), 27-hydroxycholesterol-3-sulfate (27HC3S), 27-hydroxycholesterol-disulfate (27HCDS), 24-hydroxycholesterol-3-sulfate (24HC3S), 24-hydroxycholesterol-disulfate (24HCDS), and 24,25-epoxycholesterol-3-sulfate, or salt thereof, for use in a method as defined in any one of aspects 1 to 44.

62. Use of at least one compound selected from 25-hydroxycholesterol-3-sulfate (25HC3S), 25-hydroxycholesterol-disulfate (25HCDS), 27-hydroxycholesterol-3-sulfate (27HC3S), 27-hydroxycholesterol-disulfate (27HCDS), 24-hydroxycholesterol-3-sulfate (24HC3S), 24-hydroxycholesterol-disulfate (24HCDS), and 24,25-epoxycholesterol-3-sulfate, or salt thereof, in a method for the manufacture of a medicament for use in a method as defined in any one of aspects 1 to 44.

BRIEF DESCRIPTION OF THE DRAWINGS

Figure 2:
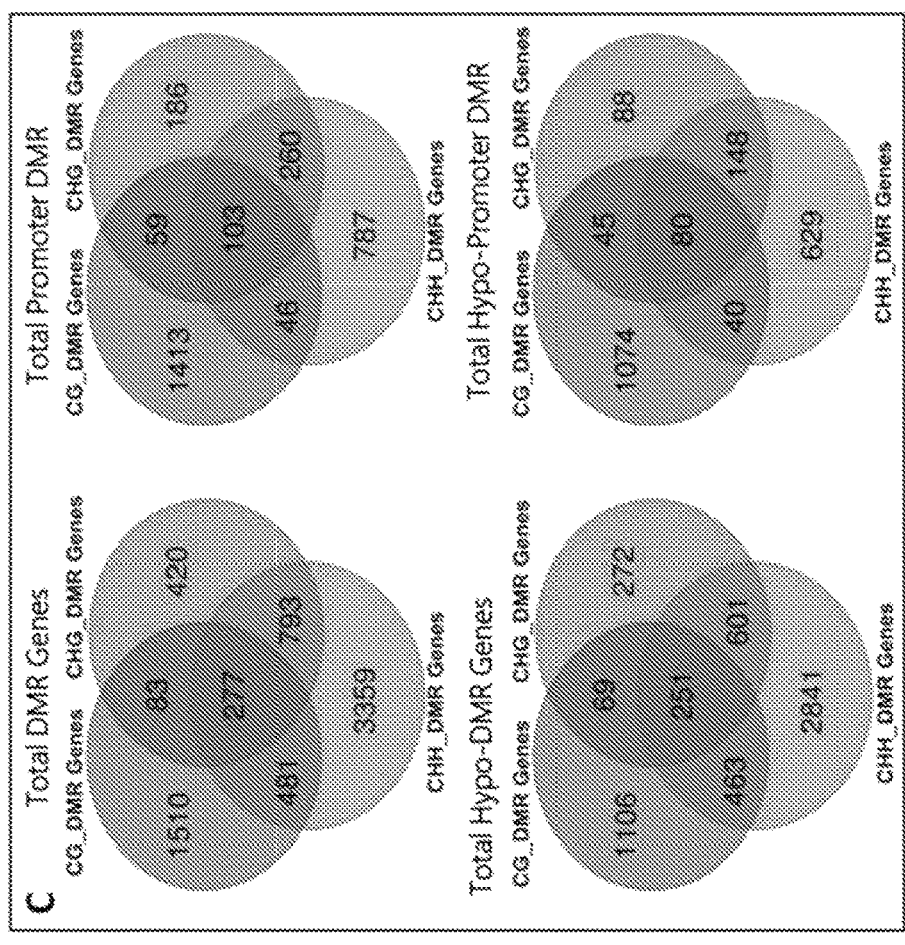
Figure 2:
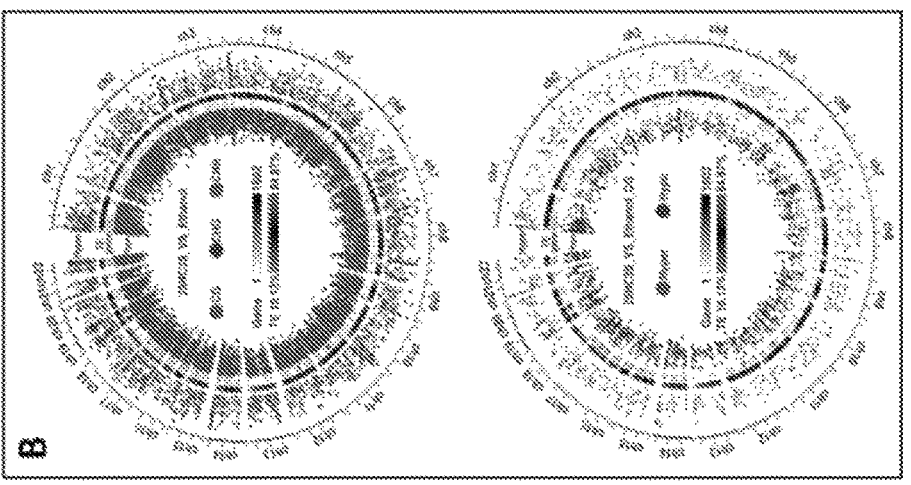
Figure 2:
Figure 2:
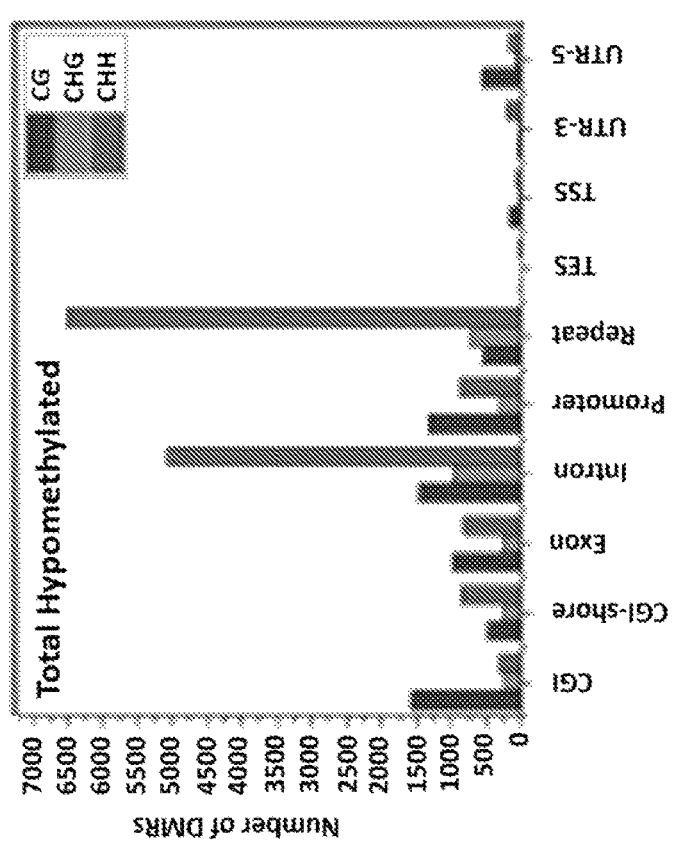
Figure 2:
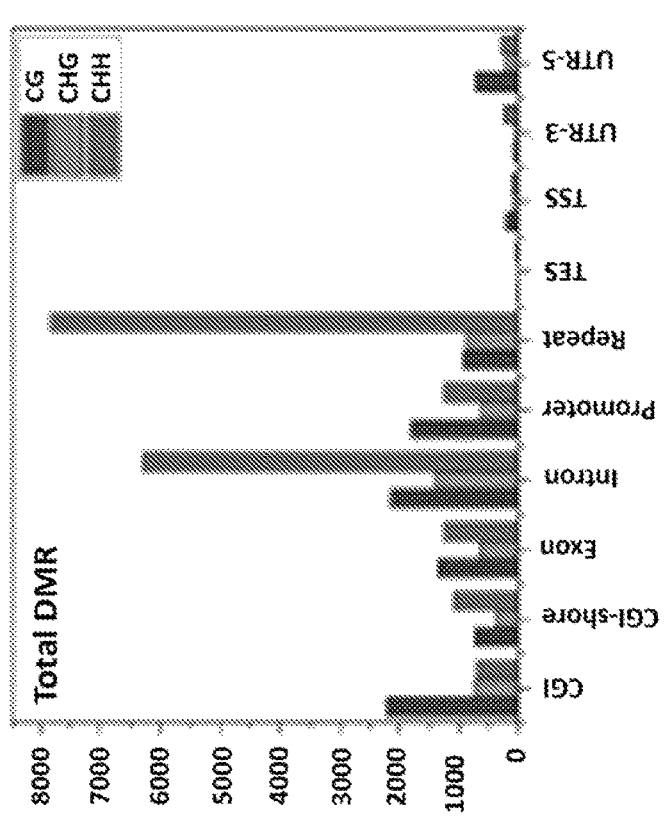
Figure 2:
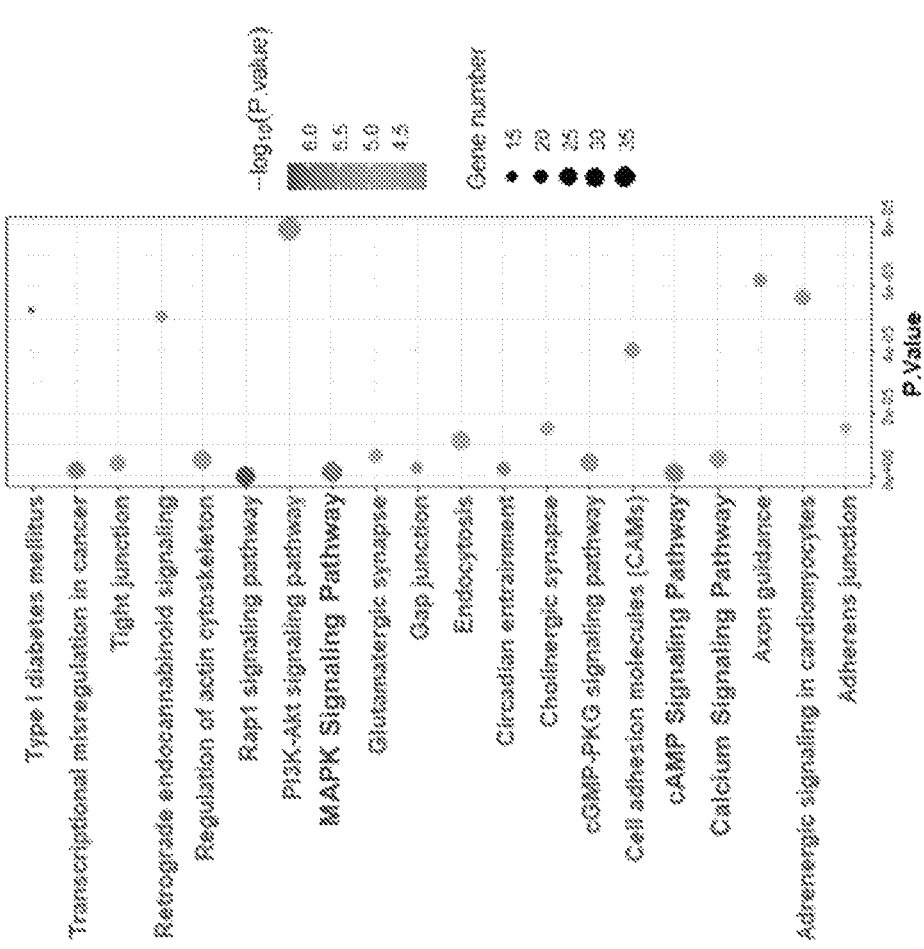
Figure 2:
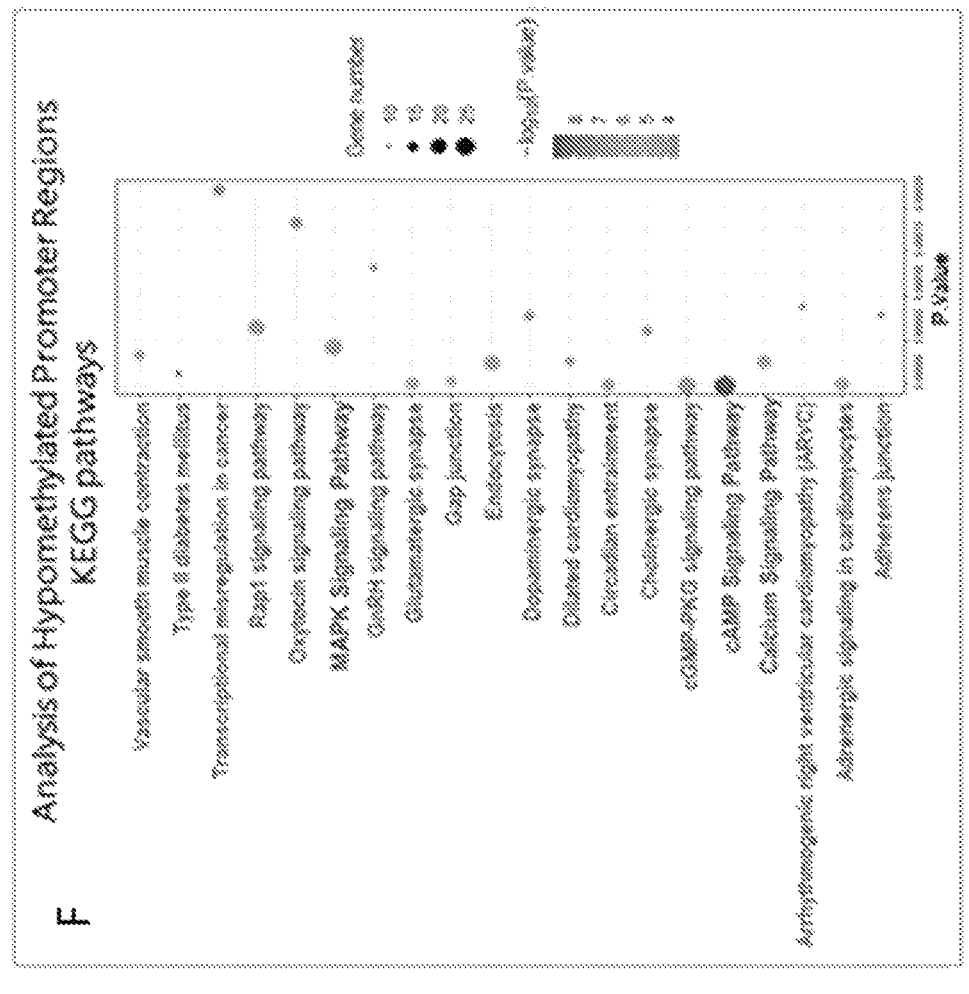

FIGS. 2A-2F. Effects of 25HC3S on DNA methylation in hepatocytes by global methylation sequencing analysis. Huh-7 cells were cultured in HG media for 72 hours and treated with ethanol (vehicle) and 25 mM 25HC3S in ethanol for 4 hours. The levels of global methylation were estimated by LINE-1 assay. Four CpG sites in promoter regions of LINE-1 element were chosen as the target positions as shown in FIG. 2A. Detailed global methylation was measured by WGBS. Circos maps of DMR distribution in chromosomes is shown in FIG. 2B: the first circle shows the distribution of hypermethylation DMRs; the second shows transposable element (TE) density; and the third shows the distribution of hypomethylation DMRs. Venn diagrams of hypomethylated DMR-associated genes (DMGs) in 25HC3S and Vehicle libraries under CG, CHG, and CHH contexts of whole genome (Up) and promoter regions (Low) are shown in FIG. 2C. KOBAS software was used to test the statistical enrichment of DMR related genes in the Kyoto Encyclopedia of Genes and Genomes (KEGG) pathways. DNA methylation levels in different genomic functional regions of the whole genome in FIG. 2D, where the x-axis represents the different genomic regions (CGI, CGI-shore, promoter, UTR 5, exon, intron, UTR 3, and repeat), and the y-axis represents the methylation levels in 25HC3S and vehicle libraries under CG, CHG, and CHH contexts. High enrichment of hypomethylated DMRs in whole genome in KEGG pathways is shown in FIG. 2E. High enrichment of hypomethylated DMRs in promoter regions in KEGG pathways is shown in FIG. 2F. The detailed KEGG pathways are shown in Table 1.3.

FIGS. 3A-3D. Expression of key genes related to signaling pathways. Huh-7 cells were cultured in HG media for 72 hours and treated with 25HC3S at 6.25 µM, 12.5 µM, 25 µM, and 50 µM for 1 hour, 2 hours, 4 hours, 6 hours, and 8 hours. Key Genes and their targeting genes expression were determined by RT-PCR analysis. The expressions of DUSP8 (Dual Specificity Phosphatases 8), DUSP7 (Dual Specificity Phosphatases 7), and MAPK1 (Mitogen-activated protein kinase 1) in MAPK signaling pathway are shown in FIG. 3A; their target genes, CREB (cAMP responsive element binding protein), PRDX6 (peroxiredoxin 6), and BAD (BCL2 Associated Agonist Of Cell Death) are shown in FIG. 3B; Key genes, CACNA family (calcium voltage-gated channel subunits), in calcium-AMK pathway are shown in FIG. 3C; their targeting genes PGC1A (PPARG co-activator 1 alpha), HMGR (3-hydroxy-3-methylglutaryl-CoA reductase), and FAS (fatty acid synthase) are shown in FIG. 3D.

FIGS. 4A-4F. Effect of 25HC3S on transcription levels in hepatocytes. HepG-2 cells were cultured in HG media and treated with 25 µM of 25HC3S for 2 hours, 4 hours, and 8 hours. The up-regulated genes (>1.6 fold) are shown in FIG. 4A. Enrichment of up-regulated genes (8 hours) to Gene ontological (GO) groups are shown in FIG. 4B (NRAP: negative regulation of apoptotic process; NRPCD: negative regulation of programmed cell death; RS: regulation of signaling; SP: regulation of phosphorylation; NRCD negative regulation of cell death; RES: response to stress; NRPP: negative regulation of protein phosphorylation; CRCS: cellular response to chemical stimulus; NRP: negative regulation of phosphorylation; ST: signal transduction). Down-regulated genes (reduction>40%) are shown in FIG. 4C. Enrichment of down-regulated genes (8 hours) to GO groups are shown in FIG. 4D (CLMP: cellular lipid metabolic process; SBP: steroid biosynthetic process; AMP: alcohol metabolic process; CMP: cholesterol metabolic process; FAMP: fatty acid metabolic process; TBP: triglyceride biosynthetic process; NLBP: neutral lipid biosynthetic process; ACMP: acyl-CoA metabolic process; OABP: organic acid biosynthetic process; BAMP: bile acid metabolic process). Heatmap of up-regulated genes related to this study is shown in FIG. 4E; down-regulated genes are shown in FIG. 4F.

Figure 5:
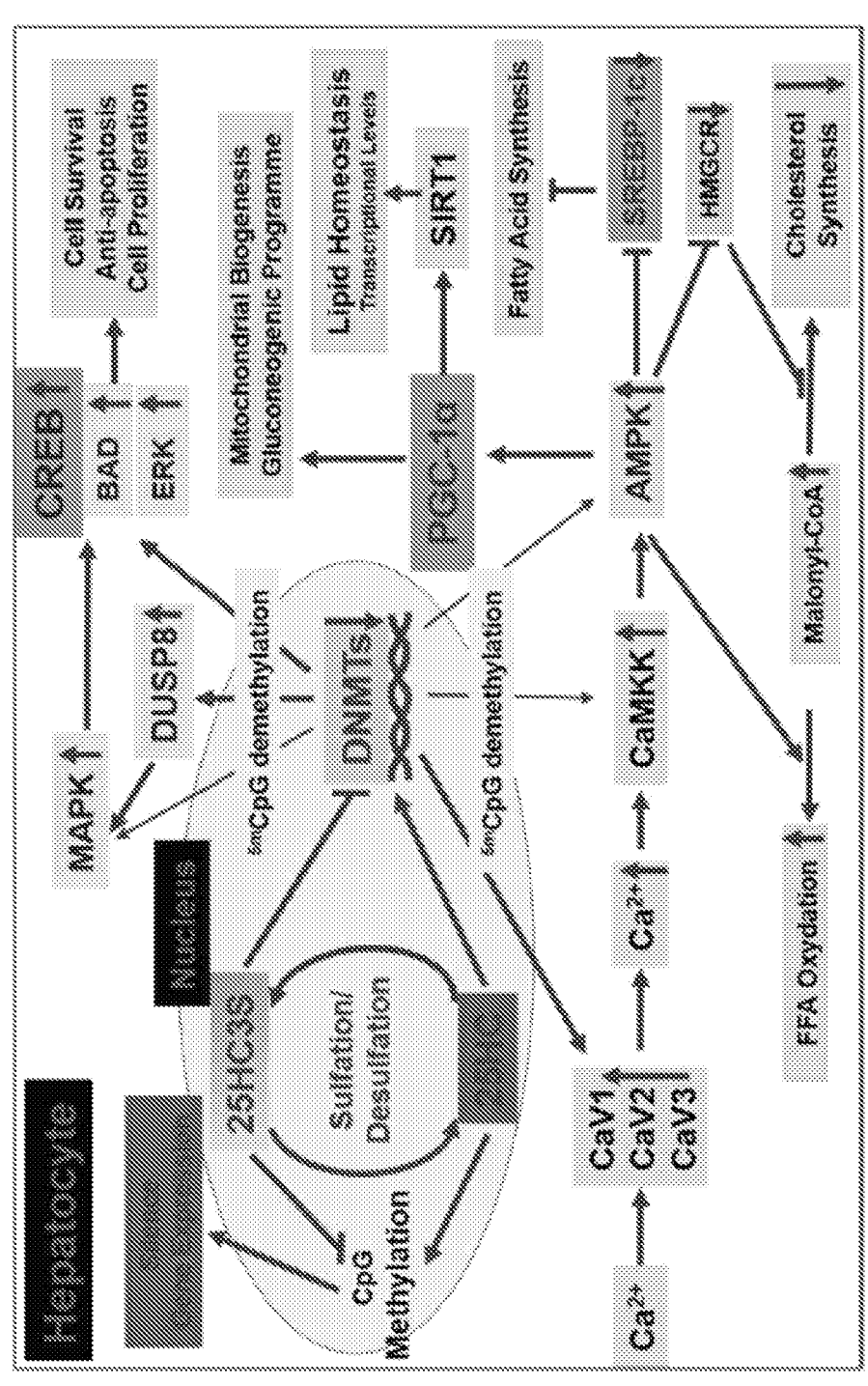

FIG. 5. Sulfation of 25HC as an epigenetic regulatory pathway. 25HC is an endogenous agonist of DNMT-1 that methylates CpG in promoter regions and subsequently silences gene expression, resulting in cell death and lipogenesis. 25HC can be sulfated to 25HC3S, which acts as an endogenous ligand and inhibits activities of DNMTs. 25HC3S demethylates $^{5m}$CpG in promoter regions, and successively increases gene expression. The eminent pathways regulated by the sulfation of oxysterol are involved in energy and lipids metabolisms, MAPK-ERK, and calcium-AMPK. 25HC3S significantly increases Dual-specificity phosphatases (DUSPs) and CREB expression, which activate MAPK/ERK pathway, including CREB, BAD, and ERK, and subsequently regulate cell survival and death. 25HC3S decreases lipid biosynthesis and reduces lipid accumulation by demethylating $^{5m}$CpG in promoter regions, increasing expression of key genes involved in calcium channels and AMPK, and activating corresponding signaling pathways, which result in increased oxidation of free fatty acids (FFA), and decreased biosynthesis of cholesterol and FFA. The global regulation by sulfation of oxysterol suggests the physiological and pathophysiological significance of this regulatory mechanism.

Figure 6:
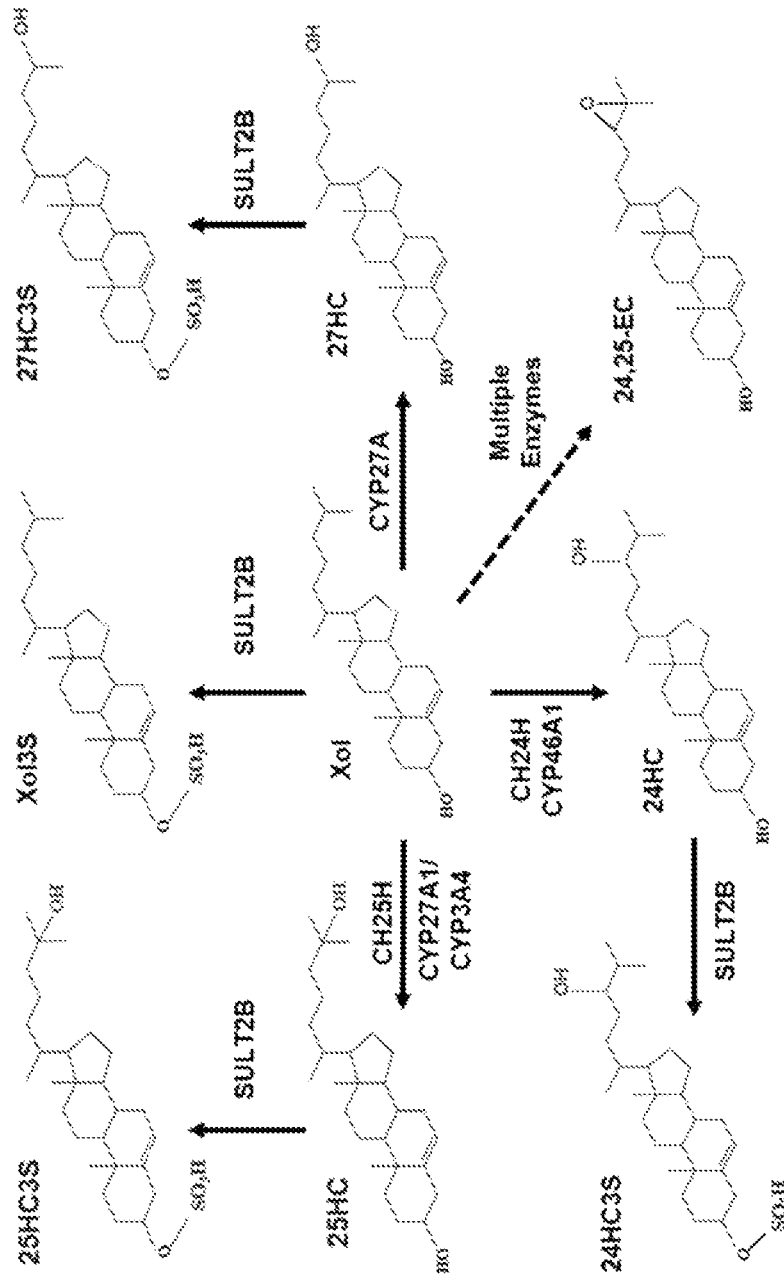

FIG. 6. Mechanisms of sulfation and metabolic pathways of oxysterol sulfates.

Figure 7:
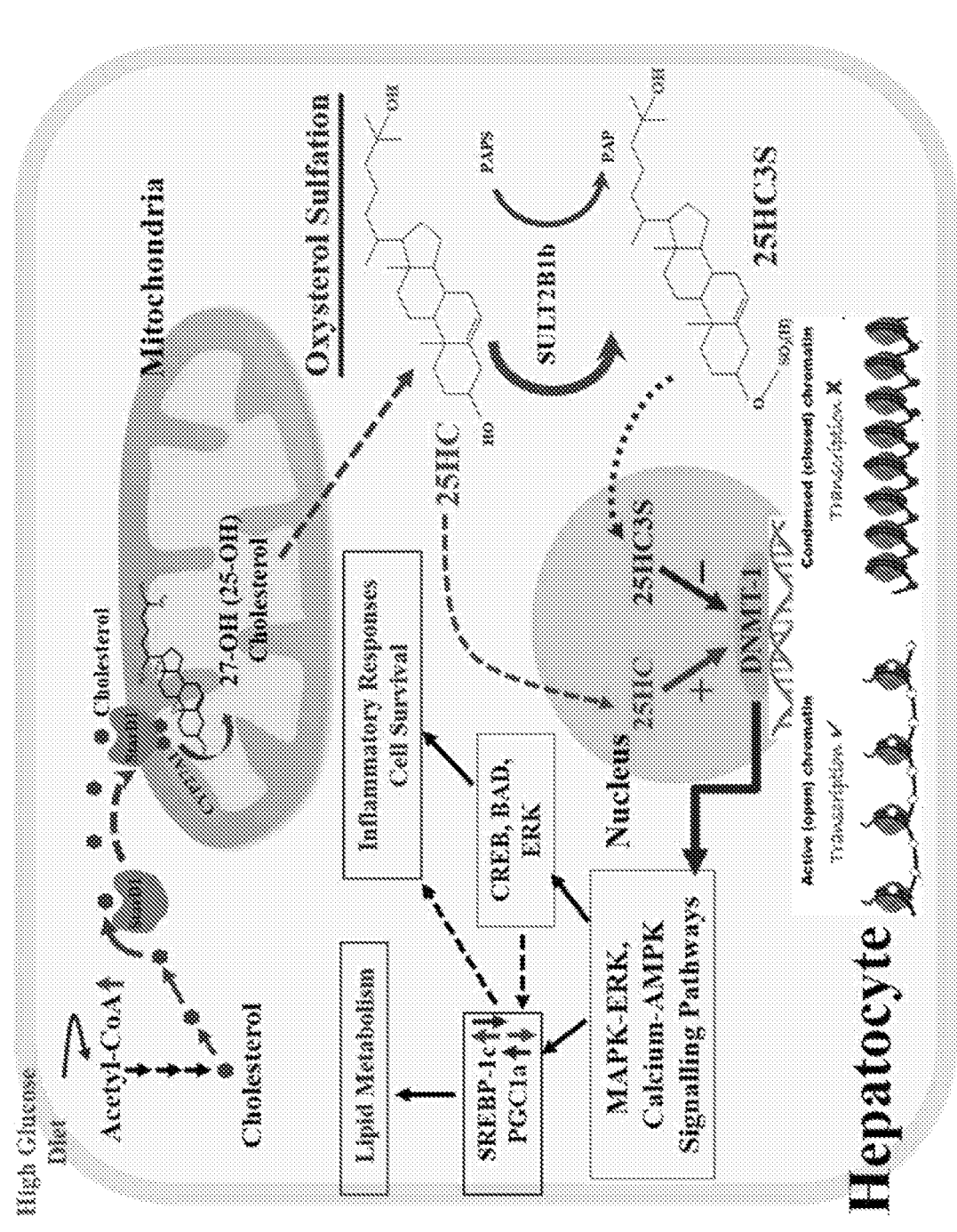

FIG. 7. Regulatory pathway of oxysterol sulfation.

Figure 8:
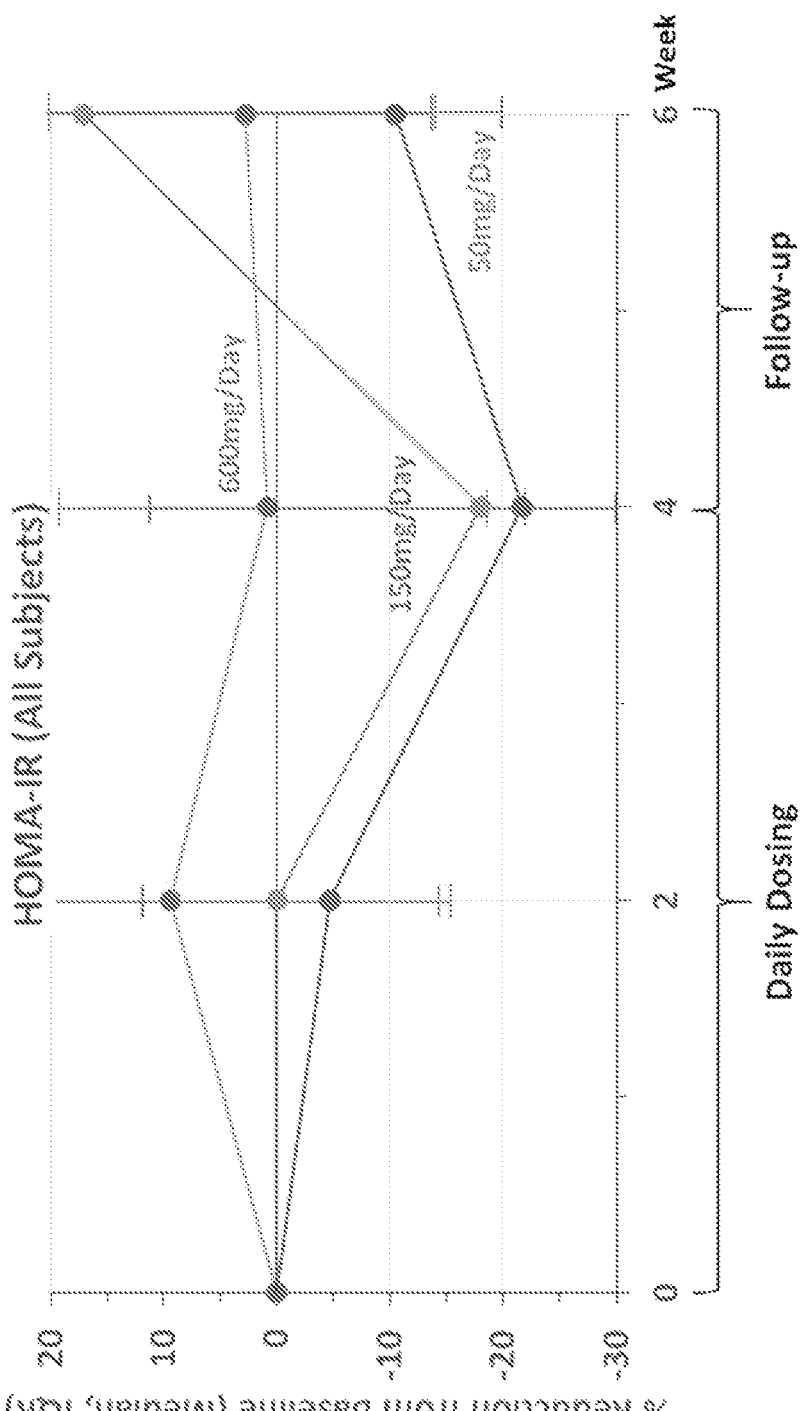

FIG. 8. Insulin resistance. The Homeostatic Model Assessment for Insulin Resistance shows percentage reduction from baseline in insulin resistance exhibited by subjects dosed daily for 4 weeks with 50 mg/day, 150 mg/day and 600 mg/day of 25-hydroxycholesterol-3-sulfate. The insulin resistance exhibited at 6-week follow up is also shown.

Figure 9:
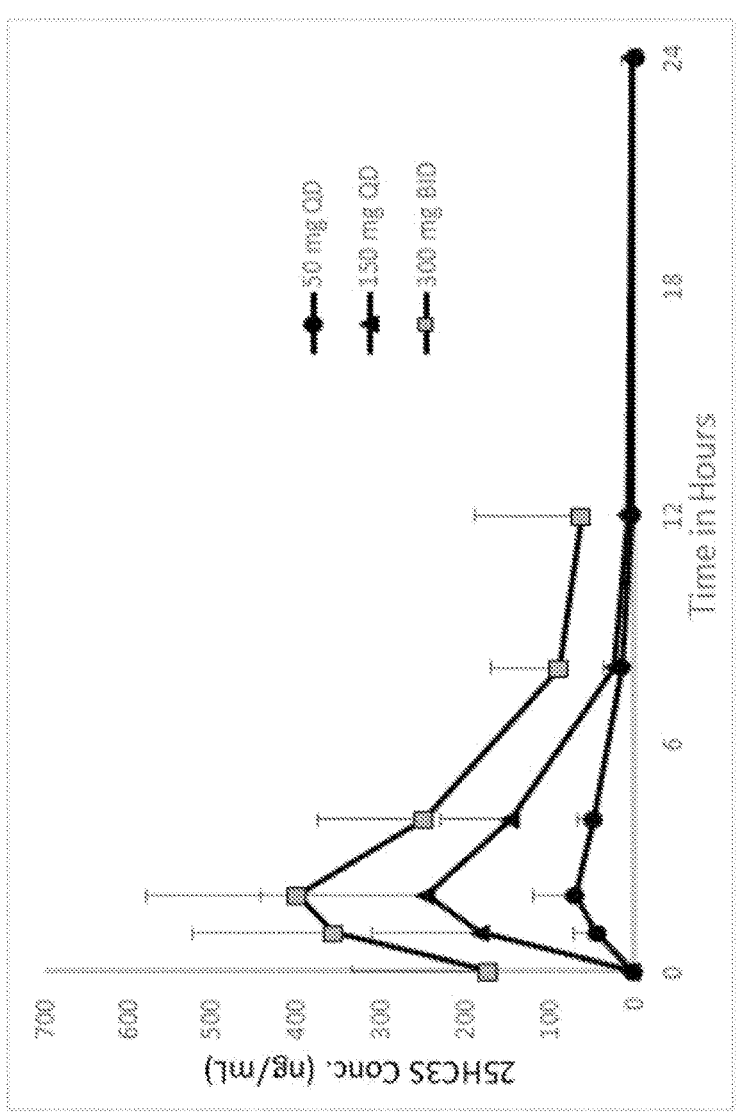

FIG. 9. depicts the mean pharmacokinetic (PK) parameters of subjects administered 25HC3S according to certain embodiments.

DETAILED DESCRIPTION OF THE INVENTION

The present disclosure provides methods for treating at least one of insulin resistance, diabetes, and prediabetes, and, optionally, also treating non-alcoholic steatohepatitis (NASH).

In practicing the subject methods, one or more oxysterol active agent compound selected from 25-hydroxycholesterol-3-sulfate (25HC3S), 25-hydroxycholesterol-disulfate (25HCDS), 27-hydroxycholesterol-3-sulfate (27HC3S), 27-hydroxycholesterol-disulfate (27HCDS), 24-hydroxycholesterol-3-sulfate (24HC3S), 24-hydroxycholesterol-disulfate (24HCDS), and 24,25-epoxycholesterol-3-sulfate (24,25-EC3S), or salt thereof is administered to a subject (e.g., human subject). As described herein, the compound 25-hydroxycholesterol-3-sulfate (25HC3S) refers to a compound having the chemical structure:

25HC3S

The compound 25-hydroxycholesterol-disulfate (25HCDS) refers to a compound having the chemical structure:

25HCDS

The compound 27-hydroxycholesterol-3-sulfate (27HC3S) refers to a compound having the chemical structure:

27HC3S

The compound 27-hydroxycholesterol-disulfate (27HCDS) refers to a compound having the chemical structure:

27HCDS

The compound 24-hydroxycholesterol-3-sulfate (24HC3S) refers to a compound having the chemical structure:

24HC3S

The compound 24-hydroxycholesterol-disulfate (24HCDS) refers to a compound having the chemical structure:

24HCDS

The compound 24,25-epoxycholesterol-3-sulfate (24,25-EC3S) refers to a compound having the chemical structure:

24,25-EC3S

Oxysterols according to certain instances, can be sulfated by sulfotransferase 2B1b (SULT2Bib) at the 3-position of the ring A of cholesterol to be oxysterol 3-sulfates including 25HC3S, 24HC3S, 27HC3S as well as Xol3S (cholesterol 3-sulfate) as summarized in FIG. 6. The oxysterol sulfate can be further sulfated by sulfotransferase 2A1 (SULT2A1)

to be oxysterol disulfates. For example, 25-hydroxycholesterol 3-sulfate (25HC3S) can be further sulfated by SULT2A1 to 5-cholesten-30, 25-diol-disulfate (25HCDS). 25HC3S and 25HCDS are the only oxysterol sulfates that have been identified in vivo in hepatocyte nuclei while 27HC3S in human sera and 24HC3S in urine. 25HC3S and 25HCDS are also potent regulators but function in a different direction from their precursor 25HC.

Cholesterol can be hydroxylated by CYP27A1 to 25HC or 27HC in the mitochondria, and hydroxylated to 25HC by CYP3A4, or by cholesterol 25-hydroxylase (CH25HL) in endoplasmic reticulum. Cholesterol can also be hydroxylated by cholesterol 24-hydroxylase to 24HC in brain tissue. This cholesterol precursor can also be used for synthesis of desmosterol via a shunt of the mevalonate pathway. The desmosterol can be oxygenated by CYP46A1 to form 24,25-epoxycholesterol (24,25EC). 25HC, 27HC, 24HC, and cholesterol can be subsequently sulfated at the 3β-position by SULT2B1b to form 25HC3S, 27HC3S, 24HC3S, and Xol3S, respectively. 24,25EC can be sulfated to be 24,25EC3S.

While not being bound by theory, the function of 25HC and 25HC3S in global regulation indicates that they are epigenetic regulators. Methylation at position 5 of cytosine (5-methylcytosine, $^{5m}$C) in DNA promoter regions is an important epigenetic modification that regulates gene expression and other functions of the genome. Cytosine methylation of CpG in promoter regions is inversely correlated with transcriptional activity of associated genes as it causes chromatin condensation and gene silencing. Dysregulation of CpG methylation and gene expression affect metabolism, tissue function, and the metabolic state. Cytosine methylation is catalyzed by DNA methyltransferases (DNMT-1, 3a/3b), which in some cases play a role in the regulation of DNA methylation/demethylation. 25HC and 25HC3S are ligands of DNA methyltranferase-1 (DNMT-1). In some cases, the oxysterol active agent compounds described herein are cellular regulatory molecules that epigenetically regulate lipid metabolism, cell survival/death, and inflammatory responses via DNA CpG methylation and $^{5m}$CpG demethylation. In some cases, high glucose incubation increases CpG methylation in promoter regions via increasing nuclear 25HC levels, which silences key gene expressions involved in PI3K-Akt, cAMP, NAFLD, Type II Diabetes Mellitus, and Insulin Secretion signaling pathways. In certain cases, oxysterol active agent compounds disclosed herein (e.g., 25HC3S) de-methylates $^{5m}$CpG in these promoter regions, increases gene expression, and up-regulates these signaling pathways. In some cases, the oxysterol active agent compound regulates the signaling pathways in an opposite direction from precursor 25HC. In some cases, the one or more oxysterol active agent compounds regulate cell signaling pathways in response to stress responses. In certain cases, the one or more oxysterol active agent compounds affect protein phosphorylation, inositol phosphorylation, and sphingosine phosphorylation in regulating cellular functions. In certain cases, the one or more oxysterol active agent compounds regulate gene expression at transcriptional levels. An illustrative mechanism is depicted in FIG. 7. The one or more oxysterol active agent compounds (e.g., 25HC3S) in certain cases decrease lipid accumulation, anti-inflammatory response, and anti-apoptosis by increasing gene expression through demethylation of $^{5m}$CpG in promoter regions of the key genes involved in MAPK-ERK and Calcium-AMPK signaling pathways, such as CREB5 (CAMP Responsive Element Binding Protein 5), BAD (BCL2 Associated Agonist of Cell Death), and ERK (Mitogen-activated protein kinase 1).

In some cases, the term "treat" is used herein to refer to administering at least one oxysterol active agent compound selected from 25-hydroxycholesterol-3-sulfate (25HC3S), 25-hydroxycholesterol-disulfate (25HCDS), 27-hydroxycholesterol-3-sulfate (27HC3S), 27-hydroxycholesterol-disulfate (27HCDS), 24-hydroxycholesterol-3-sulfate (24HC3S), 24-hydroxycholesterol-disulfate (24HCDS), and 24,25-epoxycholesterol-3-sulfate, or salt thereof to a human subject that: (1) already exhibits at least one symptom of insulin resistance, diabetes, or prediabetes, and, optionally, also non-alcoholic steatohepatitis (NASH); and/or (2) is diagnosed as having insulin resistance, diabetes, or prediabetes, and, optionally, also non-alcoholic steatohepatitis (NASH) In some cases, "treatment" involves the lessening or attenuation, or in some instances, the complete eradication, of at least one symptom of insulin resistance, diabetes, or prediabetes, and, optionally, also non-alcoholic steatohepatitis (NASH) that was present prior to or at the time of administration of the at least one oxysterol active agent compound selected from 25-hydroxycholesterol-3-sulfate (25HC3S), 25-hydroxycholesterol-disulfate (25HCDS), 27-hydroxycholesterol-3-sulfate (27HC3S), 27-hydroxycholesterol-disulfate (27HCDS), 24-hydroxycholesterol-3-sulfate (24HC3S), 24-hydroxycholesterol-disulfate (24HCDS), and 24,25-epoxycholesterol-3-sulfate, or salt thereof. In some cases, treatment according to the present disclosure is sufficient to improve clinical indicators in the subject. In certain instances, the improvement in the clinical indicators in the subject is such that the subject is considered to no longer have insulin resistance, diabetes, or prediabetes, and, optionally, also no longer has non-alcoholic steatohepatitis (NASH).

In some cases, the subject is a subject that exhibits at least one symptom of having Type 1 diabetes. In some cases, the subject is diagnosed as having Type 1 diabetes. In some cases, the subject is a subject that exhibits at least one symptom of having Type 2 diabetes. In some cases, the subject is diagnosed as having Type 2 diabetes. In some cases, the subject is a subject that exhibits at least one symptom of having gestational diabetes. In some cases, the subject is diagnosed as having gestational diabetes. In some cases, the subject is a subject that exhibits at least one symptom of having prediabetes. In some cases, the subject is diagnosed as having prediabetes. In certain cases, methods include diagnosing the subject as having insulin resistance, Type 1 diabetes, Type 2 diabetes, gestational diabetes or prediabetes. The subject may be diagnosed by any convenient clinical protocol, such as by blood sugar analysis, analysis of glycated hemoglobin (A1C) or some other laboratory analysis.

In some cases, the subject is a subject that exhibits at least one symptom of having NASH concurrently with having at least one symptom of Type 1 diabetes, Type 2 diabetes, gestational diabetes or prediabetes. In some cases, the subject is a subject that is diagnosed as having NASH in addition to being diagnosed with Type 1 diabetes, Type 2 diabetes, gestational diabetes or prediabetes.

In practicing the subject methods, an effective amount of at least one oxysterol active agent compound selected from 25-hydroxycholesterol-3-sulfate (25HC3S), 25-hydroxycholesterol-disulfate (25HCDS), 27-hydroxycholesterol-3-sulfate (27HC3S), 27-hydroxycholesterol-disulfate (27HCDS), 24-hydroxycholesterol-3-sulfate (24HC3S), 24-hydroxycholesterol-disulfate (24HCDS), and 24,25-epoxycholesterol-3-sulfate, or salt thereof is administered to the subject. In some cases, the oxysterol active agent compound is administered to the subject at a dosage of from 0.00001 mg/kg/day to 500 mg/kg/day, such as from 0.00005 mg/kg/day to 450 mg/kg/day, such as from 0.0001 mg/kg/day to 400 mg/kg/day, such as from 0.0005 mg/kg/day to 350 mg/kg/day, such as from 0.001 mg/kg/day to 300 mg/kg/day, such as from 0.005 mg/kg/day to 250 mg/kg/day, such as from 0.01 mg/kg/day to 200 mg/kg/day, such as from 0.05 mg/kg/day to 150 mg/kg/day, and including from 0.001 mg/kg/day to 100 mg/kg/day. In certain cases, the oxysterol active agent compound is administered to the subject at a dosage of from 0.001 mg/kg/day to 100 mg/kg/day. In certain cases, the oxysterol active agent compound is administered to the subject at a dosage of from 0.1 mg/kg/day to 100 mg/kg/day, 0.1 mg/kg/day to 10 mg/kg/day, or 0.1 mg/kg/day to 5 mg/kg/day. In certain cases, the oxysterol active agent compound is administered to the subject at a dosage of from 1 mg/kg/day to 100 mg/kg/day.

In some cases, the amount of each daily dose of the at least one oxysterol active agent compound, such as 25-hydroxycholesterol-3-sulfate or 25-hydroxycholesterol-3-sulfate sodium, administered to the individual is from 0.5 mg to 5 mg, 5 mg to 10 mg, 10 mg to 15 mg, 15 mg to 20 mg, 20 mg to 25 mg, 20 mg to 50 mg, 25 mg to 50 mg, 50 mg to 75 mg, 50 mg to 100 mg, 75 mg to 100 mg, 100 mg to 125 mg, 125 mg to 150 mg, 150 mg to 175 mg, 175 mg to 200 mg, 200 mg to 225 mg, 225 mg to 250 mg, 250 mg to 300 mg, 300 mg to 350 mg, 350 mg to 400 mg, 400 mg to 450 mg, or 450 mg to 500 mg, or 1 mg to 300 mg or 1 mg to 100 mg. In some cases, the amount of oxysterol active agent compound in the effective amount administered to the individual (e.g., a unit dosage form) is in the range of from 0.5 mg to 500 mg, such as from 1 mg to 450 mg, such as from 2 mg to 400 mg, such as from 5 mg to 300 mg, such as from 10 mg to 200 mg, or such as from 20 mg to 100 mg.

The oxysterol active agent compound may be administered to the subject once per day or more, such as twice per day or more, such as three times per day or more, and including four times per day or more. For instance, the oxysterol active agent compound may be administered twice a day, once a day, once every other day, once every three days, once a week, or once a month. In some cases, the oxysterol active agent compound is administered to the subject once per day. In some cases, the oxysterol active agent compound is administered to the subject twice per day. In some instances, the oxysterol active agent compound is administered to the subject once or twice per day in a cycle for a duration of ranging from 1 day to 10 days, 1 day to 30 days, 7 days to 30 days, 7 days to 90 days, 10 days to 180 days, or 30 days to 1 year, 30 days to 5 years, 90 days to 5 years, or 1 year to 10 years. In some cases, the oxysterol active agent compound is administered to the subject once per day for a duration of from 1 day to 30 days, such as once per day for a duration of from 1 day to 28 days, from 1 day to 21 days, from 7 days to 14 days. In some cases, the oxysterol active agent compound is administered to the subject twice per day for a duration of from 1 day to 30 days, such as twice per day for a duration of from 1 day to 28 days, from 1 day to 21 days, from 7 days to 14 days. In some cases, the oxysterol active agent compound is administered to the subject three times per day for a duration of from 1 day to 30 days, such as three times per day for a duration of from 1 day to 28 days, from 1 day to 21 days, from 7 days to 14 days. In some cases, the dosing is administered in cycles of administration of the oxysterol active agent compound. In some cases, the cycle is 1 day or more, such as 2 days or more, such as 3 days or more, such as 4, days or more, such as 5 days or more, such as 6 days or more, such as 7 days or more, such as 14 days or more, such as 21 days or more, such as 28 days or more, and in some instances the cycle is 30 days or more. The cycles of drug administration may be repeated for 1, 2, 3, 4, 5, 6, 7, 8, or more than 8 dosage cycles, for a total period of 6 months, 1 year, 2 years, 3 years, or 4 years or more. The administration of each pharmaceutical composition can be extended over an extended period of time (such as during maintenance therapy), such as from a month up to seven years. In some cases, the oxysterol active agent compound may be administered over a period of about any of 2, 3, 4, 5, 6, 7, 8, 9, 10, 11, 12, 18, 24, 30, 36, 48, 60, 72, or 84 months. In other cases, the oxysterol active agent compound is administered for the rest of the subject's lifetime.

Implementation of the methods generally involves identifying (e.g., diagnosing) patients suffering from or at risk of insulin resistance, diabetes, or prediabetes, and, optionally, also non-alcoholic steatohepatitis (NASH). The exact dosage to be administered may vary depending on the age, gender, weight, and overall health status of the individual patient, as well as the precise etiology of the disease. The dose will vary with the route of administration, the bioavailability, and the particular formulation that is administered, as well as according to the nature of the malady that is being prevented or treated. Further, the effective dose can vary depending upon factors such as gender, age, and other conditions of the patient, as well as the extent or progression of the disease condition being treated. In some cases, each dosage of the oxysterol active agent compound is administered to the subject over duration of from 0.1 hours to 12 hours (e.g., by intravenous administration) such as from 0.5 hours to 10 hours, such as from 1 hour to 8 hours, and including over a duration of from 2 hours to 6 hours.

Administration may be oral or parenteral, including intravenously, intramuscularly, subcutaneously, intradermal injection, intraperitoneal injection, etc., or by other routes (e.g., transdermal, sublingual, rectal and buccal delivery, inhalation of an aerosol, intravaginally, intranasally, topically, as eye drops, via sprays, etc.). In certain cases, the oxysterol active agent compound is administered to the subject by one or more of oral administration, enteric administration, sublingual administration, transdermal administration, intravenous administration, peritoneal administration, parenteral administration, administration by injection, subcutaneous injection, and intramuscular injection. The route of administration will depend on the nature or the condition that is treated, e.g., on the type or degree of the disease, and whether the treatment is prophylactic or intended to effect a cure. Further, administration of the compound by any means may be carried out as a single mode of therapy, or in conjunction with other therapies and treatment modalities, e.g., diet regimens, etc.

In some cases, the compositions are administered in conjunction with other treatment modalities such as various pain relief medications, anti-arthritis agents, chemotherapeutic agents, antibiotic agents, anti-neurodegeneration agents, anti-addiction agents, other diabetes agents, and the like, depending on the malady that is afflicting the subject. "In conjunction with" refers to both administration of a separate preparation of the one or more additional agents, and also to inclusion of the one or more additional agents in a composition of the present disclosure.

In some cases, methods and compositions described herein are administered while the subject is taking at least one of insulin, inhaled insulin, insulin analogs, insulin aspart, insulin degludec, insulin glargine, insulin isophane, insulin lispro, metformin, a glitazone, GLP-1, GLP-1 analogs, exenatide, liraglutide, semaglutide, dulaglutide, lixisenatide, GLP-1/glucagon agonists, GLP-1/GCGR agonists, FGF-21/GLP-1 dual agonists, GIP/GLP-1 dual agonists, GLP-1/GIP/glucagon triple agonists, SGLT-2 inhibitors, canagliflozin, dapagliflozin, empagliflozin, ertugliflozin, sulfonylureas, glyburide, glipizide, glimepiride, pramlinitide, glinides, repaglinide, nateglinide, thiazolidinediones, rosiglitazone, glibenclamide, pioglitazone, glucagon, DDP-4 inhibitors, sitagliptin, saxagliptin, linagliptin, vildagliptin, acarbose, albiglutide, alogliptin, bromocriptine mesylate, miglitol, atorvastatin, fluvastatin, lovastatin, pitavastatin, pravastatin, rosuvastatin, and simvastatin, or further comprising administering to the subject at least one of atorvastatin, fluvastatin, lovastatin, pitavastatin, pravastatin, rosuvastatin, and simvastatin. In some cases, methods and compositions described herein are administered while the subject is taking a lipid lowering drug, such as at least one of a statin, fenofibrate, omega-3 fatty acid, icosapent ethyl, and fish oil, or further comprising administering a lipid lowering drug, such as at least one of a statin, fenofibrate, omega-3 fatty acid, icosapent ethyl, and fish oil. In some cases, methods and compositions described herein are administered while the subject is receiving statin therapy. In some cases, the phrase "is taking" or "is receiving" refers to the administration of these supplemental treatment modalities to the subject while the subject is undergoing treatment with the oxygenated cholesterol sulfates according to methods described herein.

The oxysterol active agent compounds may be administered in the pure form or in a pharmaceutically acceptable formulation including suitable elixirs, binders, and the like (generally referred to a "carriers") or as pharmaceutically acceptable salts (e.g., alkali metal salts such as sodium, potassium, calcium, or lithium salts, ammonium, etc.) or other complexes. It should be understood that the pharmaceutically acceptable formulations include liquid and solid materials conventionally utilized to prepare both injectable dosage forms and solid dosage forms such as tablets and capsules and aerosolized dosage forms. In addition, the oxysterol active agent compounds may be formulated with aqueous or oil based vehicles. Water may be used as the carrier for the preparation of compositions (e.g., injectable compositions), which may also include conventional buffers and agents to render the composition isotonic. Other potential additives and other materials (preferably those which are generally regarded as safe [GRAS]) include: colorants; flavorings; surfactants (TWEEN®, oleic acid, etc.); solvents, stabilizers, elixirs, and binders or encapsulants (lactose, liposomes, etc). Solid diluents and excipients include lactose, starch, conventional disintegrating agents, coatings, and the like. Preservatives such as methyl paraben or benzalkium chloride may also be used. Depending on the formulation, it is expected that the active component (at least one oxysterol active agent) will be present at 1% to 99% of the composition and the vehicular "carrier" will constitute 1% to 99% of the composition. The pharmaceutical compositions of the present disclosure may include any suitable pharmaceutically acceptable additives or adjuncts to the extent that they do not hinder or interfere with the therapeutic effect of the at least one oxysterol active agent compound. Additional suitable agents that may be co-administered or co-formulated also include other agents, including but not limited to: metabolites of the methionine and/or glutathione biosynthetic pathways such as S-adenosylhomocysteine (SAH), S-methylmethionine (SMM), cystine, betaine, etc., or various forms and/or salts thereof, e.g., acetylcysteine (e.g., intravenous N-acetylcysteine), various neutraceuticals, etc.

Pharmaceutical compositions may include one or more pharmaceutically acceptable carriers. Pharmaceutically acceptable excipients have been amply described in a variety of publications, including, for example, A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., eds 7th ed., Lippincott, Williams, & Wilkins; and Handbook of Pharmaceutical Excipients (2000) A. H. Kibbe et al., eds., 3rd ed. Amer. Pharmaceutical Assoc. For example, the one or more excipients may include sucrose, starch, mannitol, sorbitol, lactose, glucose, cellulose, talc, calcium phosphate, or calcium carbonate, a binder (e.g., cellulose, methylcellulose, hydroxymethylcellulose, polypropylpyrrolidone, polyvinylpyrrolidone, gelatin, gum arabic, poly(ethylene glycol), sucrose or starch), a disintegrator (e.g., starch, carboxymethylcellulose, hydroxypropyl starch, low substituted hydroxypropylcellulose, sodium bicarbonate, calcium phosphate, or calcium citrate), a lubricant (e.g., magnesium stearate, light anhydrous silicic acid, talc, or sodium lauryl sulfate), a flavoring agent (e.g., citric acid, menthol, glycine, or orange powder), a preservative (e.g., sodium benzoate, sodium bisulfite, methylparaben, or propylparaben), a stabilizer (e.g., citric acid, sodium citrate, or acetic acid), a suspending agent (e.g., methylcellulose, polyvinylpyrrolidone, or aluminum stearate), a dispersing agent (e.g., hydroxypropylmethylcellulose), a diluent (e.g., water), and base wax (e.g., cocoa butter, white petrolatum, or polyethylene glycol).

In some cases, compositions of interest include an aqueous buffer. Suitable aqueous buffers include, but are not limited to, acetate, succinate, citrate, and phosphate buffers varying in strengths from 5 mM to 100 mM. In some cases, the aqueous buffer includes reagents that provide for an isotonic solution. Such reagents include, but are not limited to, sodium chloride; and sugars, e.g., mannitol, dextrose, sucrose, and the like. In some cases, the aqueous buffer further includes a non-ionic surfactant such as polysorbate 20 or 80. In some instances, compositions of interest further include a preservative. Suitable preservatives include, but are not limited to, a benzyl alcohol, phenol, chlorobutanol, benzalkonium chloride, and the like. In many cases, the composition is stored at about 4° C. Formulations may also be lyophilized, in which case they generally include cryoprotectants such as sucrose, trehalose, lactose, maltose, mannitol, and the like. Lyophilized formulations can be stored over extended periods of time, even at ambient temperatures.

In some cases, compositions include other additives, such as lactose, mannitol, corn starch, or potato starch; with binders, such as crystalline cellulose, cellulose derivatives, acacia, corn starch, or gelatins; with disintegrators, such as corn starch, potato starch, or sodium carboxymethylcellulose; with lubricants, such as talc or magnesium stearate; and if desired, with diluents, buffering agents, moistening agents, preservatives, and flavoring agents.

Where the composition is formulated for injection, the compositions may be formulated by dissolving, suspending, or emulsifying the oxysterol active agent compound in an aqueous or nonaqueous solvent, such as vegetable or other similar oils, synthetic aliphatic acid glycerides, esters of higher aliphatic acids, or propylene glycol; and if desired, with conventional additives such as solubilizers, isotonic agents, suspending agents, emulsifying agents, stabilizers, and preservatives.

In some cases, methods according to the present disclosure are directed to treatment of a subject based on a cellular response when the subject is administered the oxysterol active agent compound. In some instances of the present disclosure, epigenetic modification plays a role in the regulation and coordination of gene expression.

Methylation at position 5 of cytosine (5-methylcytosine, 5mC) in DNA is an important epigenetic modification that regulates gene expression among other functions of the genome. While not being bound by theory, cytosine methylation of CpG in the promoter region is inversely correlated with transcriptional activity of associated genes as it causes chromatin condensation and thus gene silencing. Dysregulation of CpG methylation and gene expression can affect tissue function and metabolic state. Cytosine methylation is catalyzed by DNA methyltransferase (DNMT-1,3a/3b), which also functions in the regulation of DNA methylation.

The major epigenetic regulation includes DNA and histone methylation, demethylation, acetylation, and deacetylation. The enzymes involved in the process are DNA and histone methyltransferases/demethylases, and acetyltransferases/deacetylases. In some cases, administering one or more of the oxysterol active agent compounds is sufficient to act as an epigenetic modulator of one or more of DNMT1, DNMT3a, DNMT3b, GCN3 (Giant congenital nevi), p300 (histone acetyl transferase), Pcaf (KAT2B lysine acetyltransferase 2B), HDAC1 (histone deacetylase 1), HDAC2 (histone deacetylase 2), HDAC3 (histone deacetylase 3), HDAC6 (histone deacetylase 6), HDAC10 (histone deacetylase 10), and KDM6B-JMJD3 (lysine demethylase 6B), such as where 25HC3S, 27HC, and 27HC3S, or cholesterol (Xol) and cholesterol-3-sulfate (Xol3S) are their endogenous ligand(s) to one or more of DNMT1, DNMT3a, DNMT3b, GCN3 (Giant congenital nevi), p300 (histone acetyl transferase), Pcaf (KAT2B lysine acetyltransferase 2B), HDAC1 (histone deacetylase 1), HDAC2 (histone deacetylase 2), HDAC3 (histone deacetylase 3), HDAC6 (histone deacetylase 6), HDAC10 (histone deacetylase 10), and KDM6B-JMJD3 (lysine demethylase 6B).

While not being bound by theory, in some cases the one or more administered oxysterol active agent compounds inhibits DNMT-1,3a, and 3b, which demethylated $^{5m}$CpG in promoter regions, increased gene expression and up-regulated master signaling pathways such as MAPK, Calcium, AMPK, and CREB signaling pathways. In certain cases, the one or more oxysterol active agent compounds regulate cell signaling pathways at transcriptional levels in nuclei. In some cases, the one or more oxysterol active agent compounds are administered in an amount sufficient to affect protein phosphorylation, inositol phosphorylation, and/or sphingosine phosphorylation in regulating cellular functions.

In some cases, the addition of one or more of the subject oxysterol active agent compound to human hepatocytes is sufficient to reverse methylation induced by HG, increase hypomethylated CpG in promoter regions of the key genes and increase targeting gene expression. In some cases, while not being bound by theory, CpG demethylation by the oxysterol active agent compound is the mechanism for its function of global regulation: decreasing lipid accumulation, anti-inflammatory responses, anti-oxidants, and anti-cell death.

The DUSP family is a subset of protein tyrosine phosphatases, many of which dephosphorylate mitogen-activated protein kinases (MAPKs) and hence are referred to as MAPK phosphatase. DUSP8, a unique member of DUSP family, plays an important role in signal transduction of the phosphorylation-mediated MAPK pathway, which regulates responses to oxidative stress and cell death signals in various human diseases. In some cases, administering the one or more oxysterol active agent compounds is sufficient to demethylate $^{5m}$CpG in promoter regions of DUSP genes, including DUSP8, DUSP1, and DUSP7, and their downstream genes, CREB5, PRDX, BAD, and ERK, and increase their expression. While not being bound by theory, the transcribed proteins from these genes are responsible for cell survival and proliferation. In certain cases, the effects of the at least one oxysterol active agent compound on promoting cell survival/proliferation and alleviating oxidative stress occur through inhibiting DNMTs and increasing expression of the DUSP family, especially DUSP8 and their downstream elements.

In some cases, a method of treatment involves modulating at least one gene selected from ABCC4, AC005264.2, ADCY1, ADCY4, ADCY5, ADH6, ADRB, ADRB1, AFDN, AGTR1, AKAP12, AL671762.1, ALAD, ANKRD1, ANKRD43, ATF3, ATP1A3, BAD, BIRC3, C11orf96, CACNA1A, CACNA1C-AS1, CACNA1D, CACNA1H, CACNB2, CACNG8, CELSR2, CREB5, CTB-186G2.1, CXCL2, CYB5B, CYP24A1, CYP51A1, CYR61, DDIT3, DRD5P2, DUSP genes, DUSP8, DUSP1, DUSP7, CREB5, EDNRB, EDN1, EHHADH, ELOVL6, ERK, FABP1, FDFT1, FRMD3, FMC1, FSTL3, GABBR1, GABBR2, GADD45B, GIPR, GLI3, GNA11, GNAQ, GNAS, GRIN2A, GRIN2C, GRIN3B, HBEGF, HMGCR, HMGCS1, HRAS, HRH1, HSPA6, ICAM1, ID3, ID4, IDI1, IL8, IL11, ITPKB, KANK4, KLB, KLF5, KLLN, KRTAP3-1, MAP2K6, MAP4K1, MAP4K4, MAPK1, MAPK8, MAT1A, MAX, METTL7A, MVK, NAP1L5, NCMAP, NTF3, P2RY8, PAQR8, PAQR9, PCSK9, PDE4D, PDGFB, PLA2G12B, PLCD1, PLPPR1, PMAIP1, PNPLA3, POU2AF1, PPP1CB, PRDX, PRLR, PTCH1, RAB11FIP4, RALGPS1, RAPGEF2, RELA, RHOBTB1, ROCK2, SC4MOL, SCN1A, SEC16B, SERPINE1, SKIL, SLC8A3, SLCO2B1, SLCO4C1, SLC2A14, SOCS2, SORBS2, SPHK1, SPTLC3, SQLE, TAB3, TCIM, TGFB3, THBS1, TMEM170B, TNS1, TNFSF10, TUBB8, UBASH3B, VAV2, VAV3 and ZNF385B.

In some cases, a method of treatment involves modulating at least one pathway selected from cAMP signaling pathway, cGMP-PKG signaling pathway, circadian entrainment, glutamatergic synapse, adrenergic signaling in cardiomyocytes, gap junction, Type II diabetes mellitus, endocytosis, calcium signaling pathway, dilated cardiomyopathy, vascular smooth muscle contraction, MAPK signaling pathway, cholinergic synapse, Rap1 signaling pathway, dopaminergic synapse, Adherens junction, arrhythmogenic right ventricular cardiomyopathy, pathways in cancer, GnRH signaling pathway, oxytocin signaling pathway, transcriptional misregulation in cancer, estrogen signaling pathway, insulin secretion, retrograde endocannabinoid signaling, long-term depression, colorectal cancer, insulin signaling pathway, axon guidance, alcoholism, platelet activation, amphetamine addiction, herpes simplex infection, tight junction, thyroid hormone signaling pathway, acute myeloid leukemia, chronic myeloid leukemia, notch signaling pathway, and dorso-ventral axis formation.

EXPERIMENTAL

The present invention will be further illustrated by way of the following Examples. These Examples are non-limiting and do not restrict the scope of the invention. Unless stated otherwise, all percentages, parts, etc. presented in the Examples are by weight. The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. By "average" is meant the arithmetic mean. Standard abbreviations may be used, e.g., bp, base pair(s); kb, kilobase(s); pl, picoliter(s); s or see, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1

Abbreviations

| | |
|---|---|
| 25HC | 25-Hydroxycholesterol |
| 25HC3S | 25-Hydroxycholesterol 3-Sulfate |
| 27HC | 27-Hydroxycholesterol |
| 27HC3S | 27-Hydroxycholesterol 3-Sulfate |
| $5^mC$ | 5-Methylcytosine |
| BAD | BCL2 associated agonist of cell death |
| CaV1 | Calcium voltage-gated channel subunit alpha1 D, CACNAID |
| CaV2 | Calcium voltage-gated channel subunit alpha1 A, CACNA1A |
| CaV3 | Calcium voltage-gated channel subunit alpha1 H, CACNA1H |
| CREB | CAMP response element-binding protein |
| DMEM | Eagle's minimal essential medium |
| DMGs | Differential methylated gene |
| DMRs | Differential methylated regions |
| DNMTs | DNA methyltransferases |
| DUSP | Dual-specificity phosphatase |
| FAS | Fatty acid synthase |
| GCN3 | Giant congenital nevi |
| HDAC1 | Histone deacetylase 1 |
| HDAC10 | Histone deacetylase 10 |
| HDAC2 | Histone deacetylase 2 |
| HDAC3 | Histone deacetylase 3 |
| HDAC6 | Histone deacetylase 6 |
| HG | High glucose |
| HMGR | 3-hydroxy-3-methylglutaryl-coenzyme A reductase |
| KDM6B-JMJD3 | Lysine demethylase 6B |
| KEGG | Kyoto Encyclopedia of Genes and Genomes |
| LINE | Long interspersed nuclear element |
| LPS | Lipopolysaccharides |
| LXRs | Nuclear liver oxysterol receptors |
| MAPK | A mitogen-activated protein kinase |
| NAFLD | Non-alcoholic fatty liver diseases |
| NFκB | Nuclear factor kappa-light-chain-enhancer of activated B cells |
| p300 | Histone acetyl transferase |
| Pcaf | KAT2B lysine acetyltransferase 2B |
| PGC-1α | Pparg coactivator 1 alpha |
| PPARγ | Peroxisome proliferator-activated receptor |

-continued

Abbreviations

| | |
|---|---|
| PRDX6 | Peroxiredoxin 6 |
| RT-PCR | Reverse transcription-polymerase chain reaction |
| SREBP | Sterol regulatory element-binding protein |
| WGBS | Whole genome bisulfite sequencing |
| Xol | Cholesterol |
| Xol3S | Cholesterol 3-Sulfate |

Materials and Methods

Materials

Cell culture reagents and supplies were purchased from GIBCO BRL (Grand Island, NY); Huh-7 cells were obtained from American Type Culture Collection (Rockville, MD). The reagents for real time RT-PCR were from AB Applied Biosystems (Warrington, UK). The chemicals used in this research were obtained from Sigma Chemical Co. (St. Louis, MO) or Bio-Rad Laboratories (Hercules, CA). All solvents were obtained from Fisher (Fair Lawn, NJ) otherwise indicated.

Cell Culture

Huh-7 and HepG-2 cells were cultured in DMEM media supplemented with 10% heat-inactivated fetal bovine serum (FBS), high glucose (HG, 4.5 g/L) at 37° C. in a humidified atmosphere of 5% $CO_2$.

Extraction and Determination of DNA and mRNA Levels

After culturing Huh-7 cells in DMEM medium with HG for 72 hours followed by treating with 25 µM 25HC3S for 4 hours, genomic DNA from 5,000 cells were extracted using QIAamp DNA Mini Kit (QIAGEN, Hilden, Germany). Each sample, 2 µg, was sent to EpigenDx, Inc. (Hopkinton, MA) for analysis of global methylation bisulfite sequencing. The same samples, 6 µg, were sent to Novogene Co., Ltd (Tianjin, China) for analysis of whole genome bisulfite sequencing (WGBS). Total RNA was isolated using the Promega SV total RNA isolation system (Madison, WI) with DNase treatment. Each sample, 2 µg, was used for the first-strand cDNA synthesis as recommended by the manufacturer (Invitrogen, Carlsbad, CA). Real-time RT-PCR was performed using SYBR Green as the indicator on ABI 7500 Fast Real-Time PCR System (Applied Biosystems, Foster City, CA). Amplifications of β-actin or GAPDH were used as internal controls. Relative messenger RNA (mRNA) expression was quantified with the comparative cycle threshold (Ct) method using the primer set shown in Table 1.1 and was expressed as $2^{-\Delta\Delta Ct}$.

TABLE 1.1

Primer Sequence for Real-time Polymerase Chain Reaction

| Gene name | Forward Sequence | Reverse Sequence |
|---|---|---|
| DUSP8 | TCAGCTCCGTCAACATCTGC (SEQ ID NO: 1) | CGCGTGCTCTGGTCATAGA (SEQ ID NO: 15) |
| DUSP7 | ATATCCTCAATGTCACACCCAA (SEQ ID NO: 2) | ATCTTCTGCATCAGATAGGCC (SEQ ID NO: 16) |
| MAPK1 | ATGGTGTGCTCTGCTTATGATA (SEQ ID NO: 3) | TCTTTCATTTGCTCGATGGTTG (SEQ ID NO: 17) |
| CREB5 | GCAACAAGTCATCCCAGCATAAT (SEQ ID NO: 4) | AAGAATCGGATTCAGGTCTGTT (SEQ ID NO: 18) |
| PRDX6 | TCAATAGACAGTGTTGAGGACC (SEQ ID NO: 5) | CCCGATTCCTATCATCGATGAT (SEQ ID NO: 19) |
| BAD | ATGTTCCAGATCCCAGAGTTTG (SEQ ID NO: 6) | ATGATGGCTGCTGCTGGTT (SEQ ID NO: 20) |
| CaV1 | AACAACAAACCAGAAGTCAACC (SEQ ID NO: 7) | CTAAGAATGAAGAAAGCGCTCC (SEQ ID NO: 21) |
| CaV2 | CGCTTCGGAGACGAGATGC (SEQ ID NO: 8) | TGCGCCATTGACTGCTTGT (SEQ ID NO: 22) |
| CaV3 | CATGCTGGTAATCATGATCAAC (SEQ ID NO: 9) | CGAAAATGAAGGCGTCAAAGG (SEQ ID NO: 23) |
| PGCIA | CACCAGCCAACACTCAGCTA (SEQ ID NO: 10) | ACGTCTTTGTGGCTTTTGCT (SEQ ID NO: 24) |
| HMGR | GTCATTCCAGCCAAGGTTGT (SEQ ID NO: 11) | GGGACCACTTGCTTCCATTA (SEQ ID NO: 25) |
| FAS | TGTGGACATGGTCACGGAC (SEQ ID NO: 12) | GGCATCAAACCTAGACAGGTC (SEQ ID NO: 26) |
| β-ACTIN | CATGTACGTTGCTATCCAGGC (SEQ ID NO: 13) | CTCCTTAATGTCACGCACGAT (SEQ ID NO: 27) |
| GAPDH | CAATGACCCCTTCATTGACC (SEQ ID NO: 14) | TTGATTTTGGAGGGATCTCG (SEQ ID NO: 28) |

Chemical Synthesis and Characterization of Sterol Sulfates, 25HC3S, Xol3S, 27HC3S 5-Cholesten-3β, 25-diol 3-sulfate (25-Hydroxycholesterol 3-Sulfate, 25HC3S); 5-cholesten-3β-ol, 3-sulfate (Cholesterol 3-Sulfate, Xol3S); 5-cholesten-30, 27-diol 3-sulfate (27-Hydroxycholesterol 3-Sulfate, 27HC3S) were synthesized as previously described with mild modification. Briefly, a mixture of 25-hydroxycholesterol, cholesterol, or 27-hydroxycholesterol (6.5 mg, 0.016 mmol) and triethylamine-sulfur trioxide (3.5 mg, 0.019 mmol) was dissolved in dry pyridine (300 μl) and was stirred at room temperature for 2 hours. The solvents were evaporated at 40° C. under nitrogen gas stream, and the syrup was added into 2 ml of 50% acetonitrile (loading buffer). The products were applied to a 6 cc Oasis cartridge (Waters), which had been primed by methanol (15 ml) and water (15 ml). The cartridge was successively washed with the loading buffer (15 ml), water (15 ml), methanol (15 ml), 50% methanol (15 ml), 5% ammonia hydroxide in 10% methanol (15 ml), and 5% ammonia hydroxide in 50% methanol (15 ml). The retained sulphated sterol was eluted with 5% ammonia hydroxide in 80% methanol (10 ml), respectively. After dilution with 10 times volume of acetonitrile, the solvents were evaporated to dryness under nitrogen gas stream, and the sterol sulphates were obtained in white powder form.

Enzyme Kinetic Study of 5-Cholesten-3β, 25-Diol 3-Sulfate

For the DNMT1 activity assay, the substrate solution, 0.001 mg/ml Poly(dI-dC):Poly(dI-dC) in 50 mM Tris-HCl, pH 7.5, 50 mM NaCl, 5 mM EDTA, 5 mM DTT, 1 mM PMSF, 5% glycerol, 0.01% Brij35, 1% DMSO was used. For the DNMT3a/3b activity assay, 0.0075 mg/ml Lambda DNA in 50 mM Tris-HCl, pH 7.5, 50 mM NaCl, 5 mM EDTA, 5 mM DTT, 1 mM PMSF, 5% glycerol, 1% DMSO, was used. The indicated DNMT1, DNMT3a, or DNMT3b was added to the appropriate substrate solution and gently mixed. Amounts of cholesterol (Xol), 25HC, 27HC, Xol3S, 25HC3S, or 27HC3S ranging from 5.08E-09 to 0.0001 μM in DMSO were added to the reaction mixture by using Acoustic Technology (Echo 550, LabCyte Inc. Sunnyvale, CA). The mixtures were first incubated for 15 min, then $^3$H-SAM was added to the reaction mixture to initiate the reaction, and the mixture was incubated for 60 min at 30° C. Following incubation, the reaction mixture was finally transferred to filter-paper for detection of radioactivity counts.

Analysis of Global Methylation, Long Interspersed Nucleotide Element 1 (LINE-1) Assay For global DNA methylation analysis, 500 ng of extracted genomic DNA was bisulfite-treated using the EZ DNA Methylation kit (Zymo Research, Inc., CA). PCR reaction and product purification were performed as per the manufacturer's protocol (GE Healthcare Life Sciences). The PCR products, 10 μl, were sequenced by Pyrosequencing on the PSQ96 HS System following the manufacturer's instructions (Pyrosequencing, Qiagen). The methylation status of each CpG site was determined individually as an artificial C/T SNP using QCpG software (Pyrosequencing, Qiagen).

The methylation level at each CpG site was calculated as the percentage of the methylated alleles divided by the sum of all methylated and unmethylated alleles. The mean methylation level was calculated using methylation levels of all measured CpG sites within the targeted region of each gene. Each experiment included non-CpG cytosines as internal controls to detect incomplete bisulfite conversion of the input DNA. In addition, a series of unmethylated and methylated DNA were included as controls in each PCR assay. Furthermore, PCR bias testing was performed by mixing unmethylated control DNA with in vitro methylated DNA at different ratios (0%, 5%, 10%, 25%, 50%, 75%, and 100%), followed by bisulfite modification, PCR, and Pyro-sequencing analysis.

Analysis of Whole Human Genome Bisulfite Sequencing (WGBS)

Each sample, 5.2 g of genomic DNA spiked with 26 ng lambda DNA, was fragmented by sonication to 200-300 bp with Covaris S220, followed by end repair and adenylation. Cytosine-methylated barcodes were ligated to sonicated DNA per the manufacturer's instructions. These DNA fragments were treated twice with bisulfite using EZ DNA Methylation-Gold™ Kit (Zymo Research) before the resulting single-strand DNA fragments were PCR amplified using KAPA HiFi Hot Start Uracil and Ready Mix (2×). Library concentration was quantified by Qubit® 2.0 Flurometer (Life Technologies, CA, USA) and quantitative PCR, and the insert size was assayed on an Agilent Bioanalyzer 2100 system.

The library preparations were sequenced on an Illumina Hiseq 2500/4000 or Novaseq platform and 125 bp/150 bp paired-end reads were generated. Image analysis and base calling were performed with Illumina CASAVA pipeline. Trimmomatic (Trimmomatic-0.36) software was used for quality control. Bismark software (version 0.16.3; Krueger F, 2011) was used to perform alignments of bisulfite-treated reads to a reference genome (−X 700-dovetail). DSS software (23) was used to identify differentially methylated regions (DMRs). KOBAS software was used to test the statistical enrichment of DMR related genes in the Kyoto Encyclopedia of Genes and Genomes (KEGG) pathways.

Transcriptional Profiling and Data Analysis

Total RNA was extracted and purified from HepG-2 cells using SV total RNA isolation system (Promega, Madison, WI). cDNAs were prepared and analyzed using GeneChip® Human Genome U133 Plus 2.0 Array, Affymetrix (Santa Clara, USA) as previously described with technical support from Shanghai Biotechnology Corporation. Direct target genes in the present study were selected based on more than 2-fold of reduction together with array detect signal more than 5 in both samples. Genes showing fold changes greater than 2 and array-detected signals greater than 7 in at least one sample were selected as differently expressed genes. DAVID software (https://david.ncifcrf.gov/conversion.jsp) was used to analyze GO enrichment of differently expressed genes.

Figure 1:
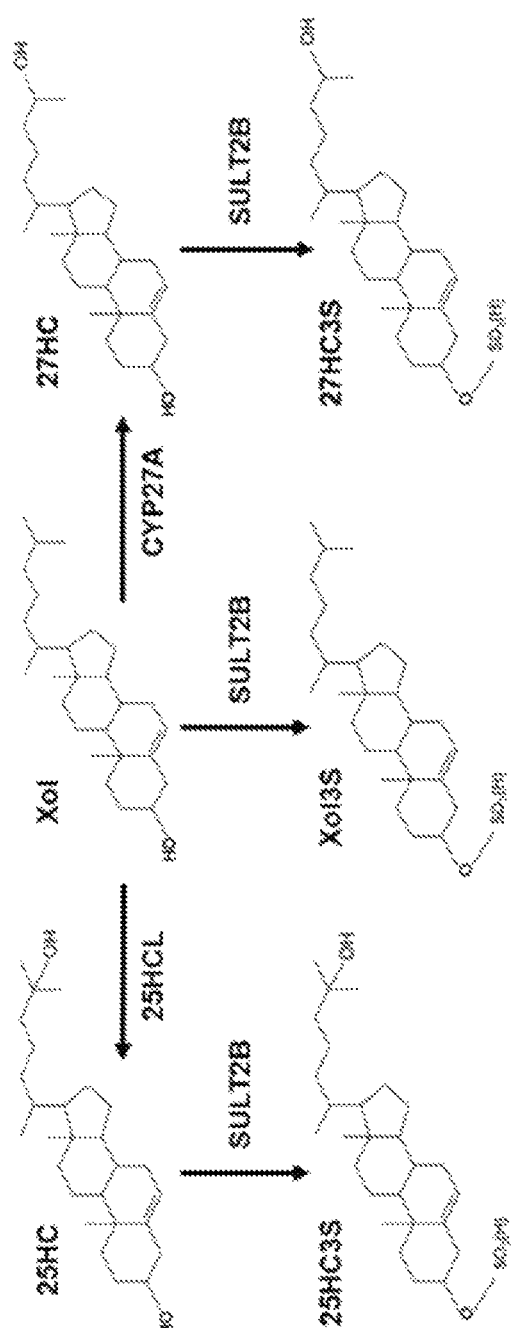
FIGS. 1A-1D. Synthesis and enzyme kinetic studies of Xol3S, 25HC3S, and 27HC3S. The biosynthesis of Xol3S, 25HC3S, and 27HC3S in the cells is shown in FIG. 1A. HPLC profiles of purified 25HC3S; Xol3S; and 27HC3S are shown in FIG. 1B. Effects of 25HC3S, 27HC3S, Xol3S, and their precursors, 25HC, 27HC, and cholesterol, on DNMT1/3a/3b activities. The concentration dependent, 0-0.001 μM (10 points), effects of 25HC3S, Xol3S, and 27HC3S on the enzyme activities is shown in FIG. 1C. Comparison of 25HC with 25HC3S, cholesterol with Xol3S, and 27HC with 27HC3S is shown in FIG. 1D.
Figure 1:
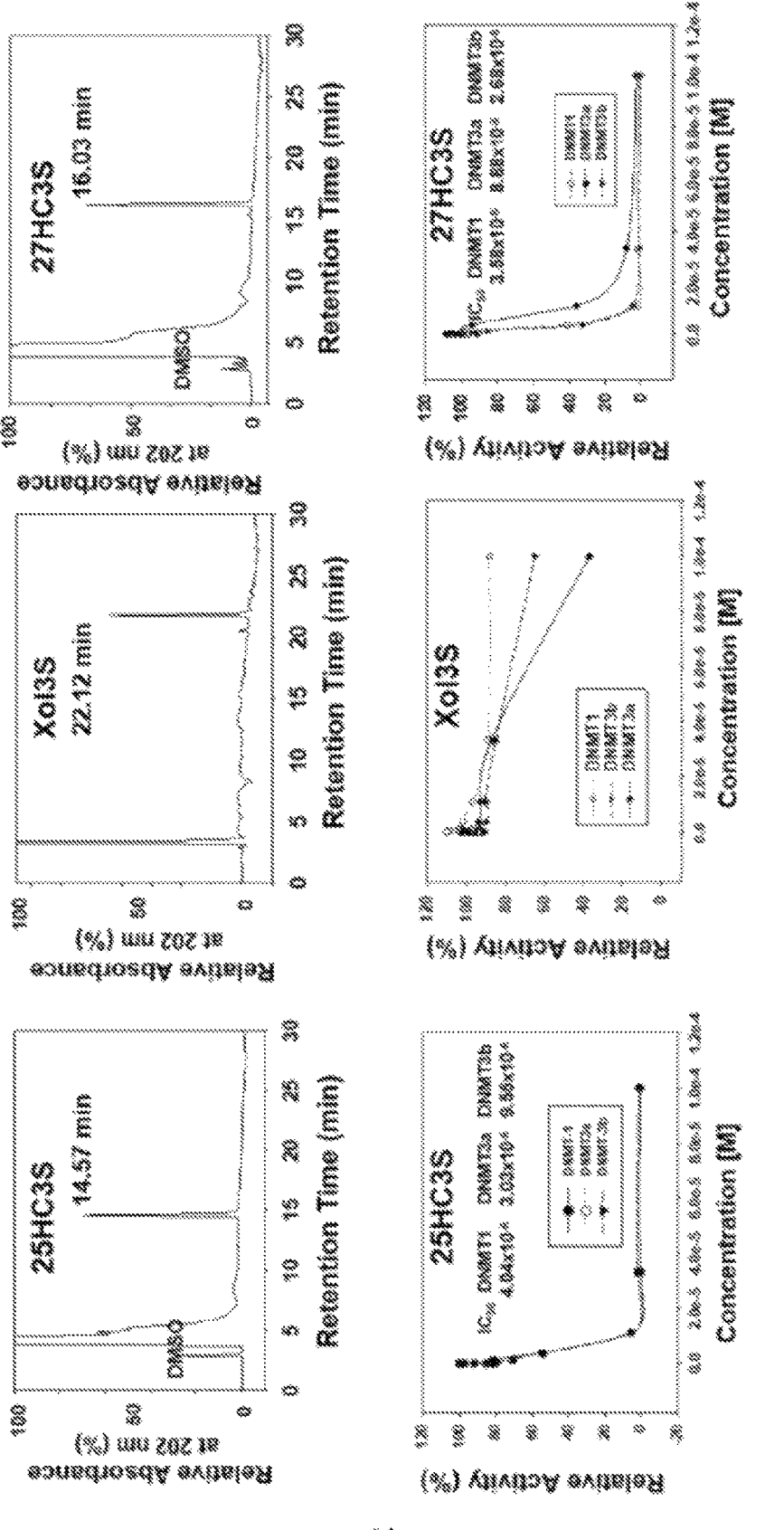
Figure 1:
Figure 1:
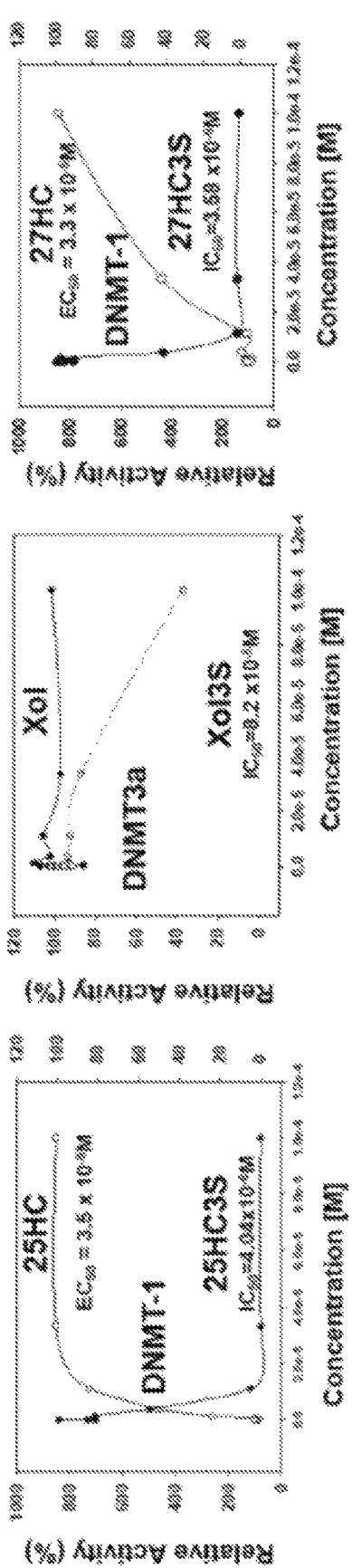

Results 25-hydroxycholesterol-3-sulfate (25HC3S) Specifically Inactivate DNMT Activities In order to study the effects of sterol sulfates on the epigenetic regulating targets, 25HS3S, Xol3S, and 27HC3S (FIG. 1A) were synthesized and purified to more than 95% purity using triethylamine sulphate complex methods as shown in FIG. 1B. Results show that 25HC3S significantly inhibits only DNMT-1,3a, and 3b activities with $IC_{50}$=4.04, 3.03, and 9.05×10⁻⁶ M, respectively (FIG. 1C, Left), while its precursor 25HC activates DNMT-1 activity by 8-fold with $EC_{50}$=3.5×10⁻⁶ µM (FIG. 1D, Left). As controls, Xol as well as Xol3S did not significantly affect enzymatic activities although Xol3S slightly inhibits DNMT3a with $IC_{50}$=8.2×10⁻⁵ M, which is most likely not physiologically significant (FIG. 1C, Middle). Compared with 25HC3S, 27HC3S did inhibit DNMTs with similar $IC_{50}$=3.58×10⁻⁶ µM for DNMT1, 8.88×10⁻⁶ µM for DNMT3a, and 2.68× 10⁻⁶ µM for DNMT3b as shown in FIG. 1C. Right. In contrast, its precursor 27HC, was much less potent in activation of DNMT-1 with $EC_{50}$=3.3×10⁻⁵ µM and had no effect on other enzymes (FIG. 1D, Right). In contrast to the 3 DNMTs, the 9 other epigenetic enzymes are not affected by these oxysterols or sterol sulfates (data not shown). As a positive control, S-adenosyl homocysteine (SAH) inhibited DNMT1 activity by 95% at 1 µM (data not shown), as previously reported. The results demonstrated that both 25HC3S and 27HC3S are potent inhibitors of DNMTs. However, only 25HC3S has been discovered in vivo in human hepatocyte nuclei: first found in concentration of 20 ug/g (~40 uM) following overexpression of mitochondrial cholesterol delivery protein, StarD1. The kinetic study shows that the IC50s are between 1-10 uM.

25-hydroxycholesterol-3-sulfate (25HC3S) Decreases ⁵ᵐCpG Levels in Global Promoter Regions Previous studies have shown that global DNA methylation and the methylation of specific genes are involved in adipogenesis, lipid metabolism, and inflammation in visceral adipose tissues, which, in turn, are related to the specific etiology of metabolic syndrome. To study the effects of 25HC3S on methylation status of ⁵ᵐCpG in global promoter regions, LINE-1 analysis was first performed to estimate global demethylation. Methylation usually occurs in repetitive elements, such as LINE elements. There are ~500,000 LINE elements and 750 million copies in total human genome. Human LINE-1 is a retro-transposable region (promoter region) and has only 700,000 copies, which correlates to ~17% of the human genome. The specific sequence includes four CpG dinucleotides (Pos 1, 2, 3, and 4), which serve as methylation/demethylation targets in LINE-1. As shown in FIG. 2A, culturing Huh-7 cells in high glucose media (HG), Pos 3 and Pos 4 had higher methylation, while all 4 Pos increased methylation after culturing cells in ethanol control. Reduction of methylation (demethylation) at Pos1 (−5%), Pos3 (−10%), and Pos 4 (−5.6%) occurred after incubating cells with 25HC3S for 4 hours. The results indicate that 25HC3S significantly reduce ⁵ᵐCpG methylation in promoter regions induced by HG or ethanol.

Profiles of Whole Genome-Wide DNA Methylation in 25HC3S-Treated Human Hepatocytes To understand the possible cellular functions of ⁵ᵐCpG demethylation in 25HC3S-treated Huh-7 cells, the cells were harvested for the construction of bisulfite-treated genomic DNA libraries. In 5 total WGBS, there were 366 million (Vehicle) and 370 million (25HC3S-treated) raw reads generated from the two libraries by paired-end sequencing, respectively. Among clean reads, 360 million, from vehicle library, 77% (277 million) were uniquely mapped to the reference genome of "human reference genome (hg38)", while among 365 million clean reads from the 25HC3S-treated library, 78% (286 million) were uniquely mapped to the reference genome, exhibiting an average read depth of 22 and 20, respectively. In these two libraries, more than 80% of cytosine residues were covered by at least ten reads in "human reference genome (hg38)". The depth and density of the sequencing were enough for a high-quality genome-wide methylation analysis. Meanwhile, the efficiencies of bisulfite conversion, represented by the lambda DNA to the libraries, were over 99%, providing reliable and accurate results for the WGBS (Table 1.2).

TABLE 1.2

| | | | | Uniquely mapped | | | | BS conversion |
| Sample name | Raw reads | Clean reads | Clean ratio (%) | Uniquely mapped reads | rate (%) | Sites_covgMean | Sites_num Covg10 | rate (%) |
|---|---|---|---|---|---|---|---|---|
| Vehicle | 366, 129, 468 | 360, 798, 889 | 90.30 | 276, 588, 428 | 76.66 | 19.68 | 80.78 | 99.727 |
| 25HC3S | 370, 635, 495 | 365, 154, 331 | 90.15 | 285, 623, 717 | 78.22 | 21.09 | 83.17 | 99.795 |

CpG methylation and demethylation are well documented to related with gene expression. A total of about 7,136 differential methylated regions (DMRs) under CG context were identified as hypomethylated regions located in 1,106 genes (differential methylated genes, DMGs). In 97% (1,074) of the DMGs, the hypomethylated regions were identified in their promoters (FIG. 2B). The hypomethylated genes were highly enriched in 75 KEGG pathways (p<0.05) (Table 1.3). The top 20 pathways (from the most significance, $p<10^{-9}$) were shown in FIGS. 2E and 2F. Among these pathways, MAPK-ERK and calcium-cAMP signaling are believed as the master pathways regulating cell survival, anti-oxidants, anti-apoptosis, energy metabolism, and lipid homeostasis. The pathways identified from whole genome are shown in FIG. 2E, and those identified from promoter regions are shown in FIG. 2F. Both sets of pathways, from whole genome or from promoter regions, are very similar. All pathways identified from promoter regions were hypomethylated without any hypermethylated CpGs in their promoter regions, indicating up-regulated gene expressions.

DNA methylation levels in whole genome and differential methylated regions (DMRs) are shown in FIG. 2B. To present the global DNA methylation profiles of the two libraries, the uneven methylation levels throughout the chromosomes under CG, CHG (H represents adenosine or thymidine residues), and CHH contexts are shown in FIG. 2B. A total of 6,923 differentially methylated genes (DMGs) were screened out among the two libraries. Moreover, 1,510 were 20 identified under CG context, 420 under CHG context, and 3,359 under CHH context. 83 were identified under CG and CHG contexts, 481 under CG and CHH contexts, 793 under CHG and CHH contexts, while only 277 were identified under CG, CHG, and CHH contexts. Furthermore 2,853 were identified as promoter regions, and 1,413 were identified under CG context, 186 under CHG context, and 787 under CHH context. For these DMGs, 59 were identified under CG and CHG contexts, 46 under CG and CHH, 260 under CHG and CHH contexts, and only 103 were identified under CG, CHG, and CHH contexts. While in these DMGs, 80.93% (5,603) were identified as hypomethylated, and 37.55% (2,104) were identified as hypomethylated in promoter 5 regions (FIG. 2C).

TABLE 1.3

Significant Enrichment KEGG Pathways of Hypomethylated DMGs in Promoter Region under CG Context

| Pathway name | P-value | Pathway name | P-value |
|---|---|---|---|
| CAMP signaling pathway | 3.69E−07 | Cocaine addiction | 0.014096 |
| cGMP-PKG signaling pathway | 2.65E−05 | Viral carcinogenesis | 0.01429 |
| Circadian entrainment | 5.68E−05 | Pancreatic cancer | 0.015201 |
| Glutamatergic synapse | 8.40E−05 | Inflammatory mediator regulation of TRP channels | 0.015802 |
| Adrenergic signaling in cardiomyocytes | 0.000108 | Hippo signaling pathway | 0.017014 |

TABLE 1.3-continued

Significant Enrichment KEGG Pathways of Hypomethylated DMGs in Promoter Region under CG Context

| Pathway name | P-value | Pathway name | P-value |
|---|---|---|---|
| Gap junction | 0.000227 | Melanogenesis | 0.017221 |
| Type II diabetes mellitus | 0.000505 | Neurotrophin signaling pathway | 0.018561 |
| Endocytosis | 0.000656 | Salmonella infection | 0.018615 |
| Calcium signaling pathway | 0.000656 | Chagas disease (American trypanosomiasis) | 0.01954 |
| Dilated cardiomyopathy | 0.000656 | Thyroid hormone synthesis | 0.021071 |
| Vascular smooth muscle contraction | 0.000752 | HTLV-I infection | 0.021071 |
| MAPK signaling pathway | 0.000877 | Prostate cancer | 0.021071 |
| Cholinergic synapse | 0.001123 | GABAergic synapse | 0.021665 |
| Rap1 signaling pathway | 0.001123 | Salivary secretion | 0.021665 |
| Dopaminergic synapse | 0.001194 | Cell adhesion molecules (CAMs) | 0.022648 |
| Adherens junction | 0.001194 | Amoebiasis | 0.023054 |
| Arrhythmogenic right ventricular cardiomyopathy | 0.001203 | Viral myocarditis | 0.024448 |
| Pathways in cancer | 0.001203 | Type I diabetes mellitus | 0.024448 |
| GnRH signaling pathway | 0.001679 | Focal adhesion | 0.024448 |
| Oxytocin signaling pathway | 0.002196 | Ras signaling pathway | 0.024601 |
| Transcriptional misregulation in cancer | 0.002515 | Fructose and mannose metabolism | 0.025877 |
| Estrogen signaling pathway | 0.002932 | One carbon pool by folate | 0.027147 |
| Insulin secretion | 0.003045 | Serotonergic synapse | 0.027147 |
| Retrograde endocannabinoid signaling | 0.003437 | Endocrine and other factor-regulated calcium reabsorption | 0.029495 |
| Long-term depression | 0.003463 | Hypertrophic cardiomyopathy (HCM) | 0.034694 |
| Colorectal cancer | 0.004132 | Long-term potentiation | 0.036088 |
| Insulin signaling pathway | 0.004549 | Ovarian steroidogenesis | 0.036088 |
| Axon guidance | 0.005282 | Wnt signaling pathway | 0.036088 |
| Alcoholism | 0.005377 | Endometrial cancer | 0.038405 |
| Platelet activation | 0.006325 | AMPK signaling pathway | 0.040972 |
| Amphetamine addiction | 0.006325 | Fc epsilon RI signaling pathway | 0.041787 |
| Herpes simplex infection | 0.006736 | Allograft rejection | 0.045211 |
| Tight junction | 0.007081 | Bile secretion | 0.045703 |
| Thyroid hormone signaling pathway | 0.007681 | Prolactin signaling pathway | 0.045703 |
| Acute myeloid leukemia | 0.007681 | Chemokine signaling pathway | 0.046416 |
| Chronic myeloid leukemia | 0.008581 | Neuroactive ligand-receptor interaction | 0.046416 |

TABLE 1.3-continued

Significant Enrichment KEGG Pathways of Hypomethylated DMGs in
Promoter Region under CG Context

| Pathway name | P-value | Pathway name | P-value |
|---|---|---|---|
| Notch signaling pathway | 0.012054 | Fc gamma R-mediated phagocytosis | 0.047019 |
| Dorso-ventral axis formation | 0.013526 | | |

Previous report has shown that high glucose incubation (HG), an in vitro model for study of NAFLD, induces lipid accumulation via increasing DNA promoter methylation signaling. It was noted that the hypermethylated $^{5m}$CpG in the promoter regions induced by HG were demethylated by 25HC3S. 25HC3S demethylated $^{5m}$CpG in promoter regions of 23 genes in MAPK signaling pathway (Table 1.4), 19 genes in Calcium pathway (Table 1.5), and 28 genes in cAMP pathway (Table 1.6). No hypermethylated DMR was found in the genes involved in the signaling pathways. The chromosome and sequence location of the hypermethylated $^{5m}$CpG by HG and the hypomethylated CpG by 25HC3S in promoter regions are compared in the tables. It is observed that these genes are also involved in many other KEGG pathways including insulin, Type II Diabetes Mellitus, and cGMP-PKG signaling pathways. The results indicate that the global regulatory mechanisms of 25HC3S are through demethylation of $^{5m}$CpG in promoter regions of the key genes, such as the DUSP and Calcium channel families, involved in MAPK-ERK and calcium-cAMP master signaling pathways.

DNA methylation levels generally show a varied distribution across different functional regions of the genome. The methylation levels in the CGI (CG island), CGI-shore (up to 2k bp away from the CGI), promoter (upstream 2k bp sequence from transcription starting site), 5'untranslated region (UTR5), exon, intron, 3'untranslated region (UTR3), and repeat were 10 significant different between vehicle and 25HC3S treated groups. It is interesting that 25HC3S treatment resulted in significantly higher hypomethylation levels than vehicle (FIG. 2D). In a total of 34,508 DMRs identified, 3,676 (1,549 hypermethylated and 2,127 hypomethylated) were distributed in CGI, 2206 (627 hypermethylated and 1,579 hypomethylated) in CGI-shore, 3,263 (1,213 hypermethylated and 2,050 hypomethylated) in exon, 9,850 (2,340 hypermethylated and 15 7,510 hypomethylated) in intron, 3,696 (1,187 hypermethylated and 2,509 hypomethylated) in promoter, 8,956 (1,882 hypermethylated and 7,774 hypomethylated) in repeat region, 61 (16 hypermethylated and 45 hypomethylated) in TES elements, 452 (179 hypermethylated and 273 hypomethylated) in TSS elements, 403 (123 hypermethylated and 280 hypomethylated) in UTR3 regions, and 1245 (432 hypermethylated and 813 hypomethylated) in UTR5 regions. In almost all 20 DMRs, CpGs are significantly more hypomethylated than hypenmethylated. It has been reported that CG methylation in promoter regions plays a key role in silencing gene expression.

In a total of 6,923 DMGs, the genes under CG context were highly enriched in 120 KEGG pathways (69 hypomethylated and 51 hypermethylated). The genes under CHG context were enriched in 48 pathways (33 hypomethylated and 15 hypermethylated), while those under Cull context, enriched in 136 pathways (101 hypomethylated and 35 hypermethylated). DMGs in promoter regions were highly enriched in 114 (31 hypermethylated and 83 hypomethylated) pathways, of which 75 (0 hypermethylated and 75 hypomethylated) under CG context, 13 (13 hypermethylated and 0 hypomethylated) under CHG context, and 26 (18 hypermethylated and 8 hypomethylated) under CHH context (Table 1.3).

TABLE 1.4

Demethylation of $^{5m}$CpG in Promoter Regions of MAPK Signaling Genes
(P = 0.00087)

| Gene name | Chromosome | DMR location in promoter region | | DMR (Methylation %) | |
|---|---|---|---|---|---|
| | | Start | End | HG-LG | 25HC3S-Vehicle |
| MAPK8 | Chr10 | 48306510 | 48306561 | | −29.24 |
| DUSP8 | Chr11 | 1572973 | 1573032 | | −30.51 |
| | | 1573583 | 1573855 | +41.72 | |
| MAX | Chr14 | 65102273 | 65102358 | | −31.75 |
| DUSP7 | Chr3 | 52056416 | 52056485 | | −40.47 |
| | | 52056538 | 52056778 | +31.75 | |
| NTF3 | Chr12 | 5432796 | 5432882 | | −33.48 |
| CACNA1D | Chr3 | 53494583 | 53494705 | | −20.46 |
| | | 53493469 | 53494019 | +49.03 | |
| CACNA1H | Chr16 | 1194928 | 1195015 | | −26.48 |
| | | 1194670 | 1195215 | +41.26 | |
| CACNA1A | Chr19 | 13226635 | 13226711 | | −39.91 |
| | | 13238959 | 13239237 | +9.51 | |
| MAPK1 | Chr22 | 21867450 | 21867512 | | −7.66 |
| | | 21867333 | 21867621 | +20.15 | |
| HRAS | Chr11 | 535071 | 535127 | | −18.85 |
| | | 536242 | 537214 | +42.8 | |
| PDGFB | Chr22 | 39243967 | 39244084 | | −30.51 |
| | | 39242292 | 39242477 | +29.29 | |
| CACNA1C-AS1 | Chr12 | 2691335 | 2691438 | | −20.97 |
| CACNB2 | Chr10 | 18140401 | 18140547 | | −21.91 |
| | | 18340356 | 18341053 | +47.13 | |
| MAP4K1 | Chr19 | 38596260 | 38596495 | | −34.3 |
| RAPGEF2 | Chr4 | 1.59E+08 | 1.59E+08 | | −36.05 |
| CTB-186G2.1 | Chr19 | 38596260 | 38596495 | | −34.3 |
| RELA | Chr11 | 65661914 | 65662035 | | −35.1 |
| GADD45B | Chr19 | 2474806 | 2474873 | | −28.6 |

TABLE 1.4-continued

| Demethylation of $^{5m}$CpG in Promoter Regions of MAPK Signaling Genes (P = 0.00087) | | | | | |
|---|---|---|---|---|---|
| | DMR location in promoter region | | | DMR (Methylation %) | |
| Gene name | Chromosome | Start | End | HG-LG | 25HC3S-Vehicle |
| AL671762.1 | Chr6 | 31828019 | 31828149 | | −27.17 |
| CACNG8 | Chr19 | 53961377 | 53961479 | | −31.18 |
| MAP4K4 | Chr2 | 1.02E+08 | 1.02E+08 | | −13.63 |
| | | 1.02E+08 | 1.02E+08 | +17.93 | |
| TGFB3 | Chr14 | 75982395 | 75982557 | | −23.74 |

Table 1.4—After culturing Huh-7 cells in DMEM medium with HG for 72 hours followed by treating with ethanol (vehicle) and 25 nM 25HC3S for 4 hours, genomic DNA from 5,000 cells were extracted using QIAamp DNA Mini Kit (QIAGEN, Hilden, Germany). Each sample (6 µg) was used for analysis of the whole genome bisulfite sequencing (WGBS). The KEGG analysis shows that the demethylated genes are involved in MAPK signaling pathway (p=0.00087). Of the 257 total genes in the MAPK signaling pathway, 23 were demethylated by the 25HC3S treatment. Of these 23 genes, 10 were found to be methylated by a HG environment (shown in bold). The first column represents the gene name, the second column (DMR location in promoter region) shows the location of differential methylation region in the chromosome, the third column (DMR (Methylation %)) shows the methylation rates by high glucose (HG) and demethylation rates induced by 251HC3S.

TABLE 1.5

| Demethylation of $^{5m}$CpG in Promoter Regions of Calcium Signaling Genes (P = 0.00066) | | | | | |
|---|---|---|---|---|---|
| | DMR location in promoter region | | | DMR (Methylation %) | |
| Gene name | Chromosome | Start | End | HG-LG | 25HC3S-Vehicle |
| ADCY4 | Chr14 | 24334570 | 24334719 | | −18.63 |
| | | 24334404 | 24334719 | +32.6 | |
| DRD5P2 | Chr1 | 1.43E+08 | 1.43E+08 | | −34.73 |
| EDNRB | Chr13 | 77919496 | 77919743 | | −34.09 |
| ADRB1 | Chr10 | 1.14E+08 | 1.14E+08 | | −33.1 |
| GRIN2A | Chr16 | 10183302 | 10183414 | | −19.63 |
| | | 10084383 | 10084724 | +8.62 | |
| GNA11 | Chr19 | 3094383 | 3094442 | | −32.66 |
| | | 3092574 | 3092876 | +6.13 | |
| SPHK1 | Chr17 | 76383180 | 76383291 | | −24.74 |
| CACNA1C-AS1 | Chr12 | 2691335 | 2691438 | | −20.97 |
| HRH1 | Chr3 | 11154292 | 11154354 | | −25.48 |
| ITPKB | Chr1 | 2.27E+08 | 2.27E+08 | | −25.12 |
| | | 2.27E+08 | 2.27E+08 | +23.84 | |
| PLCD1 | Chr3 | 38029863 | 38030016 | | −24.31 |
| | | 38029901 | 38030042 | +26.02 | |
| GNAS | Chr20 | 58888598 | 58888893 | | −25.68 |
| | | 58888560 | 58888756 | +23.2 | |
| AC005264.2 | Chr19 | 3156392 | 3156457 | | −15.76 |
| CACNA1D | Chr3 | 53494583 | 53494705 | | −20.46 |
| | | 53493469 | 53494019 | +49.03 | |
| GNAQ | Chr9 | 78032198 | 78032440 | | −11.92 |
| GRIN2C | Chr17 | 74861739 | 74861853 | | −37.6 |
| | | 74854901 | 74855100 | +36.66 | |
| SLC8A3 | Chr14 | 70188747 | 70189089 | | −28.51 |
| | | 70046033 | 70046320 | +65.66 | |
| CACNA1H | Chr16 | 1194928 | 1195015 | | −26.48 |
| | | 1194670 | 1195215 | +41.26 | |

Table 1.5—Cells preparation and DNA methylation as described in Table 1.1. The KEGG analysis shows that the demethylated genes are involved in calcium signaling pathway (P=0.00066). Of the 180 total genes in the Calcium signaling pathway, 19 were demethylated by the 25HC3S treatment. Of these 19 genes, 10 were found to be methylated by a HG environment (shown in bold). The first column represents the gene name, the second column (DMR location in promoter region) shows the location of differential methylation region in the chromosome, the third column (DMR (Methylation %)) shows the methylation rates by high glucose (HG) and demethylation rates induced by 25HC3S.

and MAPK1) and their target genes CREB5, PRDX6, and BAD in the MAPK pathway, as well as the key genes CACNA1D (CaV1), CACNA1A (CaV2), and CACNA1H (CaV3) (encoding for calcium voltage-gated channel subunits) and their targeting genes (PGC1A, HMGR, and FAS)

TABLE 1.6

| Demethylation of $^{5m}$CpG in Promoter Regions of cAMP Signaling Genes (P = 3.69E–07) | | | | | |
|---|---|---|---|---|---|
| | DMR location in promoter region | | | DMR (Methylation %) | |
| Gene name | Chromosome | Start | End | HG-LG | 25HC3S-Vehicle |
| MAPK8 | Chr10 | 48306510 | 48306561 | | −29.24 |
| PTCH1 | Chr9 | 95508446 | 95508561 | | −12.09 |
| ADCY5 | Chr3 | 1.23E+08 | 1.23E+08 | | −30.44 |
| | | 1.23E+08 | 1.23E+08 | +15.8 | |
| GLI3 | Chr7 | 42228171 | 42228223 | | −19.62 |
| | | 42184839 | 42185064 | +8.27 | |
| PPP1CB | Chr2 | 28751716 | 28751798 | | −10.93 |
| | | 28793684 | 28794075 | +7.5 | |
| GNAS | Chr20 | 58888598 | 58888893 | | −25.68 |
| | | 58888560 | 58888756 | +23.2 | |
| CACNA1D | Chr3 | 53494583 | 53494705 | | −20.46 |
| | | 53493469 | 53494019 | +49.03 | |
| GRIN2A | Chr16 | 10183302 | 10183414 | | −19.63 |
| MAPK1 | Chr22 | 21867450 | 21867512 | | −7.66 |
| | | 21867333 | 21867621 | +20.15 | |
| GABBR2 | Chr9 | 98708549 | 98708610 | | −21.84 |
| CREB5 | Chr7 | 28489448 | 28489601 | | −29.31 |
| | | 28776194 | 28776325 | +27.34 | |
| GRIN3B | Chr19 | 1000331 | 1000405 | | −34.67 |
| CACNA1C-AS1 | Chr12 | 2691335 | 2691438 | | −20.97 |
| VAV2 | Chr9 | 1.34E+08 | 1.34E+08 | | −33.11 |
| | | 1.34E+08 | 1.34E+08 | +44.31 | |
| ABCC4 | Chr13 | 95301634 | 95301736 | | −33.06 |
| PDE4D | Chr5 | 59893498 | 59893718 | | −27.84 |
| | | 59215742 | 59215941 | +39.66 | |
| ROCK2 | Chr2 | 11344628 | 11344733 | | −23.14 |
| ADCY1 | Chr7 | 45574500 | 45574591 | | −14.76 |
| | | 45574683 | 45574877 | +25.79 | |
| ADCY4 | Chr14 | 24334570 | 24334719 | | −18.63 |
| | | 24334404 | 24334719 | +32.6 | |
| DRD5P2 | Chr1 | 1.43E+08 | 1.43E+08 | | −34.73 |
| ADRB1 | Chr10 | 1.14E+08 | 1.14E+08 | | −33.1 |
| GIPR | Chr19 | 45668710 | 45668767 | | −10.04 |
| | | 45669075 | 45669744 | +43.62 | |
| RELA | Chr11 | 65661914 | 65662035 | | −35.1 |
| AFDN | Chr6 | 1.68E+08 | 1.68E+08 | | −30.68 |
| BAD | Chr11 | 64286088 | 64286179 | | −42.33 |
| ATP1A3 | Chr19 | 41999134 | 41999316 | | −15.75 |
| GRIN2C | Chr17 | 74861739 | 74861853 | | −37.64 |
| | | 74854901 | 74855100 | +36.66 | |

Table 1.6—Cells preparation and DNA methylation as described in Table 1.1. The KEGG analysis shows that the demethylated genes are significantly involved in cAMP signaling pathway (P=3.69E-07). Of the 200 total genes in the cAMP signaling pathway, 28 were demethylated by the 25HC3S treatment. Of these 28 genes, 13 were found to be methylated by a HG environment (shown in bold). The first column represents the gene name, the second column (DMR location in promoter region) shows the location of differential methylation region in the chromosome, the third column (DMR (Methylation %)) shows the methylation rates by high glucose (HG) and demethylation rates induced by 25HC3S.

Relationship between $^{5m}$CpG Demethylation in Promoter Regions and Gene Expression: 25HC3S Decreases HG-induced $^{5m}$CpG Levels in Promoter Regions To explore the relationship of promoter $^{5m}$CpG demethylation and gene expression from the results of KEGG pathway analysis, the expression of key genes (DUSP7,8 in the calcium-AMK pathway were determined by RT-PCR analysis. The DUSP-MAPK signaling pathway is the major pathway involved in cell survival/death and anti-oxidization, and the calcium signaling pathway controls lipid and energy metabolism. As expected, 25HC3S increased expression of DUSP8 by 5-fold and its targeting gene, CREB5, by up to 20-fold, which is the key element involved in cell survival and death (FIGS. 3A and 3B). Meanwhile, 25HC3S treatment significantly increased expression of key genes involved in the calcium signaling pathway, and its downstream element, PGC1A, by 12-fold, while it decreased expression of HMGR and FAS genes by ~90%, which encode the key enzymes controlling energy metabolism in mitochondria, cholesterol biosynthesis, and fatty acid biosynthesis, as shown in FIGS. 3C and 3D.

Transcriptional Array Analysis in Hepatocytes

Figure 4:
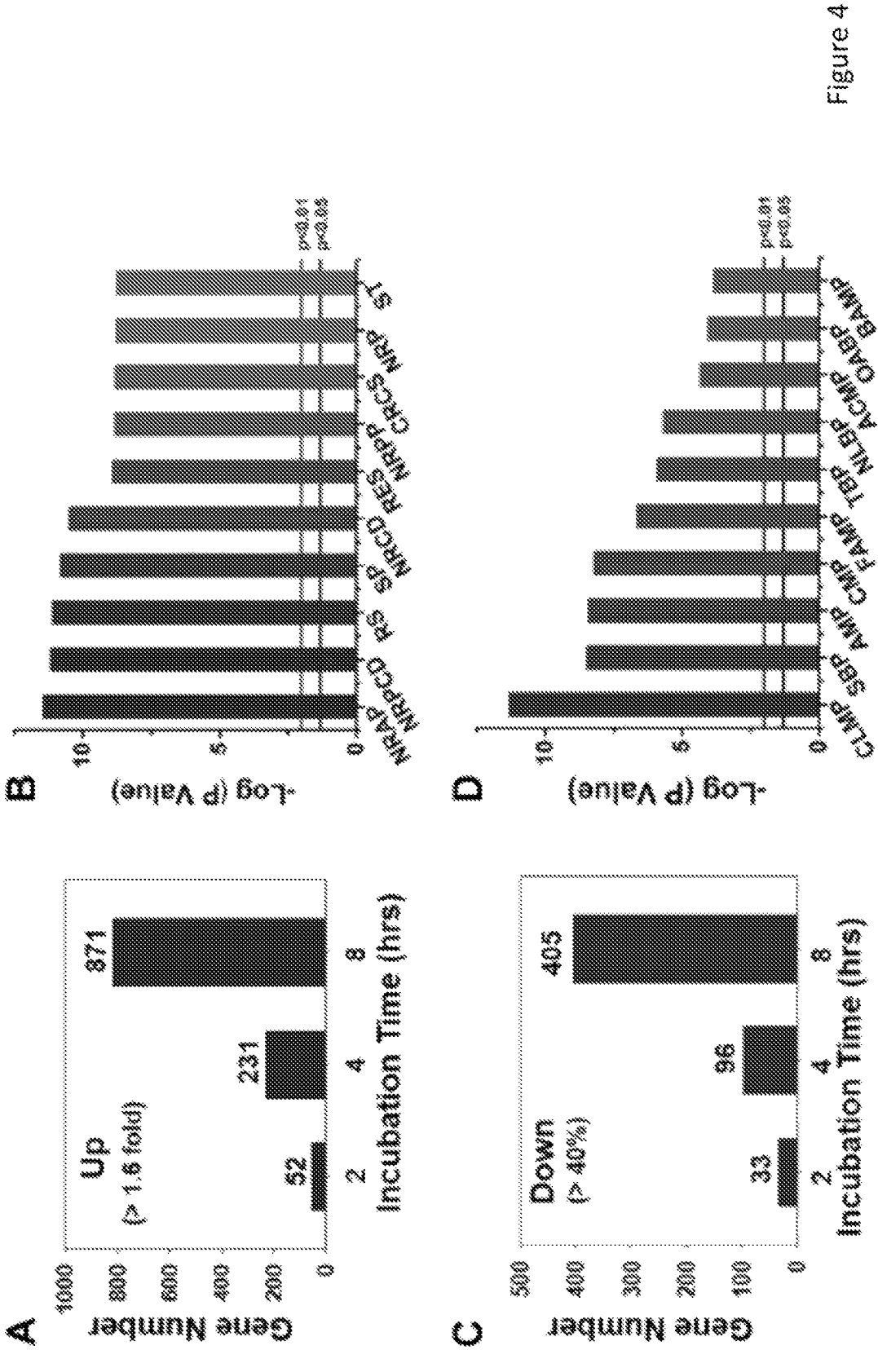
Figure 4:
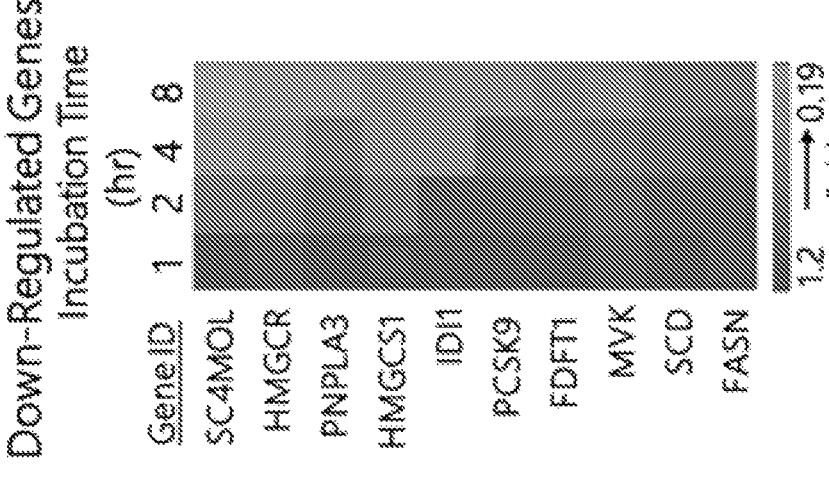
Figure 4:
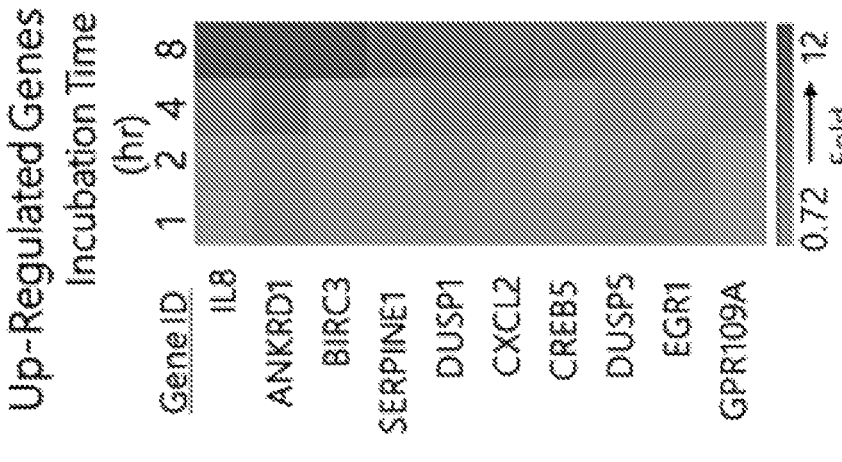

To examine the effect of 25HC3S on whole gene expression in human hepatocytes, human Genome U133Aplus2.0 Genechip® array analysis of 38,500 full length genes and EST (expressed sequence tags) clusters showed that treatment with 25HC3S in HpG-2 cells significantly modulated many clusters of gene expressions. The major clusters affected are genes involved in cholesterol and triglyceride metabolism, cell survival, and inflammation. Genes associated with cholesterol and triglyceride biosynthesis were significantly down-regulated, while genes associated with cell survival, proliferation, and anti-oxidization were significantly upregulated as shown in FIG. 4. Altogether, 25HC3S modulated the transcription of 1,276 genes (>1.6 fold) in a time-dependent manner. Genetic analysis of different GO processes, a collection of genes associated with a specific biological functional process, revealed that at 8 hours, the majority of up-regulated pathways are involved in cell survival (FIG. 4A and B); in contrast, majority of down-regulated genes are involved in lipid metabolism (FIG. 4C and D). The up-regulated genes related with anti-apoptosis (increased by 3 to 12-fold at 8 hours) are listed in FIG. 4E; and the down-regulated genes related with lipid metabolism (decreased by 50% to 95%) are listed in FIG. 4F. The detailed individual up-regulated genes are listed in Table 1.7; the down-regulated genes are listed in Table 1.8. Many studies have shown that epigenetic modification could globally regulate gene expression involved in vital cellular functions, including metabolism, inflammation, and cell death/proliferation. Our data demonstrates that 25HC3S epigenetically regulates gene expressions via DNA $^{5m}$CpG demethylation in promoter regions.

TABLE 1.7

Up Regulated Gene List of Huh-7 Cells Treated by 25HC3S for 8 hours.

| Gene Symbol | Fold Change | Gene Name or Function |
|---|---|---|
| IL8 | 11.91 | Interleukin 8 |
| ANKRD1 | 8.67 | Ankyrin Repeat Domain 1 |
| FSTL3 | 8.24 | Follistatin like 3 |
| CYR61 | 8.08 | Cysteine rich angiogenic inducer 61 |
| EDN1 | 8.03 | Endothelin 1 |
| C11orf96 | 6.30 | Description: chromosome 11 open reading frame 96 |
| BIRC3 | 5.81 | Baculoviral IAP repeat containing 3 |
| IL11 | 5.53 | Interleukin 11 |
| HBEGF | 4.43 | Heparin binding EGF like growth factor |
| CYP24A1 | 4.33 | Cytochrome P450 family 24 subfamily A member 1 |
| SERPINE1 | 4.20 | Serpin family E member 1 |
| DDIT3 | 4.10 | DNA damage inducible transcript 3 |
| ATF3 | 4.08 | Activating transcription factor 3 |
| HSPA6 | 3.92 | Heat shock protein family A (Hsp70) member 6 |
| TNS1 | 3.89 | Tensin 1 |
| DUSP1 | 3.88 | Dual specificity phosphatase 1 |
| KLF5 | 3.88 | Kruppel like factor 5 |
| THBS1 | 3.82 | Thrombospondin 1 |
| SLC2A14 | 3.73 | Solute carrier family 2 member 14 |
| PMAIP1 | 3.65 | Phorbol-12-myristate-13-acetate-induced protein 1 |
| CXCL2 | 3.63 | Chemokine (C-X-C motif) ligand 2 |
| KRTAP3-1 | 3.49 | Keratin associated protein 3-1 |
| SKIL | 3.36 | SKI like proto-oncogene |
| AKAP12 | 3.30 | A-kinase anchoring protein 12 |
| TCIM | 3.29 | Transcriptional and immune response regulator |
| ICAM1 | 3.22 | Intercellular adhesion molecule 1 |
| GABBR1 | 3.20 | Gamma-aminobutyric acid type B receptor subunit 1 |
| UBASH3B | 3.15 | Ubiquitin associated and SH3 domain containing B |
| SOCS2 | 3.15 | Suppressor of cytokine signaling 2 |
| CREB5 | 3.12 | CAMP responsive element binding protein 5 |

TABLE 1.8

Down Regulated Gene List of Huh-7 Cells Treated by 25HC3S for 8 hours.

| Gene Symbol | Percentage Change (%) | Gene name or function |
|---|---|---|
| SC4MOL | −81.12 | Methylsterol monooxygenase 1 |
| SLCO4C1 | −72.30 | Solute carrier organic anion transporter family member 4C1 |
| HMGCR | −71.32 | 3-hydroxy-3-methylglutaryl-CoA reductase |
| PNPLA3 | −70.45 | Patatin like phospholipase domain containing 3 |
| ANKRD43 | −69.19 | Sosondowah ankyrin repeat domain family member A |
| HMGCS1 | −67.71 | 3-hydroxy-3-methylglutaryl-CoA synthase 1 |
| TUBB8 | −67.29 | Tubulin beta 8 class VIII |
| IDI1 | −66.48 | Isopentenyl-diphosphate delta isomerase 1 |
| TNFSF10 | −65.42 | TNF superfamily member 10 |
| NCMAP | −65.26 | Non-compact myelin associated protein |
| RHOBTB1 | −64.85 | Rho related BTB domain containing 1 |
| EHHADH | −64.46 | Enoyl-coa hydratase and 3-hydroxyacyl coa dehydrogenase |
| SQLE | −64.42 | Squalene epoxidase |
| PCSK9 | −62.51 | Proprotein convertase subtilisin/kexin type 9 |
| KANK4 | −61.28 | KN motif and ankyrin repeat domains 4 |
| SPTLC3 | −60.32 | Serine palmitoyltransferase long chain base subunit 3 |
| PAQR8 | −60.05 | Progestin and adipoq receptor family member 8 |
| RALGPS1 | −59.86 | Ral GEF with PH domain and SH3 binding motif 1 |
| MAP2K6 | −59.78 | Mitogen-activated protein kinase kinase 6 |
| ZNF385B | −58.25 | Zinc finger protein 385B |
| PLPPR1 | −57.91 | Phospholipid phosphatase related 1 |
| SEC16B | −57.72 | SEC16 homolog B, endoplasmic reticulum export factor |
| ID3 | −57.51 | Inhibitor of DNA binding 3, HLH protein |
| VAV3 | −57.09 | Vav guanine nucleotide exchange factor 3 |
| KLLN | −56.31 | Killin, p53 regulated DNA replication inhibitor |
| SCN1A | −56.24 | Sodium voltage-gated channel alpha subunit 1 |
| PLA2G12B | −56.10 | Phospholipase A2 group XIIB |
| FRMD3 | −55.75 | FERM domain containing 3 |
| ID4 | −55.58 | Inhibitor of DNA binding 4, HLH protein |
| SLCO2B1 | −55.27 | Solute carrier organic anion transporter family member 2B1 |
| KLB | −54.22 | Klotho beta |
| FABP1 | −54.20 | Fatty acid binding protein 1 |
| SORBS2 | −53.92 | Sorbin and SH3 domain containing 2 |
| POU2AF1 | −53.59 | POU class 2 homeobox associating factor 1 |
| METTL7A | −53.26 | Methyltransferase like 7A |
| RAB11FIP4 | −53.16 | RAB11 family interacting protein 4 |
| MAT1A | −53.04 | Methionine adenosyltransferase 1A |
| CELSR2 | −53.00 | Cadherin EGF LAG seven-pass G-type receptor 2 |
| AGTR1 | −52.98 | Angiotensin II receptor type 1 |
| ELOVL6 | −52.72 | ELOVL fatty acid elongase 6 |
| MVK | −52.63 | Mevalonate kinase |
| CYB5B | −52.60 | Cytochrome b5 type B |
| CYP51A1 | −52.40 | Cytochrome P450 family 51 subfamily A member 1 |
| FDFT1 | −52.07 | Farnesyl-diphosphate farnesyl-transferase 1 |
| PRLR | −51.88 | Prolactin receptor |
| ALAD | −51.76 | Aminolevulinate dehydratase |
| PAQR9 | −51.51 | Progestin and adipoq receptor family member 9 |
| FMC1 | −51.27 | Formation of mitochondrial complex V assembly factor 1 homolog |

37

TABLE 1.8-continued

Down Regulated Gene List of Huh-7 Cells
Treated by 25HC3S for 8 hours.

| Gene Symbol | Percentage Change (%) | Gene name or function |
|---|---|---|
| P2RY8 | −50.91 | P2Y receptor family member 8 |
| TAB3 | −50.37 | TGF-beta activated kinase 1 (MAP3K7) binding protein 3 |
| ADH6 | −50.18 | Alcohol dehydrogenase 6 (class V) |
| NAP1L5 | −50.17 | Nucleosome assembly protein 1 like 5 |
| TMEM170B | −50.02 | Transmembrane protein 170B |

The Calcium, AMPK, and PPAR signaling pathways are ones involved in regulation of energy, lipids, and carbohydrate metabolisms. The $Ca^{2+}$/calmodulin-dependent protein kinase (CaMKK) and AMPK signaling pathway increases expression and decreases acetylation of PGC-la, which regulates mitochondrial biogenesis and lipid metabolism. The data shown in Example 1 from analysis of Whole Genome-Wide DNA Methylation (genomic level) and transcriptional Array of Human Genome U133Aplus2.0 Genechip® (mRNA level) showed that 25HC3S treatment significantly demethylated $^{5m}$CpG in the promoter regions of key genes including calcium channels, as well as genes of CaMKK and AMPK, increased their expression, and modulated downstream elements. These results provided evidence that 25HC3S globally regulated metabolic pathways mainly via the Calcium-AMPK signaling pathway as shown in FIG. 5. 25HC and 25HC3S are potent modulators in regulating DNA methylation. 25HC methylates CpG, and 25HC3S demethylates $^{5m}$CpG, while also down- and up-regulating expression of the key genes. PGC-la is a key regulator of mitochondrial biogenesis, oxidative phosphorylation, and mitochondrial antioxidant defense, and it is also responsible for maintaining metabolic homeostasis. PGC-la expression is up-regulated by the CREB protein and the AMPK signaling pathway. The present finding shows that 25HC3S up-regulates expression of CREB and AMPK via demethylating $^{5m}$CpG in their promoter regions, and subsequently increases intracellular PGC-la levels (FIG. 3), which provides a detailed mechanism for how 25HC3S functions as proposed in FIG. 5. 25HC3S suppresses DNMTs activities and demethylates $^{5m}$CpG in the key promoter regions. The demethylation up-regulates gene expression and increases MAPK-CREB signalings, which blocks cell apoptosis, induces cell proliferation. The demethylation also up-regulates calcium-AMPK signaling, resulting in inhibition of SREBP-1 activity by which inhibits fatty acid and triglyceride biosynthesis, and inhibition of HMGCR expression, decreases in cholesterol biosynthesis, and increases in the levels of malnonyl-CoA as shown FIG. 5.

Conclusion

The oxysterol sulfate, 25-hydroxycholesterol-3-sulfate (25HC3S) has been shown in this example to play an important role in lipid metabolism, inflammatory response, and cell survival. Example 1 provides a study of the molecular mechanism by which 25HC3S functions as an endogenous epigenetic regulator. The kinetic study of epigenetic enzymes demonstrated that 25HC3S specifically inhibited DNA methyltransferases, DNMT1, DNMT3a, and DNMT3b with IC50=4.04, 3.03, and 9.05×10-6 M, respectively. In human hepatocytes, high glucose induces lipid accumulation by increasing promoter CpG methylation of key genes involved in development of non-alcoholic fatty liver diseases (NAFLD). Using this model, 25HC3S converted the 5mCpG to CpG in the promoter regions of 1074 genes involved in 79 KEGG pathways.

Expression of the demethylated genes, which are involved in the master signaling pathways, including MAPK-ERK, calcium-AMPK, and type II diabetes mellitus pathways, increased. Messenger RNA array analysis showed that the up-regulated genes encoding for key elements in keeping cell survival and the down-regulated genes encoding for key enzymes in decreasing lipid biosynthesis. The results shown in Example 1 indicate that the expression of these elements and enzymes are regulated by the demethylated signaling pathways, and 25HC3S DNA demethylation of 5mCpG in promoter regions is a potent regulatory mechanism.

Example 2

Overview

The present Example was a randomized, dose ranging, single dose safety and pharmacokinetic study of 25HC3S administered to subjects with NASH and control healthy subjects. This study was conducted in 2 successive cohorts evaluating 2 single-dose levels of oral 25HC3S. For each cohort, 10 subjects with NASH were enrolled which were further classified into cirrhotic and non-cirrhotic. Each subject received only one dose of study treatment. The second cohort was dosed after a review of safety and tolerability data from Cohort 1. Cohort 1 received 50 mg of 25HC3S sodium and Cohort 2 received 200 mg of 25HC3S sodium.

Results

Figure 3:
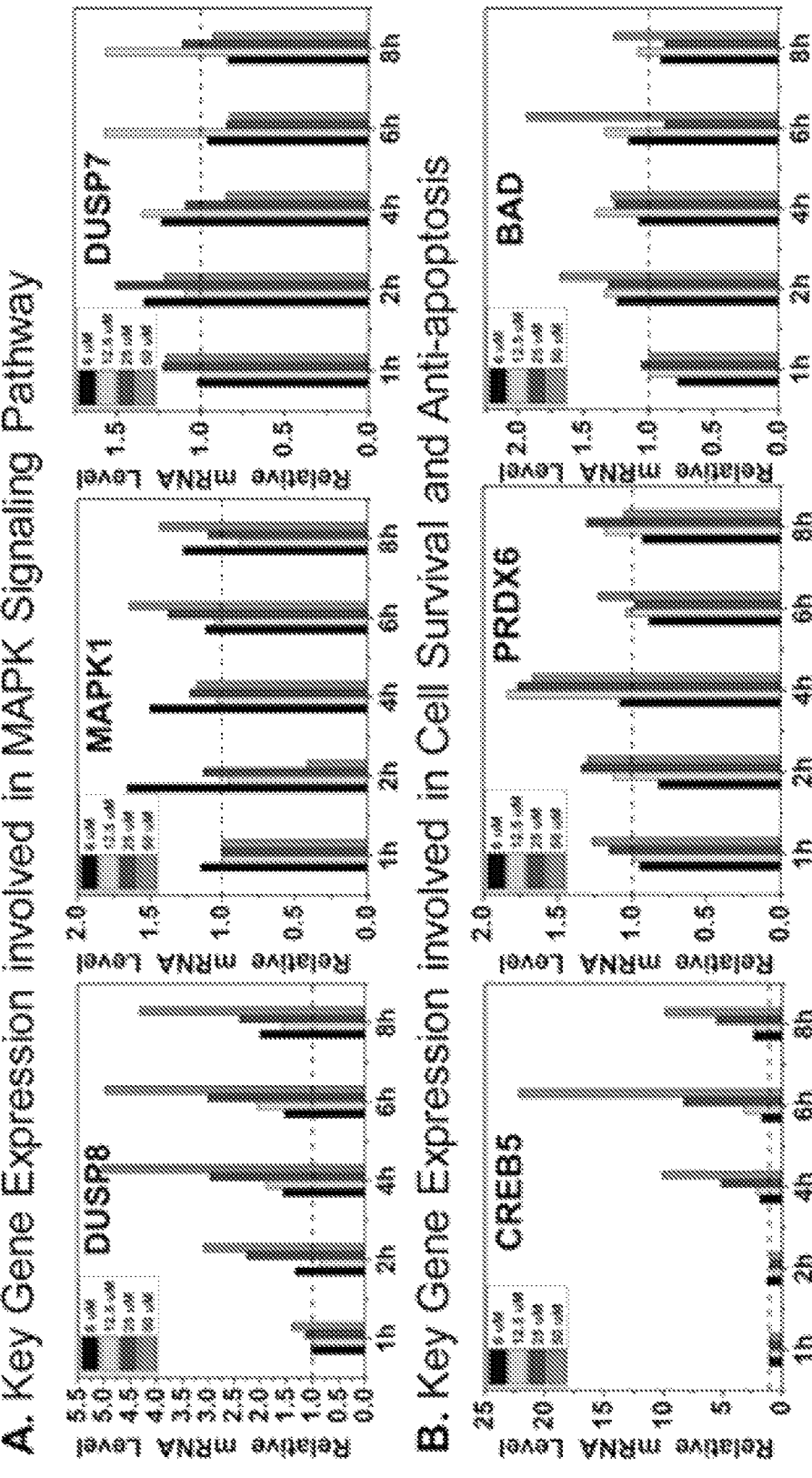
Figure 3:
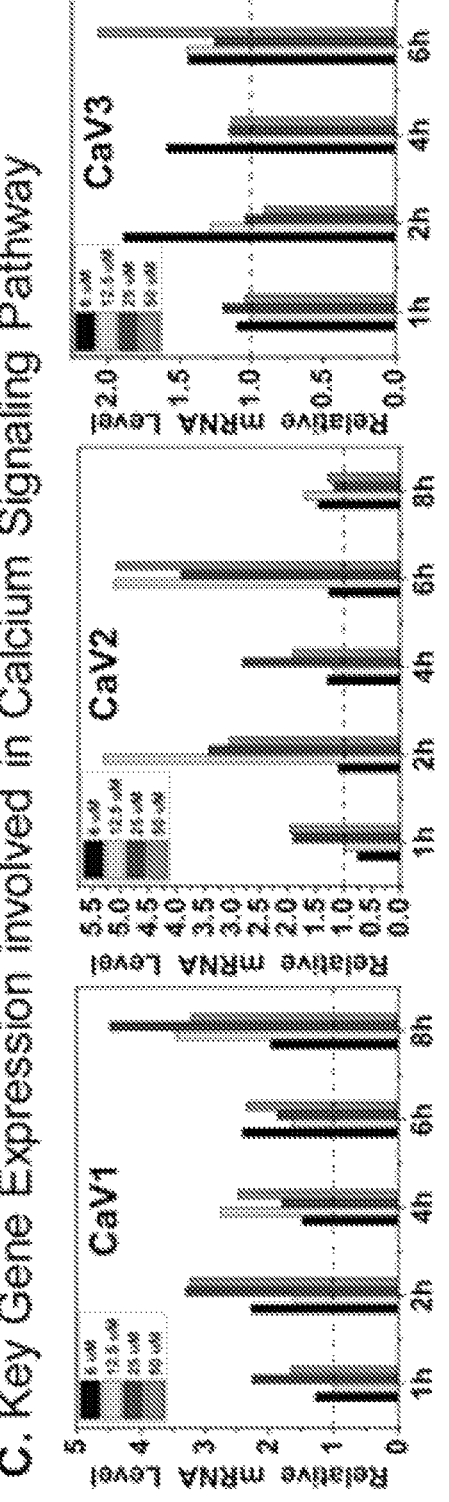
Figure 3:
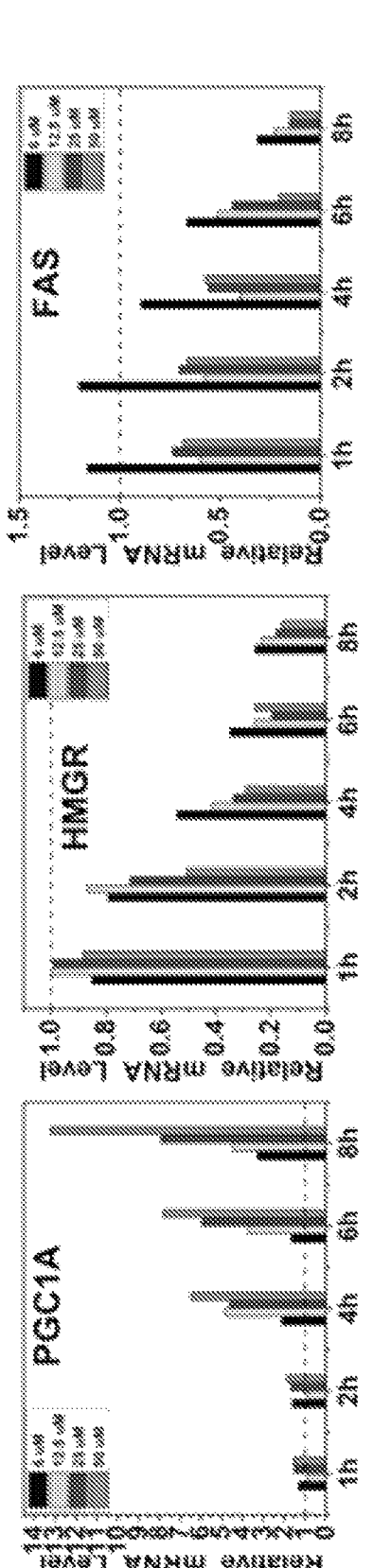

Pharmacokinetic (PK) plasma concentrations of 25HC3S are summarized in Table 2.1 (50 mg dose) and Table 2.2 (200 mg dose) below. Plasma 25HC3S levels were detectable up to 12 hours post-dose for Cohort 1 healthy subjects and up to 16 hours post-dose in Cohort 2 healthy subjects (Table 2.1). The plasma profiles were similar for both healthy and NASH subjects following administration of 50 mg 25HC3S (FIG. 2) and 200 mg 25HC3S (FIG. 3). For healthy subjects, a four-fold increase in dose resulted in an approximate three-fold increase in mean $C_{max}$ (50 mg dose: 93.967±27.343 ng/mL and 200 mg dose: 260.500±54.779 ng/mL). This was also observed for AUC parameters (Tables 2.1 and 2.2). Similarly, NASH subjects also displayed an approximate three-fold increase in both $C_{max}$ and AUC parameters for a four-fold increase in dose (Tables 2.1 and 2.2). Mean % $AUC_{exp}$ was low, suggesting that the blood sampling schedule was adequate to capture the majority of the AUC where it was possible to compute.

Individual plasma overlay plots indicated that despite differing subject numbers for healthy (n=6) and NASH (n=10) subjects, the NASH subjects tended to display a greater variability for $C_{max}$ and AUC parameters. In NASH subjects, geometric mean $C_{max}$ increased by 18-24% over healthy subjects for Cohorts 1 and 2 which was accompanied by a 25-50% higher CV % geometric mean in NASH subjects (Table 2.1). Geometric mean $AUC_{0-12}$ and $AUC_{0-last}$ were similar between NASH and healthy subjects in Cohort 1 but tended to be approximately 30% higher in Cohort 2, where the % CV was 50% higher in NASH subjects. $AUC_{0-inf}$ (Cohort 2) was approximately 20% higher in NASH subjects. Hence, when the higher % CV was taken into account, no clear difference between healthy and NASH subjects in terms of $C_{max}$ and AUC was concluded (Table 2.1).

TABLE 2.1

| Health Status | Subject No. | $T_{1/2}$ (h) | $T_{max}$ (h) | $C_{max}$ (ng/mL) | $AUC_{0-12}$ (h * ng/mL) | $AUC_{0-last}$ (h * ng/mL) | $AUC_{inf}$ (h *ng/mL) | $V_z/F$ (L) | CL/F (L/h) |
|---|---|---|---|---|---|---|---|---|---|
| | | | | Cohort 1 (50 mg 25HC3S sodium): Pharmacokinetic Parameters | | | | | |
| Healthy | N | 2 | 6 | 6 | 4 | 6 | 2 | 2 | 2 |
| | Mean | 1.906 | 3.008 | 93.967 | 528.0 | 477.1 | 438.6 | 324.96 | 122.35 |
| | SD | 0.350 | 1.105 | 27.347 | 217.6 | 190.7 | 161.9 | 62.41 | 45.16 |
| | Geometric Mean | 1.889 | 2.834 | 90.946 | 496.7 | 450.0 | 423.3 | 321.95 | 118.11 |
| | CV % Geometric Mean | 18.62 | 39.63 | 28.03 | 41.67 | 37.58 | 39.18 | 19.51 | 39.18 |
| NASH | N | 5 | 10 | 10 | 5 | 10 | 5 | 5 | 5 |
| | Mean | 1.674 | 2.408 | 113.170 | 623.1 | 513.3 | 636.1 | 203.28 | 85.29 |
| | SD | 0.136 | 0.844 | 36.261 | 217.5 | 219.3 | 231.5 | 48.28 | 23.57 |
| | Geometric Mean | 1.670 | 2.305 | 107.627 | 597.8 | 476.1 | 608.3 | 198.01 | 82.19 |
| | CV % Geometric Mean | 8.03 | 29.81 | 35.26 | 31.66 | 42.20 | 32.82 | 27.09 | 32.82 |

TABLE 2.2

| Health Status | Subject No. | $T_{1/2}$ (h) | $T_{max}$ (h) | $C_{max}$ (ng/mL) | $AUC_{0-12}$ (h * ng/mL) | $AUC_{0-last}$ (h * ng/mL) | $AUC_{inf}$ (h * ng/mL) | $V_z/F$ (L) | CL/F (L/h) |
|---|---|---|---|---|---|---|---|---|---|
| | | | | Cohort 1 (200 mg 25HC3S sodium): Pharmacokinetic Parameters | | | | | |
| Healthy | N | 6 | 6 | 6 | 6 | 6 | 6 | 6 | 6 |
| | Mean | 1.753 | 2.673 | 260.500 | 1175.9 | 1185.7 | 1194.3 | 434.05 | 171.25 |
| | SD | 0.388 | 1.028 | 54.779 | 189.4 | 192.4 | 192.1 | 128.07 | 28.60 |
| | Geometric Mean | 1.719 | 2.528 | 255.698 | 1162.8 | 1172.5 | 1181.2 | 419.93 | 169.32 |
| | CV % Geometric Mean | 21.50 | 36.69 | 21.46 | 16.66 | 16.61 | 16.50 | 28.05 | 16.50 |
| NASH | N | 7 | 10 | 10 | 10 | 10 | 7 | 7 | 7 |
| | Mean | 2.511 | 2.906 | 332.700 | 1541.0 | 1581.6 | 1428.5 | 540.23 | 143.19 |
| | SD | 1.751 | 1.198 | 99.454 | 417.9 | 413.9 | 247.0 | 457.19 | 21.67 |
| | Geometric Mean | 2.196 | 2.647 | 318.582 | 1495.2 | 1539.2 | 1411.8 | 448.71 | 141.66 |
| | CV % Geometric Mean | 53.22 | 51.05 | 32.61 | 25.82 | 24.23 | 16.28 | 62.39 | 16.28 |

Hepatic stiffness by transient elastography (TE) and magnetic resonance elastography (MRE), measured before and after dosing, changed by −11% (TE) or −6% (MRE) in the 50 mg, −7% (TE) or 4% (MRE) in the 150 mg, and −2% (TE) or 0% (MRE) in the 600 mg groups.

At the end of 4-week dosing, plasma levels of pro-C3, a liver fibrosis marker, were decreased from baseline by −8%, −1%, and −5% in the groups administered 50 mg, 150 mg, and 600 mg, respectively. At 2-week post-dose follow-up, pro-C3 levels were −7%, 8%, and 1% from baseline in the groups administered 50 mg, 150 mg, and 600 mg, respectively.

Overall improvement was also observed in insulin resistance by homeostatic model assessment for insulin resistance (HOMA-IR) after 4-week 25HC3S treatment. At the end of dosing, HOMA-IR was −22%, −18%, and 1% from baseline in the groups administered 50 mg, 150 mg, and 600 mg, respectively. At 2-week post-dose follow-up, it was −10% from baseline in the group administered 50 mg, and 17% and 3% in the groups administered 150 mg and 600 mg, respectively. These results are shown in more detail in FIG. 8 and Table 2.3:

TABLE 2.3

| Median (% from Baseline) | 50 mg/day | | | 150 mg/day | | | 600 mg/day | | |
|---|---|---|---|---|---|---|---|---|---|
| | Daily Dosing | | Follow-up | Daily Dosing | | Follow-up | Daily Dosing | | Follow-up |
| | 2 week | 4 week | 6 week | 2 week | 4 week | 6 week | 2 week | 4 week | 6 week |
| | Insulin Resistance | | | | | | | | |
| All Subjects | −4.7 | −21.6 | −10.5 | 0 | −18.0 | 17.1 | 9.4 | 0.8 | 2.8 |
| n | 23 | 21 | 20 | 21 | 21 | 20 | 21 | 20 | 21 |

TABLE 2.3-continued

| | | | | | | | | | |
|---|---|---|---|---|---|---|---|---|---|
| | Insulin Resistance | | | | | | | | |
| | 50 mg/day | | | 150 mg/day | | | 600 mg/day | | |
| Median | Daily Dosing | | Follow-up | Daily Dosing | | Follow-up | Daily Dosing | | Follow-up |
| (% from Baseline) | 2 week | 4 week | 6 week | 2 week | 4 week | 6 week | 2 week | 4 week | 6 week |
| Subjects with ≥-10% in PDFF | −12.8 | −20.9 | 8.9 | −13.8 | −10.9 | 22.7 | 15.2 | 2.4 | 20 |
| n | 9 | 9 | 9 | 9 | 9 | 9 | 9 | 9 | 9 |

The results shown in Table 2.3 are surprising, especially for the 50 mg/day and 150 mg/day doses. The magnitude of the effect of 25HC3S on insulin resistance was surprising. Relative to other diabetes drugs, the magnitude of effect on insulin resistance was relatively high considering the short duration of 25HC3S dosing. Compare the results of Table 2.3 with those of other drugs shown in Table 2.4.

sodium was administered to healthy subjects or NASH patients.

In addition, the magnitude of the effect of 25HC3S on insulin resistance was surprising. Relative to other diabetes drugs, the magnitude of effect on insulin resistance was relatively high considering the short duration of 25HC3S dosing.

TABLE 2.4

| | | | | |
|---|---|---|---|---|
| 4 Effect on Insulin Resistance of Other Drugs | | | | |
| Drug | MOA | Clinical Trial | Tx Duration | HOMA-IR |
| Semaglutide (Subcutaneous) | Glucagon-like peptide-1 (GLP-1) analog | SUSTAIN 1-3 T2D | 30 weeks Or 56 weeks | 0.5 mg (27% to 36%) 1.0 mg (32% to 46%) comparators (17% to28%) |
| Rosiglitazone (Oral) | Thiazolidinedione PPRA-gamma activator | Research study 250 pts Placebo-controlled study 493 pts | 5-6 months 26 weeks | HOMA-IR index 2.82 +/− 1.94 vs. 2.01 +/− 1.58 2 mg bd 16% 4 mg bd 24.6% |
| Saxagliptin (Oral) | Dipeptidyl peptidase-4 (DPP-4) inhibitor | Clinical trial Vs. SOC 102 pts | 3, 6, 12-months | P < 0.001 at 3-, 6-, and 12-months vs. baseline |
| Dapagliflozin (Oral) | Sodium-glucose cotransporter 2 (SGLT2) inhibitor | Placebo-controlled Research study 15 pts | 1 week | 10 mg once daily for 1 week 4.52 ± 2.27 to 3.78 ± 1.59 (P 0.044) |

Conclusions

This report presents pharmacokinetics of 25HC3S following oral administration to normal healthy and NASH subjects at the doses 50 mg (Cohort 1) to 200 mg (Cohort 2). Healthy subjects in Cohort 2 provided sufficient data to enable CL/F to be determined at 171.25±28.60 L/h and Vz/F at 434.05±128.07 L. This was supported by $T_{1/2}$ results which remained relatively constant with mean values ranging from 1.674 hours to 2.511 hours across both healthy and NASH subject groups. $AUC_{0-last}$ and $AUC_{inf}$ were consistent within cohorts and tended, along with $C_{max}$, to increase in a less than proportional manner with increasing 25HC3S dose.

An 18-24% increase in $C_{max}$ (geometric mean) was observed for NASH over healthy subjects. However, the greater CV % geometric mean for NASH subjects made this observation inconclusive. Similarly, when exposure (AUC parameters) was considered, potential increasing trends in NASH subjects (up to 31%) were countered by higher CV % geometric mean. Hence, it was concluded that no clear difference in pharmacokinetics occurred whether 25HC3S Example 3

Objective

The objectives of this study were to determine the plasma pharmacokinetics of [4-$^{14}$C]-25HC3S-derived radioactivity in male Sprague Dawley rats, determine the routes of elimination and excretion mass balance of [4-$^{14}$C]-25HC3S-derived radioactivity in male Sprague Dawley rats, determine the tissue distribution and tissue pharmacokinetics of [4-$^{14}$C]-25HC3S-derived radioactivity using quantitative whole body autoradiography methods in male Sprague Dawley and Long Evans rats following a single intravenous (bolus) dose, and to provide plasma, urine, and fecal homogenate samples for metabolite profiling of [4-$^{14}$C]-25HC3S-derived radioactivity.

Study Design

Nine male Sprague Dawley rats (Group 1) were designated for the pharmacokinetic phase, 3 male Sprague Dawley rats (Group 2) for the excretion mass balance phase, and 7 male Sprague Dawley rats (Group 3) and 9 male Long Evans rats (Group 4) for the tissue distribution phase. All animals received a single intravenous dose of [$^{14}$C]-25HC3S at 10 mg/kg and a target radioactivity of 225

μCi/kg. Blood samples were collected from all Group 1 animals at approximately 0.083, 0.25, 0.5, 1, 2, 4, 8, 12, 24, 48, and 72 hours post-dose. Urine and feces were collected from all Group 2 animals periodically through 168 hours post-dose. At approximately 0.083, 0.5, 1, 4, 8, 24, and 168 hours post-dose for Group 3 and at approximately 0.083, 0.5, 1, 4, 8, 24, 168, 336, and 504 hours post-dose for Group 4, 1 animal/group/time point was anesthetized with isoflurane and a blood sample collected. Following blood collection, animals were euthanized by $CO_2$ inhalation and carcasses frozen in a dry ice/hexane bath for processing by quantitative whole body autoradiography. Whole blood, plasma, urine, feces, cage rinse, and cage wash were analyzed for total radioactivity by liquid scintillation counting.

Results and Key Findings

After a single intravenous (bolus) dose of $[4\text{-}^{14}C]$-25HC3S administered to rats at 10 mg/kg, the mean plasma $C_0$ was 25,900 ng-equiv./g, and $AUC_{last}$ was 27,900 h*ng-equiv./g. The terminal elimination phase $T_{1/2}$ was 26.6 hours.

Based on the excretion data, approximately 100.2% of the dose administered was recovered over 168 hours in urine, feces, and cage rinse from rats following a single intravenous (bolus) dose of $[4\text{-}^{14}C]$-25HC3S at 10 mg/kg. The majority of the recovered radioactivity was in feces (83.0%), indicating that biliary excretion is the primary route of excretion in rats.

After a single intravenous (bolus) dose of $[4\text{-}^{14}C]$-25HC3S to male Sprague Dawley rats in Group 3 at 10 mg/kg, $[4\text{-}^{14}C]$-25HC3S and/or its metabolites were broadly distributed and detected by quantitative whole body autoradiography in all tissues except the eye (lens). Plasma concentrations were similar to those determined in the pharmacokinetics phase. The whole blood $C_{max}$ was 8530 ng-equiv/g, and $AUC_{last}$ was 25,200 h*ng-equiv./g. There was a negligible difference in plasma and whole blood exposure, as measured by the plasma:whole blood $AUC_{last}$ ratio of 0.79, indicating that the 25HC3S partitioned equally into plasma and blood cells. The $T_{1/2}$ was 44.3 hours in plasma and 52.2 hours in whole blood; differences in plasma $T_{1/2}$ between the PK phase and the QWBA phase are due to the difference in blood collection time points.

The $C_{max}$ and $AUC_{last}$ for $[4\text{-}^{14}C]$-25HC3S-derived radioactivity were highest in the liver: up to 87,900 ng-equiv./g and 364,000 h-ng/g, respectively. Kidney (all sections), small intestine (wall), lung, and adrenal gland concentrations ranged from 43,200 ng-equiv./g to 13,600 ng-equiv./g, higher than the maximum plasma concentration of 12,400 ng-equiv./g. Thymus, bone (femur), uveal tract, fat, testes, and brain concentrations were lowest relative to the other tissues: <5000 ng-equiv./g (around 1500 ng-equiv./g). Remaining tissues had concentrations between 5000 and 10,800 ng-equiv./g. The $T_{max}$ was most often 0.083 to 0.5 hours post-dose. Concentrations were below quantitation limit in all tissues except adrenal gland, harderian gland, liver, and small intestine by 168 hours post-dose. As calculated using $AUC_{last}$, the tissue:plasma ratios were high for liver and small intestine (wall) at 11.4 and 7.44, respectively. High liver and small intestine concentrations are consistent with extensive biliary (fecal) excretion following an intravenous dose. All other tissue:plasma ratios demonstrated limited affinity for remaining tissue types.

Administration of a single intravenous dose of $[4\text{-}^{14}C]$-25HC3S to male Long Evans rats at 10 mg/kg revealed no substantial difference in plasma or whole blood concentrations over the first 168 hours post-dose versus Sprague Dawley rats; plasma and whole blood concentrations were below quantitation limit in plasma and whole blood by 336 hours post-dose in pigmented animals. There appeared to be no difference in binding to pigmented or non-pigmented skin or the uveal tract; for all tissues, the concentrations were below quantitation limit by 168 hours post-dose.

Plasma, urine, and feces from rats were analyzed for determination of 25HC3S related radiolabeled materials. Samples were profiled using high performance liquid chromatography with radiodetection and metabolic characterization was performed using mass spectrometry and tandem mass spectrometry analysis.

Plasma pools were made from Group 1 rats at the 0.083, 0.25, 0.5, and 1-hour collection time points. From these Group 1 sample pools and from a Group 3 0.083-hour plasma sample, the largest component present in the 0.083- and 0.25-hour collections was attributed to the parent 25HC3S representing about 58% to 92% of the radioactivity. Three metabolites present at >10% of the radioactivity in the 0.5- and 1-hour collections were M14 (up to 15% relative observed intensity), M24 (up to 13% relative observed intensity), and M28 (up to 83% relative observed intensity). Among the time points with suitable radioactivity for metabolite profiling and characterization (up to 1 hour post-dose), approximately 54% of the exposure (AUC) to 25HC3S related radioactivity was attributable to 25HC3S, approximately 34% to M28, and the remainder to the minor metabolites.

Urine pools were prepared for Group 2 at 0 to 6 and 6 to 12 hours post-dose. The largest component present was attributed to the parent 25HC3S representing about 78% to 93% of the radioactivity. A total of 4 metabolites were identified, although no metabolites were present at >1.2% of dose or >10% relative observed intensity. Four metabolites present at <10% relative observed intensity in at least 1 sample were M7 (<5% relative observed intensity), M16 (<3% relative observed intensity), M19 (<6% relative observed intensity), and M25 (<5% relative observed intensity).

Feces pools were prepared for Group 2 at 0 to 12, 12 to 24, and 24 to 48 hours post-dose.

A total of fourteen metabolites were identified. Four metabolites present at >5% of dose were M1 (21% of dose and 23% to 30% relative observed intensity), M2 (7% of dose and 4% to 12% relative observed intensity), M3 (15% of dose and 13% to 23% relative observed intensity), and M4 (8% of dose and 6% to 12% relative observed intensity). Parent 25HC3S was present at 2% of dose (1% to 5% relative observed intensity).

The primary metabolic pathways involved oxidation of 25HC3S resulting in the conversion of the sulfate group to a hydroxyl group followed by further oxidation to form bile acid structures related to deoxycholic acid and cholic acid or their isomers. In addition, glutathione conjugation of deoxycholic acid (or an isomer of deoxycholic acid) was suggested by the presence of a metabolite having the corresponding molecular weight for that structure. Neither desmosterol sulfate nor 25-hydroxycholesterol was detected in any of the plasma, urine, or feces samples.

Example 4

After a single oral (gavage) dose of $[1^4C]$-25HC3S administered to rats at 75 mg/kg, plasma $C_{max}$ was 3800 ng equiv./g, and $AUC_{last}$ was 96,400 h-ng equiv./g. The terminal elimination phase $T_{1/2}$ was 27.3 hours.

Based on the excretion data, approximately 94.5% of the dose administered was recovered in urine, feces, and cage rinse from rats following a single oral (gavage) dose of [1⁴C]-25HC3S at 75 mg/kg. The majority of the recovered radioactivity was in feces (94.2%), indicating that biliary excretion is the primary route of excretion for absorbed 25HC3S in rats.

After a single oral (gavage) dose of [1⁴C]-25HC3S to male Sprague Dawley rats at 75 mg/kg, [1⁴C]-25HC3S and/or its metabolites were broadly distributed and detected by quantitative whole body autoradiography in all tissues except the eye (lens). No [1⁴C]-25HC3S-derived radioactivity was detected in the eye (lens). Plasma concentrations were similar to those determined in the pharmacokinetics phase, and were above the lower limit of quantitation. The whole blood $C_{max}$ was 2850 ng equiv/g, and $AUC_{last}$ was 127,000 h-ng equiv./g. There was a negligible difference in plasma and whole blood exposure, as measured by the plasma:whole blood $AUC_{last}$ ratio of 1.12, indicating that the 25HC3S partitioned approximately equally into plasma and blood cells.

For the tissues analyzed by quantitative whole-body autoradiography, the $C_{max}$ for [1⁴C]-25HC3S-derived radioactivity, where measurable, was highest in the small intestine (wall) followed by the stomach (wall): 424,000 ng equiv./g and 204,000 ng equiv./g, respectively. Pancreas and liver concentrations ranged from 23,500 ng equiv./g to 28,100 ng equiv./g. Uveal tract and brain concentrations were lowest relative to the other tissues and were approximately 1000 ng equiv./g. Skin, thymus, prostate, and pituitary tissue concentrations were <3000 ng equiv./g. Remaining tissues had concentrations between 3600 ng-equiv./g and 10,700 ng equiv./g. The $T_{max}$ was 6 hours post-dose or less. By 168 hours post-dose, tissue concentrations were near or below the quantitation limit in all tissues except adrenal gland and liver. As calculated using $AUC_{last}$, the tissue:plasma ratios were highest for the small intestine (wall, 15.4) followed by the liver and adrenal gland at 6.96 and 6.64, respectively. High liver and small intestine concentrations are consistent with oral administration and biliary (fecal) excretion. All other tissue:plasma ratios demonstrated limited affinity for remaining tissue types.

Radiolabeled components in plasma and feces extracts were profiled and identified using radio-high performance liquid chromatography (HPLC) and high performance liquid chromatography/mass spectrometry (HPLC/MS) methods.

There were no urine samples that contained sufficient radioactivity to require metabolite profiling and identification.

Plasma pools were prepared for Group 1 (75 mg/kg, [14C]-25HC3S) samples collected at 2, 4, and 6 hours post-dose. In the 2 hour post-dose plasma, the primary radiolabeled component was parent 25HC3S which was present at 63% relative observed intensity (ROI) and a concentration of 2090 ng-equiv./g. One metabolite M29 was identified as 25-hydroxycholesterol with 37% ROI and a concentration of 1233 ng-equiv./g. The plasma collections at 4 and 6 hours post-dose did not contain sufficient concentrations for radioprofiling.

Feces pools were prepared for Group 2 (75 mg/kg, [1⁴C]-25HC3S) samples collected from 0 to 24, 24 to 48, 48 to 72, 72 to 96, 96 to 120, 120 to 144, and 144 to 168 hours post-dose. A total of eleven metabolites were identified. None of the metabolites were present at >5% of dose. Metabolites present at 2-5% of dose were M1 (4.5% of total dose and 1%-69% ROI), M3 (4.6% of total dose and 1%-44% ROI), M4 (2.0% of total dose and 0%-10% ROI), M8 (3.1% of total dose and 1%-46% ROI), M29 (1.9% of total dose and 0%-2% ROI), and M30 (3.3% of total dose and 0%-5% ROI). The primary radiolabeled component was parent 25HC3S which was present at 71.1% of total dose (0%-88% ROI).

Radiolabeled desmosterol sulfate was not found in any of the plasma or feces samples.

The primary metabolic pathways involved oxidation of 25HC3S, resulting in the conversion of the sulfate group to a hydroxyl group followed by further oxidation to form bile acid structures related to deoxycholic acid and cholic acid or their isomers and 25-hydroxycholesterol.

Example 5

Overview

The present Example was a randomized, open label, multi center US study to evaluate safety, pharmacokinetics, and signals of biological activity of 4-week administration of 25HC3S in NASH patients with stage 1-3 fibrosis. A total of 63 patients completed the study with 21 patients per dose group (completion of MRI-PDFF measurement). 25HC3S sodium was orally administered daily at 50 mg, 150 mg, or 600 mg (300 mg BID). The patients in this trial were monitored for 2 weeks (14 days), dosed for 4 weeks (28 days), and followed up for an additional 4 weeks (28 days).

Title of Trial: A Randomized, Open-label, Phase 1b Study to Evaluate Safety, Pharmacokinetic and Pharmacodynamic Signals of 25HC3S in Patients with Non-Alcoholic Steatohepatitis (NASH)

Phase of Development: Phase 1b

Endpoints: To determine the safety and pharmacokinetics (PK) of 4 week daily oral dosing of 25HC3S in subjects with NASH To determine the effect of 25HC3S on pharmacodynamic (PD) signals in subjects with NASH Change of hepatic fat content from baseline* to end of dosing (end of Week 6) as measured by magnetic resonance imaging-proton density fat fraction (MRI-PDFF)

Change of hepatic stiffness from baseline to end of dosing (end of Week 6) as measured by transient elastography (TE)

Liver function parameters as measured by plasma alanine aminotransferase (ALT), aspartate aminotransferase (AST), and gamma-glutamyl transpeptidase (GGT) from baseline to end of dosing (end of Week 6), weekly during the 4 weeks of dosing, and end of the study (end of Week 10); the panel will be part of laboratory safety tests Metabolic panels as measured by serum cholesterol, low density lipoprotein cholesterol (LDL-C), high density lipoprotein cholesterol (HDL) and triglycerides (TG) from baseline to end of dosing (end of Week 6), weekly during the 4 weeks of dosing, and end of the study (end of Week 10)

Baseline is defined as the last non-missing value before the first dose of study drug Safety Assessments: Adverse Events (AEs) were recorded from the time of signing the informed consent form through the end of study or early termination visit respectively:

Vital Signs, Physical Examination and 12-lead ECG findings

Safety Laboratory Tests (chemistry, hematology, coagulation and urinalysis)

Trial Population: A total of 65 subjects (including both male and female), diagnosed with NASH or suspected NASH, were enrolled in the study. Each of the below dose groups included at least 20 patients.
Group 1: 50 mg 25HC3S sodium, oral QD
Group 2: 150 mg 25HC3S sodium, oral QD
Group 3: 300 mg 25HC3S sodium, oral BID
Inclusion Criteria: 1. Subjects provided written informed consent to participate in the study
2. Males or females subjects 18 years or older, at the time of signing informed consent
3. BMI 20-45 kg/m$^2$
4. Subjects had an historic histologic diagnosis of NASH, confirmed during the 12 months prior to the screening visit, demonstrating the presence of both Stage 1-3 fibrosis and a NAS≥4, with at least 1 point for each of the three components (steatosis, hepatocellular ballooning, and lobular inflammation), OR possessed a diagnosis of 'suspected NASH', using a combination of a clinical diagnosis*, laboratory results, and imaging assessments of steatosis (including MRI-PDFF>10% and CAP score>238 dB/m on Fibroscan® for heterogeneous livers) and fibrosis, the latter being defined in this clinical trial as:
 a. Value of Fibroscan®≥7 kPa
 OR
 b. MRE≥2.75 kPa
Clinical diagnosis of NASH was defined in this clinical trial as the existence of one or more of the following risk factors for NASH, namely:
 a. Type 2 diabetes or elevated fasting blood sugar
 b. Abdominal obesity
 c. Elevated lipid levels, especially elevated levels of serum triglycerides
 d. Hypertension, or
 e. Low levels of HDL cholesterol
5. For serum transaminases, ALT concentration for all patients at the time of screening was >1 and <5 times upper limit of normal (ULN) of the central lab in the absence of another cause of liver disease. If a patient had lab records in the past 6 months, ALT concentrations were <20 U/L female and <30 U/L male. AST concentration for all patients at the time of screening was <5× ULN
6. Serum ALT, AST, ALP, and TBL concentrations did not fluctuate>30% during the screening period
7. Platelet counts≥120,000/mm$^3$
8. Female subjects were eligible for the study if they met the following criteria:
 Are not pregnant or nursing
 Women of child-bearing potential (defined as females who are not surgically sterile or who are not over the age of 52 and amenorrheic for at least 12 months) must utilize appropriate birth control throughout the study duration. Acceptable methods that may be used are abstinence, birth control pills ("The Pill") or patch, diaphragm, IUD (coil), vaginal ring, condom, surgical sterilization or progestin implant or injection, or sexual activity limited to a sterile (e.g., vasectomized) male partner
9. Male participants agreed to consistently and correctly use a condom in combination with one of the above methods of birth control from enrolment to 30 days after the last dose of study medication
10. Participants were able to comply with dosing and able to complete the study schedule of assessments Results 25HC3S was well tolerated at all three doses with no drug related serious adverse events observed. PK parameters after repeat dosing were comparable to those after a single dose and were dose dependent.

Low and high dose groups showed statistically significant median reductions from baseline of serum ALT levels at −16% and −17%, respectively. The high dose group also showed statistically significant median reductions from baseline of serum AST (−18%) and GGT (−8%) levels, as well as FIB-4 (−15%) and APRI (−26%) scores. The low dose group had a statistically significant reduction at day 28 from baseline in liver stiffness as measured by Fibroscan (−10%).

Patients in the low and medium dose groups also had statistically significant median reduction at day 28 from baseline of serum triglycerides (−13% in the 50 mg group) or LDL-C(−11% in the 150 mg group). Patients with elevated baseline triglycerides (≥200 mg/dL; n=16) across all dose groups had a median reduction at day 28 from baseline of −24% (p<0.01).

In each dose group, 43% of patients who underwent MRI-PDFF, after 4-week dosing, showed≥10% liver fat reduction from baseline as measured by MRI-PDFF. The median reduction from baseline of liver fat in these patients in each sub-group, −18%, −19%, and −23%, respectively, were statistically significant. The reduction of liver fat content of each dose group was also accompanied by significant reduction of serum ALT levels. Each sub-group showed statistically significant median reduction from baseline of serum ALT levels at −21%, −19%, and −32%, respectively.

There was a 24% reduction in serum triglycerides in patients with elevated baseline triglycerides (≥200 mg/dL; n=16) across all dose groups at day 28 from baseline (p<0.01).

In the 43% of patients with >10% liver fat reduction by PDFF, both low and high dose 4-week 25HC3S treated patients also had statistically significant median reductions of AST (−24% and −39%), FIB-4 scores (−19% and −21%) and APRI scores (−27% and −36%), while the low dose treated patients also had a statistically significant median reduction of GGT (−13%) levels.

In addition, there were trended or statistically significant reductions of liver stiffness as measured by Fibroscan® in the 43% patients with ≥10% liver fat reduction by PDFF in all 3 dose groups (−7%, −9%, and −9%, respectively).

The results are summarized further in the following Tables:

| | 50 mg QD | 150 mg QD | 300 mg BID |
|---|---|---|---|
| Median | (n = 21-23) | (n = 20-21) | (n = 20-21) |
| ALT | −16%* | −10% | −17%*** |
| | (n = 22) | (n = 20) | (n = 20) |
| AST | −14% | −9% | −18%** |
| | (n = 22) | (n = 20) | (n = 20) |
| GGT | −6% | −1% | −8%* |
| | (n = 23) | (n = 20) | (n = 21) |
| LDL-C | −6% | −11%* | −7% |
| | (n = 22) | (n = 20) | (n = 21) |
| Non-HDL-C | −8% | −5% | −1% |
| | (n = 23) | (n = 20) | (n = 21) |

Top line Data Summary (Day 28 vs Baseline)
For all tables below, *indicates p-value < 0.05;
indicates p < 0.01; *indicates p < 0.001

-continued

Top line Data Summary (Day 28 vs Baseline)
For all tables below, *indicates p-value < 0.05;
indicates p < 0.01; *indicates p < 0.001

| Median | 50 mg QD (n = 21-23) | 150 mg QD (n = 20-21) | 300 mg BID (n = 20-21) |
|---|---|---|---|
| Triglycerides | −13%* | −3% | −2% |
| | (n = 23) | (n = 20) | (n = 21) |
| Platelet | +2% | +4% | +7%* |
| | (n = 22) | (n = 20) | (n = 19) |
| CK18, M30 | −14.6% | −8.6% | −16.1% |
| CK18, M65 | −18.1% | −9.9% | −35.0% |

ALT = alanine aminotransferase;

AST = aspartate aminotransferase;

GGT = Gamma-glutamyl transferase;

LDL-C ( Low-Density Lipoprotein-Cholesterol);

Non-HDL-C (Total cholesterol excluding High-Density Lipoprotein-Cholesterol);

QD (once a day);

BID (twice a day)

Non-Invasive Fibrosis Scores

| Median | 50 mg QD | 150 mg QD | 300 mg BID |
|---|---|---|---|
| FIB-4 | −6% | −4% | −15%** |
| APRI | −14% | −7% | −26%*** |

FIB 4 score is a non-invasive liver fibrosis assessment based on patient age, platelet count, AST and ALT values.
APRI (aspartate aminotransferase to platelet ratio index) is one of many different kinds of tests that are used to measure the levels of fibrosis and, in turn, cirrhosis of the liver.

Non-Invasive Imaging

| Median | 50 mg QD | 150 mg QD | 300 mg BID |
|---|---|---|---|
| MRI-PDFF | −7% | −7% | −4% |
| | (n = 21) | (n = 21) | (n = 21) |
| Fibroscan | −10%** | −9% | −1% |
| | (n = 22) | (n = 20) | (n = 21) |

MRI-PDFF is Magnetic Resonance Imaging-Proton Density Fat Fraction is a non-invasive measure of the proportion of liver tissue which is composed of fat.
FibroScan is a specialized ultrasound machine that measures the stiffness of liver tissue.

The following tables show Day 28 vs Baseline data in patients who had ≥10% reduction in MRI-PDFF
Clinical Chemistry
Patients with ≥10% Reduction in MRI-PDFF

| Median | 50 mg QD (n = 9) | 150 mg QD (n = 8) | 300 mg BID (n = 9) |
|---|---|---|---|
| ALT | −21%** | −19%* | −32%*** |
| AST | −24%** | −21% | −39%*** |
| GGT | −13%*** | −16%* | −14% |
| LDL-C | −7% | −11% | −8%* |
| Non-HDL-C | −10% | −8%* | −12%* |
| Triglycerides | −9% | 0% | −8% |
| Platelet | +6%* | −2% | +2% |
| CK18, M30 | −22.8%*** | −3.8% | −42.1%* |
| CK18, M65 | −28.1%*** | −8.7% | −55.8%* |

Non-Invasive Fibrosis Scores
Patients with ≥10% Reduction in MRI-PDFF

| Median | 50 mg QD | 150 mg QD | 300 mg BID |
|---|---|---|---|
| FIB-4 | −19%** | −6% | −21%*** |
| APRI | −27%*** | −16% | −36%*** |

Non-Invasive Imaging
Patients with ≥10% Reduction in MRI-PDFF

| Median | 50 mg QD (n = 9) | 150 mg QD (n = 9) | 300 mg BID (n = 9) |
|---|---|---|---|
| MRI-PDFF | −18%*** | −19%*** | −23%*** |
| Fibroscan | −7% | −9%** | −9% |

Biomarkers
% Change from baseline at the end of dosing (median at Day 28)

| Biomarker | 50 mg QD | 150 mg QD | 300 mg BID |
|---|---|---|---|
| Cytokeratin 18, M30 | −14.6 | −8.6 | −16.1 |
| Cytokeratin 18, M65 | −18.1 | −9.9 | −35.0 |
| C Reactive Protein | −13.9 | −11.8 | 1.7 |
| Plasminogen Activator Inhibitor-1 | −13.5 | −13.7 | −8.2 |
| Interleukin-1 Beta | −0.1 | −0.6 | −0.2 |
| Interleukin-6 | −6.0 | 1.7 | 5.4 |
| Interleukin-12 | 0.0 | 0.0 | 0.0 |
| Interleukin-17 | −1.3 | −16.4 | −0.8 |
| Interleukin-18 | −8.9 | −5.0 | −2.1 |
| Tumor Necrosis Factor | −3.2 | −2.9 | −7.9 |
| Bile Acid | 0.0 | 0.0 | 1.6 |
| Adiponectin | −1.6 | −3.8 | 3.9 |
| Adiponectin, HMW | 0.0 | 1.0 | 1.0 |

Pharmacokinetics

The pharmacokinetics of administered 25HC3S was determined. The mean (standard deviation) pharmacokinetic parameters are summarized in FIG. 9 and the table below.

Reference of Pharmacokinetic Parameters

The following PK parameters were estimated for 25HC3S from the plasma concentration data.

$C_{max}$ Maximum observed plasma concentration of 25HC3S $T_{max}$ The time (observed time point) of $C_{max}$ $C_{last}$ The last observed quantifiable concentration of 25HC3S in plasma $T_{last}$ The last observed time point of $C_{last}$ $AUC_{0-12}$ Area under the plasma concentration versus time curve from time zero to 12 h post-dose. Calculated by the linear/log trapezoidal rule.

$AUC_{0-last}$ Area under the plasma concentration versus time curve (linear/log trapezoidal rule) from time zero to the last measured concentration above the limit of quantitation.

$C_{min}$ Minimum observed concentration of 25HC3S.

$T_{last}$ The last (observed time point) of $C_{last}$ $AUC_{inf}$ The area under the concentration versus time curve (linear/log trapezoidal rule) extrapolated to infinite time, calculated as $AUC_{0-last}+(C_{last}/\lambda)$ % $AUC_{exp}$ Percentage of AUC extrapolated between $AUC_{0-last}$ and AUCinf $T_{1/2}$ An estimate of the terminal elimination half-life of the drug in plasma, calculated by dividing the natural log of 2 by the terminal elimination rate constant ($\lambda$)

λ First order rate constant associated with the terminal log-linear portion of the plasma concentration versus time curve.

CL/F The apparent clearance after administration of the drug: CL=Dose/$AUC_{inf}$, where 'Dose' is the dose of the drug.

$V_z$/F The apparent volume of distribution of 25HC3S.

| Pharmacokinetics | | | |
|---|---|---|---|
| Parameter | 50 mg QD (n = 22) | 150 mg QD (n = 21) | 300 mg BID (n = 21) |
| $C_{max}$ (ng/mL) | 79.1 (45.1) | 273.5 (187.7) | 429.7 (167.7) |
| $T_{max}$ (h) | 2.4 (1.0) | 2.0 (0.9) | 2.3 (2.4) |
| $T_{1/2}$ (h) | 2.7 (1.4) | 2.7 (1.4) | 2.4 (1.0) |
| $AUC_{(0-T)}$ (ng*h/mL) | 339.9 (113.9) | 1038.7 (542.5) | 2138.1 (1014.9) |
| CL/F (L/h) | 150.6 (51.5) | 176.6 (80.5) | 166.2 (60.4) |
| $V_z$/F (L) | 582.8 (338.2) | 669.1 (410.6) | 567.7 (297.1) |
| Metabolite/Drug Ratio | 0.04 (0.04) | 0.11 (0.03) | 0.12 (0.04) |

Prior to and during the study some of the subjects received a statin (atorvastatin, pravastatin, rosuvastatin, or simvastatin). The subjects receiving both 25HC3 and a statin had reduced triglycerides and non-HDL at day 28 after dosing as shown in the following Table:

| Patients | Mean TG to Baseline Mean | Mean Non-HDL to Baseline Mean | Median TG to Baseline Mean | Median Non-HDL to Baseline Mean |
|---|---|---|---|---|
| All on a statin (n = 20) | −2% | −9% | −6% | −9% |
| All on a statin except one outlier (n = 19) | −10% | −11% | −9% | −10% |

Conclusion

The present Example showed that the low dose resulted in reduced liver fat (e.g., as measured by MRI-PDFF) compared with higher doses. The present Example showed that the medium dose resulted in improved low density lipoprotein cholesterol (LDL-C) levels. The present Example showed that the high dose resulted in improved enzyme levels (e.g., ALT, AST, GGT) suggesting improved liver function.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. Moreover, nothing disclosed herein is intended to be dedicated to the public regardless of whether such disclosure is explicitly recited in the claims.

The scope of the present invention, therefore, is not intended to be limited to the exemplary embodiments shown and described herein. Rather, the scope and spirit of present invention is embodied by the appended claims. In the claims, 35 U.S.C. § 112(f) or 35 U.S.C. § 112(6) is expressly defined as being invoked for a feature in the claim only when the exact phrase "means for" or the exact phrase "step for" is recited at the beginning of such feature in the claim; if such exact phrase is not used in a feature in the claim, then 35 U.S.C. § 112(f) or 35 U.S.C. § 112(6) is not invoked.

The invention claimed is:

1. A method of treating insulin resistance in a human subject in need thereof, the method comprising orally administering to the subject at least one compound selected from 25-hydroxycholesterol-3-sulfate (25HC3S), 25-hydroxycholesterol-disulfate (25HCDS), 27-hydroxycholesterol-3-sulfate (27HC3S), 27-hydroxycholesterol-disulfate (27HCDS), 24-hydroxycholesterol-3-sulfate (24HC3S), 24-hydroxycholesterol-disulfate (24HCDS), and 24,25-epoxycholesterol-3-sulfate, or salt thereof in an amount ranging from 1 mg/day to 300 mg/day, wherein the human subject has a magnetic resonance imaging-proton density fat fraction (MRI-PDFF) prior to treatment of at least 5%, or a magnetic resonance elastography (MRE) prior to treatment≥2.75 kPa.

2. A method of treating diabetes in a human subject in need thereof, the method comprising orally administering to the subject at least one compound selected from 25-hydroxycholesterol-3-sulfate (25HC3S), 25-hydroxycholesterol-disulfate (25HCDS), 27-hydroxycholesterol-3-sulfate (27HC3S), 27-hydroxycholesterol-disulfate (27HCDS), 24-hydroxycholesterol-3-sulfate (24HC3S), 24-hydroxycholesterol-disulfate (24HCDS), and 24,25-epoxycholesterol-3-sulfate, or salt thereof in an amount ranging from 1 mg/day to 300 mg/day, wherein the human subject has a magnetic resonance imaging-proton density fat fraction (MRI-PDFF) prior to treatment of at least 5%, or a magnetic resonance elastography (MRE) prior to treatment≥2.75 kPa.

3. The method of claim 2, wherein the diabetes is type I diabetes.

4. The method of claim 2, wherein the diabetes is type II diabetes.

5. The method of claim 1, wherein the human subject has non-alcoholic steatohepatitis (NASH).

6. A method of treating non-alcoholic steatohepatitis (NASH) and at least one of insulin resistance, diabetes and prediabetes, in a human subject in need thereof, the method comprising orally administering to the subject at least one compound selected from 25-hydroxycholesterol-3-sulfate (25HC3S), 25-hydroxycholesterol-disulfate (25HCDS), 27-hydroxycholesterol-3-sulfate (27HC3S), 27-hydroxycholesterol-disulfate (27HCDS), 24-hydroxycholesterol-3-sulfate (24HC3S), 24-hydroxycholesterol-disulfate (24HCDS), and 24,25-epoxycholesterol-3-sulfate, or salt thereof in an effective amount, wherein the human subject has a magnetic resonance imaging-proton density fat fraction (MRI-PDFF) prior to treatment of at least 5%, or a magnetic resonance elastography (MRE) prior to treatment≥2.75 kPa.

7. The method of claim 1, wherein the orally administering comprises orally administering the at least one compound in an amount ranging from 1 mg/day to 100 mg/day.

8. The method of claim 1, wherein the orally administering comprises orally administering the at least one compound in an amount ranging from 5 mg/day to 90 mg/day or 10 mg/day to 80 mg/day.

9. The method of claim 1, wherein the orally administering comprises orally administering the at least one compound in an amount ranging from 30 mg/day to 70 mg/day.

10. The method of claim 1, wherein a total amount per kg of the at least one compound that is orally administered to the subject: (a) ranges from 0.1 mg/kg/day to 5 mg/kg/day; or (b) ranges from 0.2 mg/kg/day to 4 mg/kg/day; or (c) ranges from 0.3 mg/kg/day to 3 mg/kg/day; or (d) ranges from 0.4 mg/kg/day to 2 mg/kg/day.

11. The method of claim 1, wherein the orally administering comprises orally administering a plurality of doses of the at least one compound.

12. The method of claim 11, wherein:
(a) the doses are orally administered at a frequency ranging from once weekly to three times a day, or once a day, or twice a day; and/or
(b) the orally administering comprises orally administering for a dosing period of at least 7 days.

13. The method of claim 1, wherein the at least one compound is orally administered in a formulation comprising the at least one compound and a pharmaceutically acceptable carrier.

14. The method of claim 1, wherein:
(a) the at least one compound comprises a salt; or
(b) the at least one compound comprises a salt of 25HC3S; or
(c) the at least one compound comprises a salt that is sodium salt; or
(d) the at least one compound comprises a sodium salt of 25HC3S.

15. The method of claim 1, wherein the subject exhibits one or more of:
(a) a half-life time of the at least one compound in the plasma after administration (T1/2) ranging from 1 hour to 5 hours or from 1.5 hour to 4 hours;

(b) a $C_{max}$ of the at least one compound ranging from 25 ng/mL to 4000 ng/mL, 25 ng/mL to 200 ng/mL, from 50 ng/mL to 150 ng/mL, from 75 ng/mL to 125 ng/mL, from 300 ng/mL to 1500 ng/mL, from 400 ng/mL to 1250 ng/mL, or from 500 ng/mL to 1000 ng/mL;

(c) a $C_{max}$ of the at least one compound ranging from 100 ng/mL to 300 ng/mL, from 120 ng/mL to 250 ng/mL, from 150 ng/mL to 200 ng/mL, from 100 ng/mL to 300 ng/mL, from 120 ng/mL to 250 ng/mL, or from 150 ng/mL to 200 ng/mL, per 100 mg of orally administered at least one compound;

(d) an AUCinf of the at least one compound ranging from 300 ng*h/mL to 1000 ng*h/mL, 400 ng*h/mL to 900 ng*h/mL, from 500 ng*h/mL to 800 ng*h/mL, 2700 ng*h/mL to 9000 ng*h/mL, 3000 ng*h/mL to 8000 ng*h/mL, or from 3500 ng*h/mL to 7000 ng*h/mL;

(e) an AUCinf of the at least one compound ranging from 600 ng*h/mL to 1000 ng*h/mL, 700 ng*h/mL to 900 ng*h/mL, or from 800 ng*h/mL to 900 ng*h/mL, per 100 mg of orally administered at least one compound;

(f) an apparent volume of distribution (Vz/F) of the at least one compound ranging from 300 L to 1000 L, 400 L to 900 L, or from 500 L to 800 L; and (g) an apparent clearance (CL/F) of the at least one compound ranging from 100 L to 200 L/h, 110 L/h to 180 L/h, or from 120 L/h to 160 L/h.

16. The method of claim 1, wherein the human subject is taking a lipid lowering drug, or further comprising administering to the human subject a lipid lowering drug.

17. The method of claim 1, wherein the human subject is taking at least one of insulin, a glitazone, GLP-1, glucagon, DDP-4 inhibitor, atorvastatin, fluvastatin, lovastatin, pitavastatin, pravastatin, rosuvastatin, and simvastatin, or further comprising administering to the human subject at least one of atorvastatin, fluvastatin, lovastatin, pitavastatin, pravastatin, rosuvastatin, and simvastatin.

18. The method of claim 12, wherein the dosing period is at least 14 days.

19. The method of claim 12, wherein the dosing period is at least 28 days.

20. The method of claim 16, wherein the lipid lowering drug is at least one of a statin, fenofibrate, omega-3 fatty acid, icosapent ethyl, and fish oil.

* * * * *